US008865873B2

(12) United States Patent
Liu et al.

(10) Patent No.: US 8,865,873 B2
(45) Date of Patent: Oct. 21, 2014

(54) INTERNALIZING HUMAN MONOCLONAL ANTIBODIES TARGETING PROSTATE CANCER CELLS IN SITU

(75) Inventors: Bin Liu, Hercules, CA (US); James D. Marks, Kensington, CA (US)

(73) Assignee: The Regents of the University of California, Oakland, CA (US)

(*) Notice: Subject to any disclaimer, the term of this patent is extended or adjusted under 35 U.S.C. 154(b) by 856 days.

(21) Appl. No.: 12/724,282

(22) Filed: Mar. 15, 2010

(65) Prior Publication Data
US 2010/0233165 A1 Sep. 16, 2010

Related U.S. Application Data

(63) Continuation-in-part of application No. PCT/US2008/076704, filed on Sep. 17, 2008.

(60) Provisional application No. 60/973,005, filed on Sep. 17, 2007.

(51) Int. Cl.
C07K 16/30 (2006.01)
A61K 51/10 (2006.01)
C07K 16/28 (2006.01)

(52) U.S. Cl.
CPC ....... *A61K 51/1072* (2013.01); *C07K 2317/622* (2013.01); *C07K 2317/77* (2013.01); *C07K 2317/21* (2013.01); *C07K 16/3069* (2013.01); *C07K 16/2803* (2013.01)
USPC .................. 530/388.8; 530/387.3; 530/387.7; 530/391.7

(58) Field of Classification Search
None
See application file for complete search history.

(56) References Cited

U.S. PATENT DOCUMENTS

| 6,469,779 | B2 | 10/2002 | Baer et al. | |
| 6,818,749 | B1 * | 11/2004 | Kashmiri et al. | ........ 530/388.85 |
| 2005/0186214 | A1 | 8/2005 | Liu et al. | |

FOREIGN PATENT DOCUMENTS

| WO | WO/2005/062977 | 7/2005 |
| WO | WO/2009/039192 | 3/2009 |

OTHER PUBLICATIONS

Paul, Fundamental Immunology, 3rd Edition, 1993, pp. 292-295.*
Dall'Acqua et al., Methods 2005; 36:43-60.*
MacCallum et al., J Mol Biol. 1996; 262:732-745.*
Greenspan et al., Nature Biotechnology 1999; 7: 936-37.*
Liu et al., Cancer Research, 2004; 64:704-10.*
Ruan et al., Mol. Cell Proteomics, 2006; 5:2364-73, pub'd online Sep. 18, 2006.*

"Epitope" Definition, Stedman's Online Medical Dictionary, 27th Edition, Oct. 5, 2010, Wolters Kluwer Health, Inc.; available at www.stedmans.com.*
Molecular & Cellular Proteomics: Editorial Policies and Practices, Apr. 2006.*
PCT International Search Report and Written Opinion dated May 4, 2009 issued in PCT/US2008/076704 (WO 2009/039192).
PCT International Preliminary Report on Patentability dated Mar. 24, 2010 issued in PCT/US2008/076704 (WO 2009/039192).
EP Supplementary Search Report dated Aug. 31, 2010 issued in EP08831767.2.
EP Partial Search Report dated Apr. 7, 2011 issued in EP011159671.4.
EP Extended Search Report dated Sep. 22, 2011 issued in EP011159671.4.
EP Office Action dated Apr. 5, 2013 issued in EP011159671.4.
Birkle et al. (2003) "Role of tumor-associated gangliosides in cancer progression." *Biochimie* (Paris) 85(3-4): 455-463.
Clynes et al. (2000) "Inhibitory Fc receptors modulate in vivo cytotoxicity against tumor targets." *Nat. Med.* 6(4): 443-446.
Fuh et al. (2006) "Structure-function studies of two synthetic anti-vascular endothelial growth factor Fabs and comparison with the Avastin Fab." *J. Biol. Chem.* 281(10): 6625-6631.
Gao et al. (2003) "De novo identification of tumor-specific internalizing human antibody-receptor pairs by phage-display methods" *Journal of Immunological Methods* 274: 185-197.
Hakomori (2001) "Tumor-associated carbohydrate antigens defining tumor malignancy: basis for development of anti-cancer vaccines." *Adv. Exp. Med. Biol.* 491: 369-402.
Hanisch (2001) "O-Glycosylation of the mucin type." *Biol. Chem.* 382: 143-149.
Kobata et al. (2005) "Altered glycosylation of proteins produced by malignant cells, and application for the diagnosis and immunotherapy of tumours" *Immunol. Cell Biol.* 83: 429-439.
Liu et al. (2004) "Mapping Tumor Epitope Space by Direct Selection of Single-Chain Fv Antibody Libraries on Prostate Cancer Cells" *Cancer Research* 64(2): 704-710.
McWhirter et al. (2006) "Antibodies selected from combinatorial libraries block a tumor antigen that plays a key role in immunomodulation." *Proc. Natl. Acad. Sci. USA.* 103(4): 1041-1046.
Nielsen et al. (2002) "Therapeutic efficacy of anti-ErbB2 immunoliposomes targeted by a phage antibody selected for cellular endocytosis." *Biochim. Biophys. Acta* 1591: 109-118.
Pirollo et al. (2006) "Tumor-targeting nanoimmunoliposome complex for short interfering RNA delivery." *Hum. Gene Ther.* 17: 117-124.
Ruan et al. (2006) "Identification of Clinically Significant Tumor Antigens by Selecting Phage Antibody Library on Tumor Cells in Situ Using Laser Capture Microdissection" *Molecular & Cellular Proteomics* 5(12): 2364-2373.
Song et al. (2005) "Antibody mediated in vivo delivery of small interfering RNAs via cell-surface receptors." *Nat. Biotechnol.* 23: 709-717.

(Continued)

*Primary Examiner* — Sheela J Huff
*Assistant Examiner* — Jessica H Roark
(74) *Attorney, Agent, or Firm* — Tom Hunter; Weaver Austin Villeneuve & Sampson LLP

(57) ABSTRACT

This invention provides a method that allows selection of antibodies against cells (e.g., tumor cells) in situ using laser capture microdissection. By restricting antibody selection to binders of internalizing epitopes, a panel of phage antibodies was generated that targets clinically represented prostate cancer antigens.

9 Claims, 14 Drawing Sheets

(56) References Cited

OTHER PUBLICATIONS

Ugorski et al. (2002) "Sialyl Lewis(a): a tumor-associated carbohydrate antigen involved in adhesion and metastatic potential of cancer cells." *Acta Biochim. Pol.* 49(2): 303-311.

EP Partial Search Report dated Jul. 4, 2011 issued in EP011159671.4.

Becerril et al. (1999) "Toward selection of internalizing antibodies from phage libraries." *Biochem. Biophys. Res. Commun.* 255: 386-393.

Bonner et al. (1997) "Laser capture microdissection: molecular analysis of tissue." *Science* 278: 1481-1483.

Cai et al. (1995) "Anti-melanoma antibodies from melanoma patients immunized with genetically modified autologous tumor cells: selection of specific antibodies from single-chain Fv fusion phage libraries." *Proc. Natl. Acad. Sci. U.S.A.* 92: 6537-6541.

Covell et al. (2005) "Linking tumor cell cytotoxicity to mechanism of drug action: An integrated analysis of gene expression, small-molecule screening and structural databases" *Proteins* 59: 403-433.

de Kruif et al. (1995) "Rapid selection of cell subpopulation-specific human monoclonal antibodies from a synthetic phage antibody library." *Proc. Natl. Acad. Sci. U.S.A.* 92: 3938-3942.

Degen et al. (1998) "MEMD, a new cell adhesion molecule in metastasizing human melanoma cell lines, is identical to ALCAM (activated leukocyte cell adhesion molecule)." *Am. J. Pathol.* 152: 805-813.

Emmert-Buck et al. (1996) "Laser capture microdissection." *Science* 274: 998-1001.

Garraway et al. (2006) "From Integrated Genomics to Tumor Lineage Dependency" *Cancer Res.* 66: 2506-2508.

Geuijen et al. (2005) "A proteomic approach to tumour target identification using phage display, affinity purification and mass spectrometry." *Eur. J. Cancer* 41: 178-187.

Hughes et al. (2001) "Counting the Uncountable: Statistical Approaches to Estimating Microbial Diversity" *Appl. Environ. Microbiol.* 67: 4399-4406.

Hughes et al. (2005) "The Application of Rarefaction Techniques to Molecular Inventories of Microbial Diversity" *Meth. Enzymol.* 397: 292-308.

Huie et al. (2001) "Antibodies to human fetal erythroid cells from a nonimmune phage antibody library" *Proc. Natl. Acad. Sci., USA* 98: 2682-2687.

Kristiansen et al. (2005) "Expression profiling of microdissected matched prostate cancer samples reveals CD166/MEMD and CD24 as new prognostic markers for patient survival" *J. Pathol.* 205: 359-376.

Lekkerkerker et al. (1999) "Phage antibodies against human dendritic cell subpopulations obtained by flow cytometry-based selection on freshly isolated cells." *J. Immunol. Methods* 231, 53-63.

Liu et al. (2000) "Applying Phage Antibodies to Proteomics: Selecting Single Chain Fv Antibodies to Antigens Blotted on Nitrocellulose" *Anal. Biochem.* 286: 119-128.

Liu et al. (2002) "Towards proteome-wide production of monoclonal antibody by phage display." *J. Mol. Biol.* 315: 1063-1073.

Lu et al. (2004) "Application of laser capture microdissection to phage display peptide library screening" *Oral Surg. Oral Med. Oral Pathol. Oral Radiol. Endod.* 98: 692-697.

Marks et al. (1991) "By-passing immunization: Human antibodies from V-gene libraries displayed on phage." *J. Mol. Biol.* 222: 581-597.

Marks et al. (1992) "By-passing immunization: building high affinity human antibodies by chain shuffling." *Biotechnology* (N.Y.) 10: 779-783.

Marks et al. (1992) "Molecular evolution of proteins on filamentous phage. Mimicking the strategy of the immune system." *J. Biol. Chem.* 267: 16007-16010.

O'Connell et al. (2002) "Phage versus phagemid libraries for generation of human monoclonal antibodies." *J. Mol. Biol.* 321: 49-56.

Piazza et al. (2005) "Internalization and recycling of ALCAM/CD166 detected by a fully human single-chain recombinant antibody" *J. Cell Sci.* 118: 1515-1525.

Pini et al. (1998) "Design and use of a phage display library. Human antibodies with subnanomolar affinity against a marker of angiogenesis eluted from a two-dimensional gel." *J. Biol. Chem.* 273: 21769-21776.

Poul et al. (2000) "Selection of tumor-specific internalizing human antibodies from phage libraries." *J. Mol. Biol.* 301: 1149-1161.

Saifullah et al. (2004) "Expression and Characterization of a Novel CD6 Ligand in Cells Derived from Joint and Epithelial Tissues" *J. Immunol.* 173: 6125-6133.

Saito et al. (2004) "Distribution of Liposomes into Brain and Rat Brain Tumor Models by Convection-Enhanced Delivery Monitored with Magnetic Resonance Imaging" *Cancer Res.* 64: 2572-2579.

Saito et al. (2005) "Gadolinium-loaded liposomes allow for real-time magnetic resonance imaging of convection-enhanced delivery in the primate brain." *Exp. Neurol.* 196: 381-389.

Sharon et al. (2005) "Recombinant poly-clonal antibodies for cancer therapy." *J. Cell. Biochem.* 96: 305-313.

Silacci et al. (2005) "Design, construction, and characterization of a large synthetic human antibody phage display library." *Proteomics* 5: 2340-2350.

Yao et al. (2005) "Targeting Pancreatic Islets with Phage Display Assisted by Laser Pressure Catapult Microdissection" *Am. J. Pathol.* 166, 625-636.

\* cited by examiner

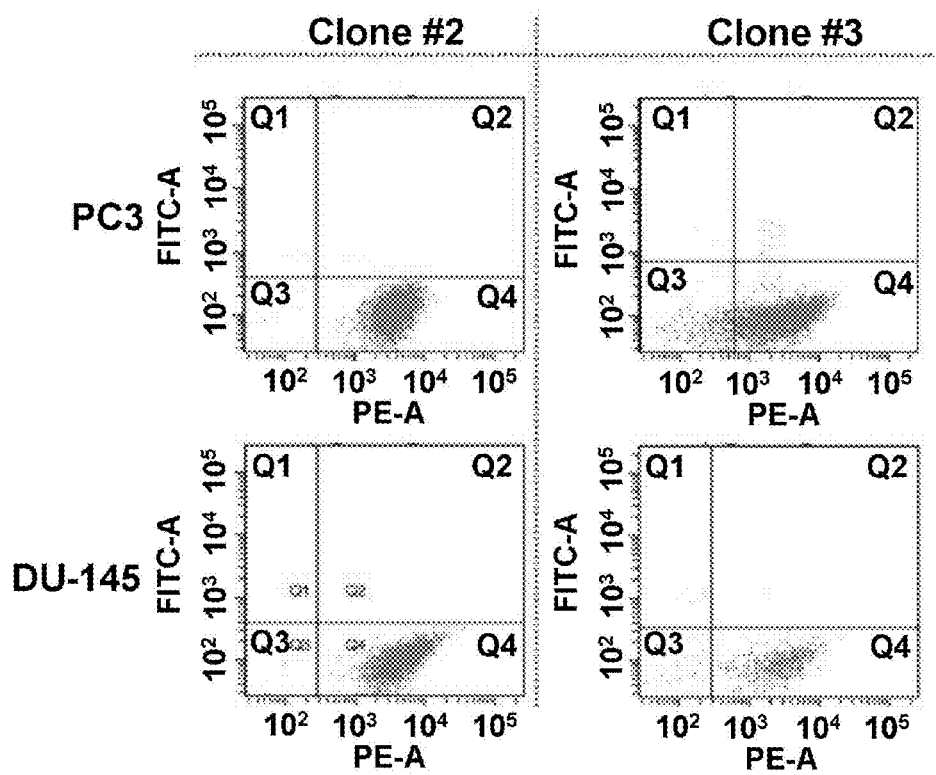
*Fig. 3, cont'd.*

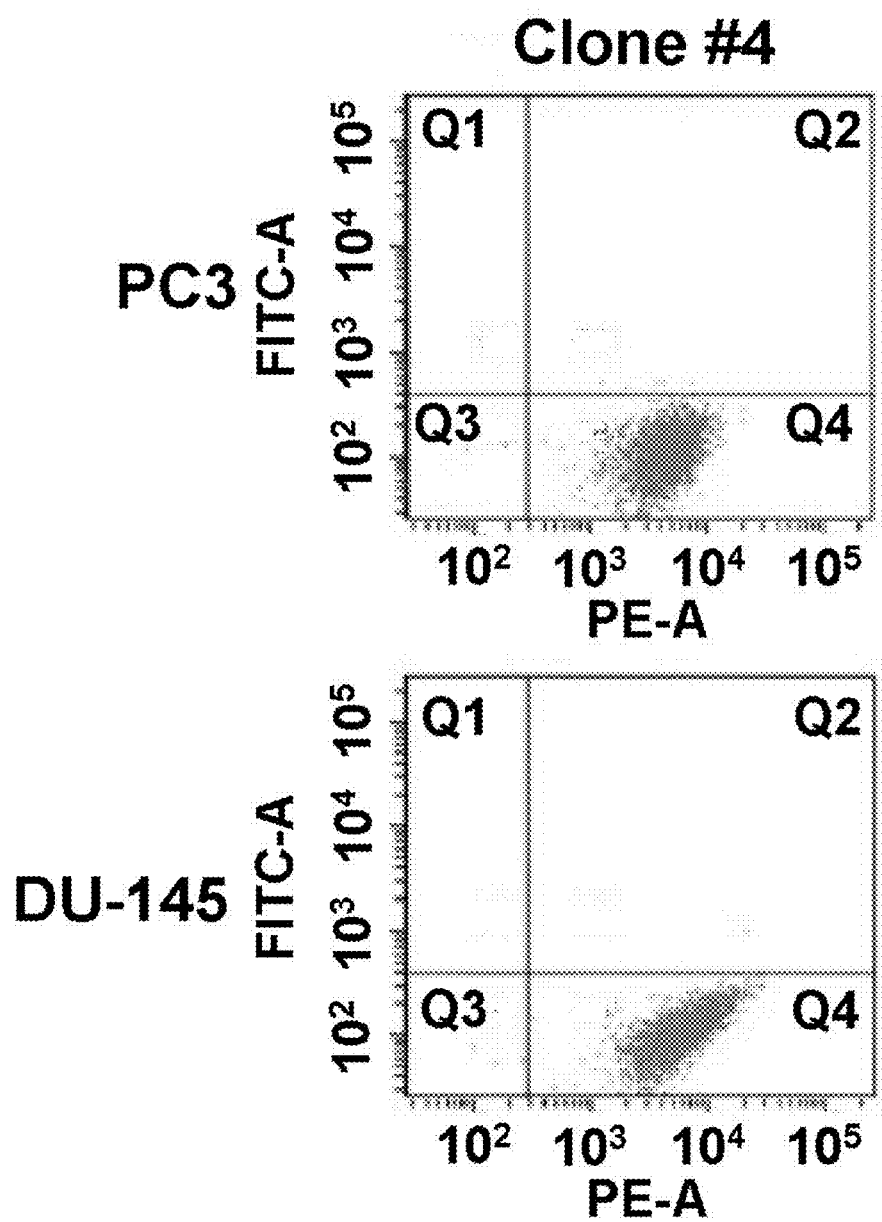
*Fig. 3, cont'd.*

| Heavy chain | | | | | | | | Linker | Light chain | | | | | | |
|---|---|---|---|---|---|---|---|---|---|---|---|---|---|---|---|
| Clone | Frame 1 | CDR1 | Frame 2 | CDR2 | Frame 3 | CDR3 | Frame 4 | | Frame 1 | CDR1 | Frame 2 | CDR2 | Frame 3 | CDR3 | Frame 4 |
| 3051.1 | QVQLQESGGGLVK PGGSLRLSCAASG FTFS | SYGMY | WVRQAPGKG LEWVS | TLSKSGS GTYYADS VKG | RFTISRDNSKN TLYLQMNSLRA EDTAVYYCAS | IAVAGN YFDY | WGQGTLVTVS S | GGGGSGGGG SGGGGS | SYVLTQDPA VSVALGQTV RITC | QGDSLRS YYAS | WYQERPGQAP LLVI | YGKNNR PS | GIPDRFSGSSNS GSTATLTISRV EAGDEGEYYC | QVWDSI NEQVV | FGGGTKVTVL |
| G12PC3 | QVQLVQSGGGVVQ PGRSLRLSCAATG IFFS | GSGMH | WVRQAPGKG LEWVT | MIWWDGS NKFYADS VKG | RFTISRDNSKN TLYLQMDSLRA EDTAVYFCAR | DKGVRS MDV | WGLGTVTVTVS S | GGGGSGGGG SGGGGS | NFMLTQPPS VSVAPGQTA KITC | DGVSIRT KSVR | WYQQKPGQAP VVVV | HDDSDR PS | GIPEEFSGSGNS GTTATLISRV EAGDEADYYC | QAWDSI SEEVV | FGGGTKLTVL |
| M6c42b | QVQLQESGGGLVQ PGGSLRLSCAASG FTPG | TYAMR | WVRQISGKG LEWIV | GLEVSGD AXYTDSV RG | RFTISRDNSKN TLYLQMNTLRA EDTAVYYCAR | KSSTTS MDY | WGRGTLVTVS S | GGGGSGGGG SGGGGS | SYVLTQDPA VSVALGNTV RITC | QGENIGS KSVH | WYQQKPGQAP VLVV | VDDSDR PS | GIPERFSGSSNS GTTATLTISSV EAGDEADYYC | QAWDSI SEHVI | FGGGTKVTVL |
| 4F3YW | QVQLQESGGGLVQ PGGSLRLSCAASG FTFS | SYAMH | WVRAQAPGKG LEWVA | VLSTDGS NKYYADS VKG | RFTISRDNSNRN TLYLQMNSLRA EDTAVYYCAR | FSSGWY YFDY | WGQGTLVTVS S | GGGGSGGGG SGGGGS | DIQMTQSPS FLSASVGDR ITITC | RASHDIS SYFA | WYQQKPGKAP KPLI | YAASTL QS | GVPSRFSGSGS GTEFTLTISSL QEEDFATYYC | CQLGSY PLIT | FGGGTKLEIK |
| M40prl46 | QVQLVQSGGGLVQ PGGSLRLSCAASG FTFS | SYAMS | WVRQAPGKG LEWVS | AISGSGG STYYTDS VKG | RFTISRDNSKN TLYLQMNSLRA EDTAVYYCAK | SHDYGD VAGFDY | WGQGTLVTVS S | GGGGSGGGG SGGGGS | HVLLTQDPA VSVALGQTV RITC | QGDSLRS YYAS | WYQQKPGQAP VLVI | YGKNNR PS | GIPDRFSGSSS GTTASLTITGA QAEDEADYYC | HSRDSS G2NLRV | FGGGTKLTVL |
| UA20 | QVQLQESGGGLVK PGGSLRLSCAASG FTFS | NAWMN | WVRQAPGKG LEWVG | RIKSKTD EGTNDYA APVKG | RFSISKDSKN TLYLQMNSLRT EDTGVYYCTA | TKGLGG SK | LGQGTLVTVS S | GGGGSGGGG SGGGGS | QSVLTQFPS ASGTPGQRV TISC | SGSSSNI GRNTVN | WSRQLPGTAP KLLI | YSNDQR PS | GVPDRFSGSKS GTSASLAITGL QFEDEADYYC | GTWDSS LSAYY | FGTGTKLTVL |
| UA8 | QVQLVESGGGVVQ PGRSLRLSCAASG FTFS | SFGMH | WVRAAPGKG LEWVA | VISIDGS MQYYADS VKG | RFTISRDNSKN TLYLQMNSLRA EDTAVYYCGS | RPGGGY ASGSTV AY | WGQGTFVTVS S | GGGGSGGGG SGGGGS | SSELLTQDPA VSVALGQTV RITC | QGDSLRS YYAS | WYQQKPGQAP LLVI | YGQNIR PS | GIPDRFSGSSS GNSASLTITGA QAEDEADYYC | HSRDSS GRYV | FGVGTKVTVL |
| 5851I41 | QVQLVESGGGLVQ PGGSLRLSCAASG FTFS | SYAMS | WVRQAPGKG LEWVS | AISGSGG STYYADS VKG | RFTISRDNSKD TLYLQMNSLRA EDTAVYYCAS | RSLLLDY | WGQGTLVTVS S | GGGGSGGGG SGGGGS | NFMLTQDPA VSVALGQTV RITC | QGDSLRS YYAS | WYQQKPGQAP LLVI | YGKNNR PS | GIPDRFSGSSS GNTASLTITGA QAEDEADYYC | NSRDSS GNPV | FGGGTKVTVL |
| 5851I41.1 | QVQLVESGGGLVQ PGGSLRLSCAASG FTFS | SYAMS | WVRQAPGKG LEWVS | AISGSGG STYYADS VKG | RFTISRDNSKD TLYLQMNSLRA EDTAVYYCAS | RSLLLDY | WGQGTLVTVS S | GGGGSGGGG SGGGGS | NFMLTQDPA VSVALGQTV RITC | QGDSLRS YYAS | WYQQKPGQAP VLVV | YGKNNR PS | GIPDRFSGSSS GNTASLTITGA QAEDEADYYC | NSRDSS GNPV | FGGGTKVTVL |
| 5851I56 | QVQLQESGGGLVQ LGGSLRLSCAASG FTFS | SYAMS | WVRQAPGKG LEWVS | AISGSGG STYYADS VKG | RFTISRDNSKN TLYLQMSSLRA EDTAVYYCAN | SAYTGG NYDY | WGRGTLVTVS S | GGGGSGGGG SGGGGS | SSELLTQDPA VSVALGQTV KITC | QGDSLRT YYAS | WYQQKPGQAP VLVI | YGBENGR PS | GIPDRFSGSSS GNTASLTITGA QAEDEADYYC | NSRDSS GSHLRV | FGGGTKLTVL |
| 3076 | QVNLRESGGGGLVQ PGGFLRLSCAAFG FTFS | GYNMS | WVHPAFGKG LEWVA | NIKQDGS EKFYVDS VKG | RFTISRDNAKN SLFLQMNSLRA EDTAVYFCAR | GLLSDY | WGQGTLVFVS S | GGGGSGGGG SGGGGS | NFMLTQPPS VSVAPGKTA SLIC | GGYNIGT KSVH | WYQQKPGQAP VVVV | HDDSDR PS | GIPERFSGSGNS GTTATLIIRV EAGDEADYYC | QAWDSI SEEVV | FGGGTKLTVL |
| 3051 | QVQLQESGGGLVK PGGELRLSCAASG FTFS | SYGMY | WVRQAPGKG LEWVS | TLSRSGS GTYAES VKG | RFTISRDNSKN TLYLQMNSLRA EDTAVYYCAS | IAVAGN YFEY | WGQGTLVTVS S | GGGGSGGGG SGGGGS | SYVLTQDPA VSVALGQQV RITC | QGDSLRS YYAS | WYQERPGQAP LLVI | YGKNNR PS | GIPDRFSGSSNS GSTATLTISRV EAGDEGDYYC | QVWDSI NEQVV | FGGGTKVTVL |

Fig. 7

| Heavy chain | | | | | | | | Linker | Light chain | | | | | | |
|---|---|---|---|---|---|---|---|---|---|---|---|---|---|---|---|
| Clone | Frame 1 | CDR1 | Frame 2 | CDR2 | Frame 3 | CDR3 | Frame 4 | Linker | Frame 1 | CDR1 | Frame 2 | CDR2 | Frame 3 | CDR3 | Frame 4 |
| M49R | QVQLQESGGGLVK PGESLRLSCAASG FTFS | DHYMD | WVRQAPGKG LEWVA | YIRYDGS TKYYADS VKG | RFTISRDNSKN TLIYLQMNSLRF EDTAFYYCAR | LIAEAE GWNFP | WGQGTLVTVS S | GGGGSGGGG SGGGGS | NFMLTQPPS VSVAPGKTA RITC | GGNNIGS KSVY | WYQQKPGQAP VLVV | YDDSDR PS | GIPERFSGSNS GNTALTISRV EAGDEADYYC | QVWDSS SDHVV | FGGGTKLTVL |
| RCI-14 | QVQLLQSAGGLVQ PGGSLRLSCAASG FTFS | TYAMN | WVRQAPGKG LEWVS | GISGSGG STNYADS VKG | RFTISRDSSKN TLFYQMNSLRA EDTAVYYCAK | DYGSGW YDY | WGQGTLVTVS S | GGGGSGGGG SGGGGS | SSELTQDPA VSVALGQTV RITC | QGDSLRS YYAS | WYQERPGQAP LLVI | YGRNER PS | GIPDRFSASSS GNTASLTITGA QAEDEADYYC | QVWDSF NEQVV | FGGGTKLTVL |
| II79_4 | QVQLVESGGGLVQ PGGSLRLSCAASG FTFS | SYAMS | WVHQAPGKG LEWVS | AISGSGG STYYADS VKG | RFTISRDNSKN TLIYLQMNSLRA EDTAVYYCAK | TYYGFW SGYYDY | LGQGTLVTVS S | GGGGSGGGG SGGGGS | SSELTQDPA VSVGLGQTV TITC | QGDSLES YYAN | WYQQKPGQAP IILVI | YGENNR PS | GIPDRFSGSSS GNTASLTITGA QAEDEADYYC | HSRDSS GTHLRV | FGGGTKLTVL |
| II79_3 | QVQLESGGGVVQ PGTSLRLSCAASG FTFS | NYAIN | WVRQAAGKG LEWVS | GISGSGV STSYADS VKG | RFTVSRDNSKN TLIYLQMNSLRV EDTALYYCAK | NGGGPE YLQH | WGQGTLVTVS S | GGGGSGGGG SGGGGS | QSVLTQPPS ASSTPGQRV TISC | SGSSSNI GNNTVN | WSRQLPGTAP KLLI | YSNDQR PS | GVPDRFSGSKS GTSASLAITGL QPEDEADYYC | GTWDSS LSAYV | FGTGTKLTVL |
| T5II-4B.1 | QVQLQESGGTLVQ PGGSLRLSCAASG FTFS | SYAMS | WVRQAPGRG LEWVS | TISGSGG STYYADS VKG | RFTISRDNSKN TLIYLQMNSLRA EDTAVYYCAK | GAYSGS Y | WGQGTLVTVS S | GGGGSGGGG SGGGGS | SSELTQDPA VSVALGQTV RITC | QGDSLRS YYAS | WYQQKPGQAP SLVI | YGENSR PS | GIPDRFSGSSS GNTASLTITGA QAENEADYYC | QAWDSS TAVV | FGGGTKLTVL |
| T5II-4B.2 | QVQLQESGGTLVQ PGGSLRLSCAASG FTFS | SYAMS | WVRQAPGRG LEWVS | TISGSGG STYYADS VKG | RFTISRDNSKN TLIYLQMNSLRA EDTAVYYCAK | GAYSGS H | WGQGTLVTVS S | GGGGSGGGG SGGGGS | SSELTQDPA VSVALGQTV RITC | QGDSLRS YYAS | WYQQKPGQAP SLVI | YGENSR PS | GIPDRFSGSSS GNTASLTITGA QAENEADYYC | QAWDSS TAVV | FGGGTKLTVL |
| RCI-11 | QVQLVESGAZVKK PGASVKVSCKASG YTPT | SYGIS | WVRQAPGQG LEWMG | WISAYNG NTNYAQK LQG | RVTMTTDTSTS TAYMELRSLRS DDTAVYYCAR | PIYDSS GYDAFD I | WGQGTMVTVS S | GGGGSGGGG SGGGGS | DIVMTQSPS TLSASIGDR VTITC | RASEGIY HWLA | WYQQKPGKAP KLLI | YKASSL AS | GAPSRFSGSGS GTDFTLTISSL QPDDFATYYC | QQYHTI SRT | FGPGTKVDIK |
| RCI-20 | QVQLVESGGGLVK PGGSLRLSCAASG FTFS | SYAMH | WVRQAPGKG LEWVA | VISYDGS NKYYADS VKG | RFTISHDNSKN TLIYLQMNSLRA EDTAVYFCVR | PSDSGW SFEH | WGQGTLVPVS S | GGGGSGGGG SGGGGS | QSVLTQPPS ASSTPGQRV TISC | SGSSSNI GNNTVN | WSRQLPGTAP KLLI | YSNDQR PS | GVPDRFSGSKS GTSASLAITEL QPEDEADYYC | GTWDSS LSAYV | FGTNSTKLTVL |
| CI-11A | QVQLQESGGGLVQ PGGSLRLSCAASG FTFS | SYAMS | WVRQAPGKG LEWVA | VISYDGS NKYYADS VKG | RFTISRDNSKN TLIYLQMNSLRA EDTAVYYCVR | GDRSYG AEYFQH | WGQGTLVTVS S | GGGGSGGGG SGGGGS | SSELTQDPA VSVASGQTV RITC | QGDSLRS YYAS | WYQQKPGQAP LLVI | YGKNIR PS | GIPDRFSGSTS GNSASLTTTGA QAEDEADYYC | NSRDSS GNRRWV | FGGGTKLTVL |
| CI-14A | QVQLQESGGGLVK PGGSLRLSCAASG FTSS | SYAMH | WVRQAPGKG LEYVS | AIGGNGG TYYADSV KG | RFTISRDNSKN TLIYLQMNSLRA EDTAVYYCAK | EGEQWL EYRYYY GMDV | WGQGTTVTVS S | GGGGSGGGG SGGGGS | SSELTQDPA VSVALGQTV RITC | QGDSLRS YYAS | WYQQKPGQAP SLVI | YGENSR PS | GIPDRFSGSSS GNTASLTITGA QAENEADYYC | QAWDSS TAVV | FGGGTKLTVL |
| 595-2 | QVQLVESGGGVVQ PGRSLRLSCAASG FTFS | SYGMH | WVRQAPGKG LEWVA | VISYDGS NKYYADS VKG | RFTISRDNSKN TLIYLQMNSLRA EDTAVYYCAR | GGRYSS NWFSYY YYGMDV | WGQGTVTVTS S | GGGGSGGGG SGGGGS | NFMLTQPPS VSVAPGKTA RITC | GGNNIGS KSVY | WYQQKPGQAP VLVV | YDDSDR PS | GIPERFSGSNS GNTALTISRV EAGDEADYYC | QVWDSS SDHVV | FGGGTKLTVL |

*Fig. 8*

SEQUENCE LISTING

```
<160> NUMBER OF SEQ ID NOS: 350

<210> SEQ ID NO 1
<211> LENGTH: 7
<212> TYPE: PRT
<213> ORGANISM: Artificial
<220> FEATURE:
<223> OTHER INFORMATION: Peptide linker.

<400> SEQUENCE: 1

Gly Gly Gly Gly Ser Ser Ser
1               5

<210> SEQ ID NO 2
```

```
<211> LENGTH: 8
<212> TYPE: PRT
<213> ORGANISM: Artificial
<220> FEATURE:
<223> OTHER INFORMATION: Single chain antibody.

<400> SEQUENCE: 2

Asp Tyr Lys Asp Asp Asp Asp Lys
1               5

<210> SEQ ID NO 3
<211> LENGTH: 242
<212> TYPE: PRT
<213> ORGANISM: Artificial
<220> FEATURE:
<223> OTHER INFORMATION: Single chain antibody.

<400> SEQUENCE: 3

Gln Val Gln Leu Gln Glu Ser Gly Gly Gly Leu Val Lys Pro Gly Gly
1               5                   10                  15

Pro Leu Arg Leu Ser Cys Ala Ala Ser Gly Phe Thr Phe Ser Ser Tyr
                20                  25                  30

Gly Met Tyr Trp Val Arg Gln Ala Pro Gly Lys Gly Leu Glu Trp Val
            35                  40                  45

Ser Thr Leu Ser Arg Ser Gly Ser Gly Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ile Ala Val Ala Gly Asn Tyr Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ser Tyr Val Leu Thr Gln Asp Pro Ala Val
    130                 135                 140

Ser Val Ala Leu Gly Gln Thr Val Arg Ile Thr Cys Gln Gly Asp Ser
145                 150                 155                 160

Leu Arg Ser Tyr Tyr Ala Ser Trp Tyr Gln Glu Arg Pro Gly Gln Ala
                165                 170                 175

Pro Leu Leu Val Ile Tyr Gly Lys Asn Asn Arg Pro Ser Gly Ile Pro
            180                 185                 190

Asp Arg Phe Ser Gly Ser Asn Ser Gly Ser Thr Ala Thr Leu Thr Ile
        195                 200                 205

Ser Arg Val Glu Ala Gly Asp Glu Gly Asp Tyr Tyr Cys Gln Val Trp
    210                 215                 220

Asp Ser Ile Asn Glu Gln Val Val Phe Gly Gly Thr Lys Val Thr
225                 230                 235                 240

Val Leu

<210> SEQ ID NO 4
<211> LENGTH: 241
<212> TYPE: PRT
<213> ORGANISM: Artificial
<220> FEATURE:
<223> OTHER INFORMATION: Single chain antibody.

<400> SEQUENCE: 4

Gln Val Gln Leu Val Gln Ser Gly Gly Gly Val Val Gln Pro Gly Arg
```

```
            1               5                  10                 15
        Ser Leu Arg Leu Ser Cys Ala Ala Thr Gly Ile Pro Phe Ser Gly Ser
                        20                 25                 30

Gly Met His Trp Val Arg Gln Ala Pro Gly Lys Gly Leu Glu Trp Val
                        35                 40                 45

Thr Met Ile Trp Tyr Asp Gly Ser Asn Lys Phe Tyr Ala Asp Ser Val
                    50                 55                 60

Lys Gly Arg Phe Thr Ile Ser Arg Asp Asn Ser Lys Asn Thr Leu Tyr
        65                  70                 75                 80

Leu Gln Met Asp Ser Leu Arg Ala Glu Asp Thr Ala Val Tyr Phe Cys
                        85                 90                 95

Ala Arg Asp Lys Gly Val Arg Ser Met Asp Val Trp Gly Leu Gly Thr
                        100                105                110

Thr Val Thr Val Ser Ser Gly Gly Gly Ser Gly Gly Gly Gly Ser
                    115                120                 125

Gly Gly Gly Gly Ser Asn Phe Met Leu Thr Gln Pro Pro Ser Val Ser
                    130                135                140

Val Ala Pro Gly Gln Thr Ala Lys Ile Thr Cys Asp Gly Tyr Ser Ile
        145                 150                155                160

Arg Thr Lys Ser Val His Trp Tyr Gln Gln Lys Pro Gly Gln Ala Pro
                        165                170                175

Val Val Val Val His Asp Asp Ser Asp Arg Pro Ser Gly Ile Pro Glu
                        180                185                190

Arg Phe Ser Gly Ser Asn Ser Gly Thr Thr Ala Thr Leu Thr Ile Ser
                        195                200                205

Arg Val Glu Ala Gly Asp Glu Ala Asp Tyr Tyr Cys Gln Ala Trp Asp
                        210                215                220

Ser Ile Ser Glu Glu Val Val Phe Gly Gly Thr Lys Leu Thr Val
        225                 230                235                240

Leu

<210> SEQ ID NO 5
<211> LENGTH: 240
<212> TYPE: PRT
<213> ORGANISM: Artificial
<220> FEATURE:
<223> OTHER INFORMATION: Single chain antibody.

<400> SEQUENCE: 5

Gln Val Gln Leu Gln Glu Ser Gly Gly Gly Leu Val Gln Pro Gly Gly
        1               5                  10                 15

Ser Leu Arg Leu Ser Cys Ser Ala Ser Gly Phe Thr Phe Gly Thr Tyr
                        20                 25                 30

Ala Met Arg Trp Val Arg Gln Thr Ser Lys Gly Leu Glu Trp Val
                        35                 40                 45

Ser Gly Ile Gly Val Ser Gly Asp Ala Tyr Tyr Thr Asp Ser Val Arg
                    50                 55                 60

Gly Arg Phe Thr Ile Ser Arg Asp Asn Ser Lys Asn Thr Leu Tyr Leu
        65                  70                 75                 80

Gln Met Asn Thr Leu Arg Ala Glu Asp Thr Ala Thr Tyr Tyr Cys Thr
                        85                 90                 95

Arg Lys Ser Ser Thr Thr Ser Asn Asp Tyr Trp Gly Arg Gly Thr Leu
                        100                105                110

Val Thr Val Ser Ser Gly Gly Gly Gly Ser Gly Gly Gly Gly Ser Gly
                    115                120                 125
```

```
Gly Gly Gly Ser Ser Tyr Val Leu Thr Gln Asp Pro Ala Val Ser Val
        130                 135                 140
Ala Leu Gly Gln Thr Val Arg Ile Thr Cys Gln Gly Asp Asn Ile Gly
145                 150                 155                 160
Ser Lys Ser Val His Trp Tyr Gln Gln Lys Pro Gly Gln Ala Pro Val
                165                 170                 175
Leu Val Val Tyr Asp Asp Ser Asp Arg Pro Ser Gly Ile Pro Glu Arg
                180                 185                 190
Phe Ser Gly Ser Asn Ser Gly Thr Thr Ala Thr Leu Thr Ile Ser Ser
        195                 200                 205
Val Glu Ala Gly Asp Glu Ala Asp Tyr Tyr Cys Gln Ala Trp Asp Ser
210                 215                 220
Ile Ser Glu His Val Ile Phe Gly Gly Gly Thr Lys Val Thr Val Leu
225                 230                 235                 240
```

<210> SEQ ID NO 6
<211> LENGTH: 241
<212> TYPE: PRT
<213> ORGANISM: Artificial
<220> FEATURE:
<223> OTHER INFORMATION: Single chain antibody.

<400> SEQUENCE: 6

```
Gln Val Gln Leu Gln Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met His Trp Val Arg Gln Ala Pro Gly Lys Gly Leu Glu Trp Val
        35                  40                  45
Ala Val Ile Ser Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Phe Ser Ser Gly Trp Tyr Tyr Phe Asp Tyr Trp Gly Gln Gly
            100                 105                 110
Thr Leu Val Thr Val Ser Ser Gly Gly Gly Gly Ser Gly Gly Gly Gly
        115                 120                 125
Ser Gly Gly Gly Gly Ser Asp Ile Gln Met Thr Gln Ser Pro Ser Phe
    130                 135                 140
Leu Ser Ala Ser Val Gly Asp Arg Ile Thr Ile Thr Cys Arg Ala Ser
145                 150                 155                 160
His Asp Ile Ser Ser Tyr Phe Ala Trp Tyr Gln Gln Lys Pro Gly Lys
                165                 170                 175
Ala Pro Lys Pro Leu Ile Tyr Ala Ala Ser Thr Leu Gln Ser Gly Val
            180                 185                 190
Pro Ser Arg Phe Ser Gly Ser Gly Ser Gly Thr Glu Phe Thr Leu Thr
        195                 200                 205
Ile Ser Ser Leu Gln Pro Glu Asp Phe Ala Thr Tyr Tyr Cys Gln Gln
    210                 215                 220
Leu Gly Ser Tyr Pro Leu Thr Phe Gly Gly Gly Thr Lys Leu Glu Ile
225                 230                 235                 240
Lys
```

```
<210> SEQ ID NO 7
<211> LENGTH: 245
<212> TYPE: PRT
<213> ORGANISM: Artificial
<220> FEATURE:
<223> OTHER INFORMATION: Single chain antibody.

<400> SEQUENCE: 7

Gln Val Gln Leu Leu Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser His Asp Tyr Gly Asp Tyr Ala Gly Phe Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser His Val Ile Leu Thr Gln Asp Pro
    130                 135                 140

Ala Val Ser Val Ala Leu Gly Gln Thr Val Arg Ile Thr Cys Gln Gly
145                 150                 155                 160

Asp Ser Leu Lys Ser Tyr Tyr Ala Ser Trp Tyr Gln Gln Lys Pro Gly
                165                 170                 175

Gln Ala Pro Val Leu Val Ile Tyr Gly Lys Asn Asn Arg Pro Ser Gly
            180                 185                 190

Ile Pro Asp Arg Phe Ser Gly Ser Ser Ser Gly Thr Thr Ala Ser Leu
        195                 200                 205

Thr Ile Thr Gly Ala Gln Ala Glu Asp Glu Ala Asp Tyr Tyr Cys His
    210                 215                 220

Ser Arg Asp Ser Ser Gly Thr His Leu Arg Val Phe Gly Gly Gly Thr
225                 230                 235                 240

Lys Leu Thr Val Leu
                245

<210> SEQ ID NO 8
<211> LENGTH: 244
<212> TYPE: PRT
<213> ORGANISM: Artificial
<220> FEATURE:
<223> OTHER INFORMATION: Single chain antibody.

<400> SEQUENCE: 8

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Glu Gly Thr Thr Asp Tyr Ala Ala
    50                  55                  60
```

```
Pro Val Lys Gly Arg Phe Ser Ile Ser Arg Asp Asp Ser Lys Asn Thr
 65                  70                  75                  80

Leu Tyr Leu Gln Met Asn Ser Leu Lys Thr Glu Asp Thr Gly Val Tyr
                 85                  90                  95

Tyr Cys Thr Ala Thr Lys Gly Leu Gly Gly Ser Lys Leu Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gln Ser Val Leu Thr Gln Pro Pro Ser Ala
130                 135                 140

Ser Gly Thr Pro Gly Gln Arg Val Thr Ile Ser Cys Ser Gly Ser Ser
145                 150                 155                 160

Ser Asn Ile Gly Asn Asn Thr Val Asn Trp Ser Arg Gln Leu Pro Gly
                165                 170                 175

Thr Ala Pro Lys Leu Leu Ile Tyr Ser Asn Asp Gln Arg Pro Ser Gly
            180                 185                 190

Val Pro Asp Arg Phe Ser Gly Ser Lys Ser Gly Thr Ser Ala Ser Leu
        195                 200                 205

Ala Ile Thr Gly Leu Gln Pro Glu Asp Glu Ala Asp Tyr Tyr Cys Gly
210                 215                 220

Thr Trp Asp Ser Ser Leu Ser Ala Tyr Val Phe Gly Thr Gly Thr Lys
225                 230                 235                 240

Leu Thr Val Leu

<210> SEQ ID NO 9
<211> LENGTH: 245
<212> TYPE: PRT
<213> ORGANISM: Artificial
<220> FEATURE:
<223> OTHER INFORMATION: Single chain antibody.

<400> SEQUENCE: 9

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Phe
             20                  25                  30

Gly Met His Trp Val Arg Arg Ala Pro Gly Lys Gly Leu Glu Trp Val
         35                  40                  45

Ala Val Ile Ser Tyr Asp Gly Ser Asn Gln Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Gly Ser Arg Pro Gly Gly Gly Tyr Ala Ser Gly Ser Thr Val Ala Tyr
            100                 105                 110

Trp Gly Gln Gly Thr Pro Val Thr Val Ser Ser Gly Gly Gly Gly Ser
        115                 120                 125

Gly Gly Gly Gly Ser Gly Gly Gly Gly Ser Ser Glu Leu Thr Gln
130                 135                 140

Asp Pro Ala Val Ser Val Ala Leu Gly Gln Thr Val Arg Ile Thr Cys
145                 150                 155                 160

Gln Gly Asp Ser Leu Arg Ser Tyr Tyr Ala Ser Trp Tyr Gln Gln Lys
                165                 170                 175
```

```
Pro Gly Gln Ala Pro Leu Leu Val Ile Tyr Gly Gln Asn Ile Arg Pro
            180                 185                 190

Ser Gly Ile Pro Asp Arg Phe Ser Gly Ser Ser Gly Asn Ser Ala
        195                 200                 205

Ser Leu Thr Ile Thr Gly Ala Gln Ala Glu Asp Glu Ala Asp Tyr Tyr
            210                 215                 220

Cys His Ser Arg Asp Ser Ser Gly Lys Tyr Val Phe Gly Val Gly Thr
225                 230                 235                 240

Lys Val Thr Val Leu
            245

<210> SEQ ID NO 10
<211> LENGTH: 237
<212> TYPE: PRT
<213> ORGANISM: Artificial
<220> FEATURE:
<223> OTHER INFORMATION: Single chain antibody.

<400> SEQUENCE: 10

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Arg Ser Leu Leu Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asn Phe Met Leu Thr Gln Asp Pro Ala Val Ser Val Ala Leu
    130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Leu Leu Val
                165                 170                 175

Ile Tyr Gly Lys Asn Asn Arg Pro Ser Gly Ile Pro Asp Arg Phe Ser
            180                 185                 190

Gly Ser Ser Ser Gly Asn Thr Ala Ser Leu Thr Ile Thr Gly Ala Gln
        195                 200                 205

Ala Glu Asp Glu Ala Asp Tyr Tyr Cys Asn Ser Arg Asp Ser Ser Gly
    210                 215                 220

Asn Pro Val Phe Gly Gly Gly Thr Lys Val Thr Val Leu
225                 230                 235

<210> SEQ ID NO 11
<211> LENGTH: 237
<212> TYPE: PRT
<213> ORGANISM: Artificial
<220> FEATURE:
<223> OTHER INFORMATION: Single chain antibody.

<400> SEQUENCE: 11
```

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Ser Arg Ser Leu Leu Asp Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asn Phe Met Leu Thr Gln Asp Pro Ala Val Ser Val Ala Leu
    130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Leu Leu Val
                165                 170                 175

Ile Tyr Gly Lys Asn Asn Arg Pro Ser Gly Ile Pro Asp Arg Phe Ser
            180                 185                 190

Gly Ser Ser Ser Gly Asn Thr Ala Ser Leu Thr Ile Thr Gly Ala Gln
        195                 200                 205

Ala Glu Asp Glu Ala Asp Tyr Tyr Cys Asn Ser Arg Asp Ser Ser Gly
    210                 215                 220

Asn Pro Val Phe Gly Gly Gly Thr Lys Val Thr Val Leu
225                 230                 235

<210> SEQ ID NO 12
<211> LENGTH: 243
<212> TYPE: PRT
<213> ORGANISM: Artificial
<220> FEATURE:
<223> OTHER INFORMATION: Single chain antibody.

<400> SEQUENCE: 12

Gln Val Gln Leu Gln Glu Ser Gly Gly Gly Leu Val Gln Leu Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Phe Tyr Tyr Cys
                85                  90                  95

Ala Asn Ser Ala Tyr Thr Gly Gly Trp Tyr Asp Tyr Trp Gly His Gly
            100                 105                 110

Thr Leu Val Thr Val Ser Ser Gly Gly Gly Gly Ser Gly Gly Gly Gly
        115                 120                 125

Ser Gly Gly Gly Gly Ser Ser Glu Leu Thr Gln Asp Pro Ala Val
130                 135                 140

Ser Val Ala Leu Gly Gln Thr Val Lys Ile Thr Cys Gln Gly Asp Ser
145                 150                 155                 160

Leu Arg Thr Tyr Tyr Ala Ser Trp Tyr Gln Gln Arg Pro Gly Gln Ala
                165                 170                 175

Pro Val Leu Val Ile Tyr Gly Glu Asn Ser Arg Pro Ser Gly Ile Pro
            180                 185                 190

Asp Arg Phe Ser Gly Ser Ser Ser Gly Asn Thr Ala Ser Leu Thr Ile
        195                 200                 205

Thr Gly Ala Gln Ala Glu Asp Glu Ala Asp Tyr Tyr Cys Asn Ser Arg
    210                 215                 220

Asp Ser Ser Gly Asn His Leu Arg Val Phe Gly Gly Gly Thr Lys Leu
225                 230                 235                 240

Thr Val Leu

<210> SEQ ID NO 13
<211> LENGTH: 238
<212> TYPE: PRT
<213> ORGANISM: Artificial
<220> FEATURE:
<223> OTHER INFORMATION: Single chain antibody.

<400> SEQUENCE: 13

Gln Val Asn Leu Arg Glu Ser Gly Gly Gly Leu Val Gln Pro Gly Gly
1               5                   10                  15

Phe Leu Arg Leu Ser Cys Ala Ala Phe Gly Phe Thr Phe Ser Gly Tyr
            20                  25                  30

Trp Met Ser Trp Val His Pro Ala Pro Gly Lys Gly Leu Glu Trp Val
        35                  40                  45

Ala Asn Ile Lys Gln Asp Gly Ser Glu Lys Phe Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Phe Cys
                85                  90                  95

Ala Arg Gly Leu Leu Ser Asp Tyr Trp Gly Gln Gly Thr Leu Val Pro
            100                 105                 110

Val Ser Ser Gly Gly Gly Gly Ser Gly Gly Gly Ser Gly Gly Gly
        115                 120                 125

Gly Ser Asn Phe Met Leu Thr Gln Pro Pro Ser Val Ser Val Ala Pro
130                 135                 140

Gly Lys Thr Ala Ser Leu Thr Cys Gly Gly Tyr Asn Ile Gly Thr Lys
145                 150                 155                 160

Ser Val His Trp Tyr Gln Gln Lys Pro Gly Gln Ala Pro Val Val Val
                165                 170                 175

Val His Asp Asp Ser Asp Arg Pro Ser Gly Ile Pro Glu Arg Phe Ser
            180                 185                 190

Gly Ser Asn Ser Gly Thr Thr Ala Thr Leu Thr Ile Ile Arg Val Glu
        195                 200                 205

Ala Gly Asp Glu Ala Asp Tyr Tyr Cys Gln Ala Trp Asp Ser Ile Ser
    210                 215                 220

Glu Glu Val Val Phe Gly Gly Gly Thr Lys Leu Thr Val Leu
225                 230                 235

<210> SEQ ID NO 14
<211> LENGTH: 242
<212> TYPE: PRT
<213> ORGANISM: Artificial
<220> FEATURE:
<223> OTHER INFORMATION: Single chain antibody.

<400> SEQUENCE: 14

```
Gln Val Gln Leu Gln Glu Ser Gly Gly Gly Leu Val Lys Pro Gly Gly
  1               5                  10                  15

Pro Leu Arg Leu Ser Cys Ala Ala Ser Gly Phe Thr Phe Ser Ser Tyr
             20                  25                  30

Gly Met Tyr Trp Val Arg Gln Ala Pro Gly Lys Gly Leu Glu Trp Val
         35                  40                  45

Ser Thr Leu Ser Arg Ser Gly Ser Gly Thr Tyr Tyr Ala Glu Ser Val
     50                  55                  60

Lys Gly Arg Phe Thr Ile Ser Arg Asp Asn Ser Lys Asn Thr Leu Tyr
 65                  70                  75                  80

Phe Gln Met Asn Ser Leu Arg Ala Glu Asp Thr Ala Val Tyr Tyr Cys
                 85                  90                  95

Ala Ser Ile Ala Val Ala Gly Asn Tyr Phe Glu Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ser Tyr Val Leu Thr Gln Asp Pro Ala Val
    130                 135                 140

Ser Val Ala Leu Gly Gln Thr Val Arg Ile Thr Cys Gln Gly Asp Ser
145                 150                 155                 160

Leu Arg Ser Tyr Tyr Ala Ser Trp Tyr Gln Glu Arg Pro Gly Gln Ala
                165                 170                 175

Pro Leu Leu Val Ile Tyr Gly Lys Asn Asn Arg Pro Ser Gly Ile Pro
            180                 185                 190

Asp Arg Phe Ser Gly Ser Asn Ser Gly Ser Thr Ala Thr Leu Thr Ile
        195                 200                 205

Ser Arg Val Glu Ala Gly Asp Glu Gly Asp Tyr Tyr Cys Gln Val Trp
    210                 215                 220

Asp Ser Ile Asn Glu Gln Val Val Phe Gly Gly Gly Thr Lys Val Thr
225                 230                 235                 240

Val Leu
```

<210> SEQ ID NO 15
<211> LENGTH: 243
<212> TYPE: PRT
<213> ORGANISM: Artificial
<220> FEATURE:
<223> OTHER INFORMATION: Single chain antibody.

<400> SEQUENCE: 15

```
Gln Val Gln Leu Gln Glu Ser Gly Gly Gly Leu Val Lys Pro Gly Glu
  1               5                  10                  15

Ser Leu Arg Leu Ser Cys Ala Ala Ser Gly Phe Thr Phe Ser Asp His
             20                  25                  30

Tyr Met Asp Trp Val Arg Gln Ala Pro Gly Lys Gly Leu Glu Trp Val
         35                  40                  45

Ala Tyr Ile Arg Tyr Asp Gly Ser Thr Lys Tyr Tyr Ala Asp Ser Val
     50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Phe Tyr Tyr Cys
                 85                  90                  95

Ala Arg Leu Ile Ala Glu Ala Glu Gly Trp Phe Asp Pro Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asn Phe Met Leu Thr Gln Pro Pro Ser
130                 135                 140

Val Ser Val Ala Pro Gly Lys Thr Ala Arg Ile Thr Cys Gly Gly Asn
145                 150                 155                 160

Asn Ile Gly Ser Lys Ser Val Tyr Trp Tyr Gln Gln Lys Pro Gly Gln
                165                 170                 175

Ala Pro Val Leu Val Val Tyr Asp Asp Ser Asp Arg Pro Ser Gly Ile
            180                 185                 190

Pro Glu Arg Phe Ser Gly Ser Asn Ser Gly Asn Thr Ala Thr Leu Thr
        195                 200                 205

Ile Ser Arg Val Glu Ala Gly Asp Glu Ala Asp Tyr Tyr Cys Gln Val
210                 215                 220

Trp Asp Ser Ser Ser Asp His Val Val Phe Gly Gly Gly Thr Lys Val
225                 230                 235                 240

Thr Val Leu

<210> SEQ ID NO 16
<211> LENGTH: 241
<212> TYPE: PRT
<213> ORGANISM: Artificial
<220> FEATURE:
<223> OTHER INFORMATION: Single chain antibody.

<400> SEQUENCE: 16

Gln Val Gln Leu Leu Gln Ser Ala Gly Gly Leu Val Gln Pro Gly Gly
 1               5                  10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
            35                  40                  45

Ser Gly Ile Ser Gly Ser Gly Ser Thr Asn Tyr Ala Asp Ser Val
        50                  55                  60

Lys Gly Arg Phe Thr Ile Ser Arg Asp Ser Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Lys Asp Tyr Gly Ser Gly Trp Tyr Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Ser Glu Leu Thr Gln Asp Pro Ala Val Ser
130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Glu Arg Pro Gly Gln Ala Pro
                165                 170                 175

Leu Leu Val Ile Tyr Gly Arg Asn Glu Arg Pro Ser Gly Ile Pro Asp
```

```
                180                 185                 190
Arg Phe Ser Ala Ser Ser Gly Asn Thr Ala Ser Leu Thr Ile Thr
            195                 200                 205

Gly Ala Gln Ala Glu Asp Glu Ala Asp Tyr Tyr Cys Gln Val Trp Asp
        210                 215                 220

Ser Phe Asn Glu Gln Val Val Phe Gly Gly Gly Thr Lys Leu Thr Val
225                 230                 235                 240

Leu

<210> SEQ ID NO 17
<211> LENGTH: 245
<212> TYPE: PRT
<213> ORGANISM: Artificial
<220> FEATURE:
<223> OTHER INFORMATION: Single chain antibody.

<400> SEQUENCE: 17

Gln Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val His Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Tyr Tyr Gly Phe Trp Ser Gly Tyr Tyr Asp Tyr Leu Gly
            100                 105                 110

Gln Gly Thr Leu Val Thr Val Ser Ser Gly Gly Gly Ser Gly Gly
        115                 120                 125

Gly Gly Ser Gly Gly Gly Ser Ser Glu Leu Thr Gln Asp Pro
    130                 135                 140

Ala Val Ser Val Gly Leu Gly Gln Thr Val Thr Ile Thr Cys Gln Gly
145                 150                 155                 160

Asp Ser Leu Arg Ser Tyr Tyr Ala Asn Trp Tyr Gln Gln Lys Pro Gly
                165                 170                 175

Gln Ala Pro Ile Leu Val Ile Tyr Gly Glu Asn Asn Arg Pro Ser Gly
            180                 185                 190

Ile Pro Asp Arg Phe Ser Gly Ser Ser Ser Gly Asn Thr Ala Ser Leu
        195                 200                 205

Thr Ile Thr Gly Ala Gln Ala Glu Asp Glu Ala Asp Tyr Tyr Cys His
    210                 215                 220

Ser Arg Asp Ser Ser Gly Thr His Leu Arg Val Phe Gly Gly Gly Thr
225                 230                 235                 240

Lys Leu Thr Val Leu
                245

<210> SEQ ID NO 18
<211> LENGTH: 244
<212> TYPE: PRT
<213> ORGANISM: Artificial
<220> FEATURE:
<223> OTHER INFORMATION: Single chain antibody.
```

<400> SEQUENCE: 18

Gln Val Gln Leu Leu Glu Ser Gly Gly Val Val Gln Pro Gly Thr
1               5                   10                  15

Ser Leu Arg Leu Ser Cys Ala Ala Ser Gly Phe Thr Phe Ser Asn Tyr
            20                  25                  30

Ala Ile Asn Trp Val Arg Gln Ala Gly Lys Gly Leu Glu Trp Val
            35                  40                  45

Ser Gly Ile Ser Gly Ser Gly Val Ser Thr Ser Tyr Ala Asp Ser Val
        50                  55                  60

Lys Gly Arg Phe Thr Val Ser Arg Asp Asn Ser Lys Asn Thr Leu Tyr
65                  70                  75                  80

Leu Gln Met Asn Ser Leu Arg Val Glu Asp Thr Ala Leu Tyr Tyr Cys
                85                  90                  95

Ala Lys Asn Gly Gly Gly Pro Glu Tyr Leu Gln His Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Gln Ser Val Leu Thr Gln Pro Pro Ser Ala
        130                 135                 140

Ser Gly Thr Pro Gly Gln Arg Val Thr Ile Ser Cys Ser Gly Ser Ser
145                 150                 155                 160

Ser Asn Ile Gly Asn Asn Thr Val Asn Trp Ser Arg Gln Leu Pro Gly
                165                 170                 175

Thr Ala Pro Lys Leu Leu Ile Tyr Ser Asn Asp Gln Arg Pro Ser Gly
            180                 185                 190

Val Pro Asp Arg Phe Ser Gly Ser Lys Ser Gly Thr Ser Ala Ser Leu
        195                 200                 205

Ala Ile Thr Gly Leu Gln Pro Glu Asp Glu Ala Asp Tyr Tyr Cys Gly
    210                 215                 220

Thr Trp Asp Ser Ser Leu Ser Ala Tyr Val Phe Gly Thr Gly Thr Lys
225                 230                 235                 240

Leu Thr Val Leu

<210> SEQ ID NO 19
<211> LENGTH: 238
<212> TYPE: PRT
<213> ORGANISM: Artificial
<220> FEATURE:
<223> OTHER INFORMATION: Single chain antibody.

<400> SEQUENCE: 19

Gln Val Gln Leu Gln Glu Ser Gly Gly Thr Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Arg Gly Leu Glu Trp Val
            35                  40                  45

Ser Thr Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Tyr Ser Gly Ser Tyr Trp Gly Gln Gly Thr Leu Val
            100                 105                 110

```
Thr Val Ser Ser Gly Gly Gly Ser Gly Gly Gly Ser Gly Gly
        115                 120                 125

Gly Gly Ser Ser Ser Glu Leu Thr Gln Asp Pro Ala Val Ser Val Ala
130                 135                 140

Leu Gly Gln Thr Val Arg Ile Thr Cys Gln Gly Asp Ser Leu Arg Ser
145                 150                 155                 160

Tyr Tyr Ala Ser Trp Tyr Gln Gln Lys Pro Gly Gln Ala Pro Ser Leu
                165                 170                 175

Val Ile Tyr Gly Glu Asn Ser Arg Pro Ser Gly Ile Pro Asp Arg Phe
                180                 185                 190

Ser Gly Ser Ser Ser Gly Asn Thr Ala Ser Leu Thr Ile Thr Gly Ala
                195                 200                 205

Gln Ala Glu Asn Glu Ala Asp Tyr Tyr Cys Gln Ala Trp Asp Ser Ser
                210                 215                 220

Thr Ala Val Val Phe Gly Gly Gly Thr Lys Leu Thr Val Leu
225                 230                 235

<210> SEQ ID NO 20
<211> LENGTH: 238
<212> TYPE: PRT
<213> ORGANISM: Artificial
<220> FEATURE:
<223> OTHER INFORMATION: Single chain antibody.

<400> SEQUENCE: 20

Gln Val Gln Leu Gln Glu Ser Gly Gly Thr Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Arg Gly Leu Glu Trp Val
            35                  40                  45

Ser Thr Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ala Tyr Ser Gly Ser His Trp Gly Gln Gly Thr Leu Val
                100                 105                 110

Thr Val Ser Ser Gly Gly Gly Ser Gly Gly Gly Ser Gly Gly
        115                 120                 125

Gly Gly Ser Ser Ser Glu Leu Thr Gln Asp Pro Ala Val Ser Val Ala
130                 135                 140

Leu Gly Gln Thr Val Arg Ile Thr Cys Gln Gly Asp Ser Leu Arg Ser
145                 150                 155                 160

Tyr Tyr Ala Ser Trp Tyr Gln Gln Lys Pro Gly Gln Ala Pro Ser Leu
                165                 170                 175

Val Ile Tyr Gly Glu Asn Ser Arg Pro Ser Gly Ile Pro Asp Arg Phe
                180                 185                 190

Ser Gly Ser Ser Ser Gly Asn Thr Ala Ser Leu Thr Ile Thr Gly Ala
                195                 200                 205

Gln Ala Glu Asn Glu Ala Asp Tyr Tyr Cys Gln Ala Trp Asp Ser Ser
                210                 215                 220

Thr Ala Val Val Phe Gly Gly Gly Thr Lys Leu Thr Val Leu
225                 230                 235
```

```
<210> SEQ ID NO 21
<211> LENGTH: 244
<212> TYPE: PRT
<213> ORGANISM: Artificial
<220> FEATURE:
<223> OTHER INFORMATION: Single chain antibody.

<400> SEQUENCE: 21

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Pro Ile Tyr Asp Ser Ser Gly Tyr Asp Ala Phe Asp Ile Trp
            100                 105                 110

Gly Gln Gly Thr Met Val Thr Val Ser Ser Gly Gly Gly Gly Ser Gly
        115                 120                 125

Gly Gly Gly Ser Gly Gly Gly Ser Asp Ile Val Met Thr Gln Ser
    130                 135                 140

Pro Ser Thr Leu Ser Ala Ser Ile Gly Asp Arg Val Thr Ile Thr Cys
145                 150                 155                 160

Arg Ala Ser Glu Gly Ile Tyr His Trp Leu Ala Trp Tyr Gln Gln Lys
                165                 170                 175

Pro Gly Lys Ala Pro Lys Leu Leu Ile Tyr Lys Ala Ser Ser Leu Ala
            180                 185                 190

Ser Gly Ala Pro Ser Arg Phe Ser Gly Ser Gly Ser Gly Thr Asp Phe
        195                 200                 205

Thr Leu Thr Ile Ser Ser Leu Gln Pro Asp Asp Phe Ala Thr Tyr Tyr
    210                 215                 220

Cys Gln Gln Tyr His Thr Ile Ser Arg Thr Phe Gly Pro Gly Thr Lys
225                 230                 235                 240

Val Asp Ile Lys

<210> SEQ ID NO 22
<211> LENGTH: 244
<212> TYPE: PRT
<213> ORGANISM: Artificial
<220> FEATURE:
<223> OTHER INFORMATION: Single chain antibody.

<400> SEQUENCE: 22

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Phe Cys
                 85                  90                  95

Val Arg Pro Ser Asp Ser Gly Trp Ser Phe Glu His Trp Gly Gln Gly
            100                 105                 110

Thr Leu Val Pro Val Ser Ser Gly Gly Gly Ser Gly Gly Gly Gly
        115                 120                 125

Ser Gly Gly Gly Ser Gln Ser Val Leu Thr Gln Pro Pro Ser Ala
130                 135                 140

Ser Gly Thr Pro Gly Gln Arg Val Thr Ile Ser Cys Ser Gly Ser Ser
145                 150                 155                 160

Ser Asn Ile Gly Asn Asn Thr Val Asn Trp Ser Arg Gln Leu Pro Gly
            165                 170                 175

Thr Ala Pro Lys Leu Leu Ile Tyr Ser Asn Asp Gln Arg Pro Ser Gly
            180                 185                 190

Val Pro Asp Arg Phe Ser Gly Ser Lys Ser Gly Thr Ser Ala Ser Leu
            195                 200                 205

Ala Ile Thr Gly Leu Gln Pro Glu Asp Glu Ala Asp Tyr Tyr Cys Gly
210                 215                 220

Thr Trp Asp Ser Ser Leu Ser Ala Tyr Val Phe Gly Thr Gly Thr Lys
225                 230                 235                 240

Leu Thr Val Leu

<210> SEQ ID NO 23
<211> LENGTH: 245
<212> TYPE: PRT
<213> ORGANISM: Artificial
<220> FEATURE:
<223> OTHER INFORMATION: Single chain antibody.

<400> SEQUENCE: 23

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Arg Gly Asp Arg Ser Tyr Gly Ala Glu Tyr Phe Gln His Trp Gly
            100                 105                 110

Gln Gly Thr Leu Val Thr Val Ser Gly Gly Gly Gly Ser Gly Gly
            115                 120                 125

Gly Gly Ser Gly Gly Gly Ser Ser Ser Glu Leu Thr Gln Asp Pro
130                 135                 140

Ala Val Ser Val Ala Ser Gly Gln Thr Val Arg Ile Thr Cys Gln Gly
145                 150                 155                 160

Asp Ser Leu Arg Ser Tyr Tyr Ala Ser Trp Tyr Gln Gln Lys Pro Gly
            165                 170                 175
```

Gln Ala Pro Leu Leu Val Ile Tyr Gly Lys Asn Ile Arg Pro Ser Gly
                180                 185                 190

Ile Pro Asp Arg Phe Ser Gly Ser Thr Ser Gly Asn Ser Ala Ser Leu
            195                 200                 205

Thr Ile Thr Gly Ala Gln Ala Glu Asp Glu Ala Asp Tyr Tyr Cys Asn
        210                 215                 220

Ser Arg Asp Ser Ser Gly Asn Arg Asn Trp Val Phe Gly Gly Gly Thr
225                 230                 235                 240

Lys Leu Thr Val Leu
                245

<210> SEQ ID NO 24
<211> LENGTH: 246
<212> TYPE: PRT
<213> ORGANISM: Artificial
<220> FEATURE:
<223> OTHER INFORMATION: Single chain antibody.

<400> SEQUENCE: 24

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Ser Ser Ser Tyr
            20                  25                  30

Ala Met His Trp Val Arg Gln Ala Pro Gly Lys Gly Leu Glu Tyr Val
        35                  40                  45

Ser Ala Ile Gly Gly Asn Gly Gly Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Glu Gly Glu Gln Trp Leu Glu Tyr Arg Tyr Tyr Tyr Gly Met Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Gly Ser Ser Glu Leu Thr
    130                 135                 140

Gln Asp Pro Ala Val Ser Val Ala Leu Gly Gln Thr Val Arg Ile Thr
145                 150                 155                 160

Cys Gln Gly Asp Ser Leu Arg Ser Tyr Tyr Ala Ser Trp Tyr Gln Gln
                165                 170                 175

Lys Pro Gly Gln Ala Pro Ser Leu Val Ile Tyr Gly Glu Asn Ser Arg
            180                 185                 190

Pro Ser Gly Ile Pro Asp Arg Phe Ser Gly Ser Ser Ser Gly Asn Thr
        195                 200                 205

Ala Ser Leu Thr Ile Thr Gly Ala Gln Ala Glu Asn Glu Ala Asp Tyr
    210                 215                 220

Tyr Cys Gln Ala Trp Asp Ser Ser Thr Ala Val Val Phe Gly Gly Gly
225                 230                 235                 240

Thr Lys Leu Thr Val Leu
                245

<210> SEQ ID NO 25
<211> LENGTH: 250
<212> TYPE: PRT
<213> ORGANISM: Artificial
<220> FEATURE:

<223> OTHER INFORMATION: Single chain antibody.

<400> SEQUENCE: 25

Gln Val Gln Leu Val Glu Ser Gly Gly Val Val Gln Pro Gly Arg
1               5                   10                  15

Ser Leu Arg Leu Ser Cys Thr Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Tyr Ser Ser Asn Trp Phe Ser Tyr Tyr Tyr Tyr
            100                 105                 110

Gly Met Asp Val Trp Gly Gln Gly Thr Thr Val Thr Val Ser Ser Gly
        115                 120                 125

Gly Gly Gly Ser Gly Gly Gly Ser Gly Gly Gly Ser Asn Phe
    130                 135                 140

Met Leu Thr Gln Pro Pro Ser Val Ser Val Ala Pro Gly Lys Thr Ala
145                 150                 155                 160

Arg Ile Thr Cys Gly Gly Asn Asn Ile Gly Ser Lys Ser Val Tyr Trp
                165                 170                 175

Tyr Gln Gln Lys Pro Gly Gln Ala Pro Val Leu Val Val Tyr Asp Asp
            180                 185                 190

Ser Asp Arg Pro Ser Gly Ile Pro Glu Arg Phe Ser Gly Ser Asn Ser
        195                 200                 205

Gly Asn Thr Ala Thr Leu Thr Ile Ser Arg Val Glu Ala Gly Asp Glu
    210                 215                 220

Ala Asp Tyr Tyr Cys Gln Val Trp Asp Ser Ser Ser Asp His Val Val
225                 230                 235                 240

Phe Gly Gly Gly Thr Lys Val Thr Val Leu
                245                 250

<210> SEQ ID NO 26
<211> LENGTH: 30
<212> TYPE: PRT
<213> ORGANISM: Artificial
<220> FEATURE:
<223> OTHER INFORMATION: Domain of single chain antibody

<400> SEQUENCE: 26

Gln Val Gln Leu Gln Glu Ser Gly Gly Gly Leu Val Lys Pro Gly Gly
1               5                   10                  15

Pro Leu Arg Leu Ser Cys Ala Ala Ser Gly Phe Thr Phe Ser
            20                  25                  30

<210> SEQ ID NO 27
<211> LENGTH: 5
<212> TYPE: PRT
<213> ORGANISM: Artificial
<220> FEATURE:
<223> OTHER INFORMATION: Domain of single chain antibody

<400> SEQUENCE: 27

Ser Tyr Gly Met Tyr

```
<210> SEQ ID NO 28
<211> LENGTH: 14
<212> TYPE: PRT
<213> ORGANISM: Artificial
<220> FEATURE:
<223> OTHER INFORMATION: Domain of single chain antibody

<400> SEQUENCE: 28

Trp Val Arg Gln Ala Pro Gly Lys Gly Leu Glu Trp Val Ser
1               5                   10

<210> SEQ ID NO 29
<211> LENGTH: 17
<212> TYPE: PRT
<213> ORGANISM: Artificial
<220> FEATURE:
<223> OTHER INFORMATION: Domain of single chain antibody

<400> SEQUENCE: 29

Thr Leu Ser Arg Ser Gly Ser Gly Thr Tyr Tyr Ala Asp Ser Val Lys
1               5                   10                  15
Gly

<210> SEQ ID NO 30
<211> LENGTH: 32
<212> TYPE: PRT
<213> ORGANISM: Artificial
<220> FEATURE:
<223> OTHER INFORMATION: Domain of single chain antibody

<400> SEQUENCE: 30

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Ser
            20                  25                  30

<210> SEQ ID NO 31
<211> LENGTH: 10
<212> TYPE: PRT
<213> ORGANISM: Artificial
<220> FEATURE:
<223> OTHER INFORMATION: Domain of single chain antibody

<400> SEQUENCE: 31

Ile Ala Val Ala Gly Asn Tyr Phe Asp Tyr
1               5                   10

<210> SEQ ID NO 32
<211> LENGTH: 11
<212> TYPE: PRT
<213> ORGANISM: Artificial
<220> FEATURE:
<223> OTHER INFORMATION: Domain of single chain antibody

<400> SEQUENCE: 32

Trp Gly Gln Gly Thr Leu Val Thr Val Ser Ser
1               5                   10

<210> SEQ ID NO 33
<211> LENGTH: 30
<212> TYPE: PRT
<213> ORGANISM: Artificial
<220> FEATURE:
<223> OTHER INFORMATION: Domain of single chain antibody
```

-continued

```
<400> SEQUENCE: 33

Gln Val Gln Leu Val Gln Ser Gly Gly Val Val Gln Pro Gly Arg
1               5                   10                  15

Ser Leu Arg Leu Ser Cys Ala Ala Thr Gly Ile Pro Phe Ser
            20                  25                  30

<210> SEQ ID NO 34
<211> LENGTH: 5
<212> TYPE: PRT
<213> ORGANISM: Artificial
<220> FEATURE:
<223> OTHER INFORMATION: Domain of single chain antibody

<400> SEQUENCE: 34

Gly Ser Gly Met His
1               5

<210> SEQ ID NO 35
<211> LENGTH: 14
<212> TYPE: PRT
<213> ORGANISM: Artificial
<220> FEATURE:
<223> OTHER INFORMATION: Domain of single chain antibody

<400> SEQUENCE: 35

Trp Val Arg Gln Ala Pro Gly Lys Gly Leu Glu Trp Val Thr
1               5                   10

<210> SEQ ID NO 36
<211> LENGTH: 17
<212> TYPE: PRT
<213> ORGANISM: Artificial
<220> FEATURE:
<223> OTHER INFORMATION: Domain of single chain antibody

<400> SEQUENCE: 36

Met Ile Trp Tyr Asp Gly Ser Asn Lys Phe Tyr Ala Asp Ser Val Lys
1               5                   10                  15

Gly

<210> SEQ ID NO 37
<211> LENGTH: 32
<212> TYPE: PRT
<213> ORGANISM: Artificial
<220> FEATURE:
<223> OTHER INFORMATION: Domain of single chain antibody

<400> SEQUENCE: 37

Arg Phe Thr Ile Ser Arg Asp Asn Ser Lys Asn Thr Leu Tyr Leu Gln
1               5                   10                  15

Met Asp Ser Leu Arg Ala Glu Asp Thr Ala Val Tyr Phe Cys Ala Arg
            20                  25                  30

<210> SEQ ID NO 38
<211> LENGTH: 9
<212> TYPE: PRT
<213> ORGANISM: Artificial
<220> FEATURE:
<223> OTHER INFORMATION: Domain of single chain antibody

<400> SEQUENCE: 38

Asp Lys Gly Val Arg Ser Met Asp Val
1               5
```

```
<210> SEQ ID NO 39
<211> LENGTH: 11
<212> TYPE: PRT
<213> ORGANISM: Artificial
<220> FEATURE:
<223> OTHER INFORMATION: Domain of single chain antibody

<400> SEQUENCE: 39

Trp Gly Leu Gly Thr Thr Val Thr Val Ser Ser
1               5                   10

<210> SEQ ID NO 40
<211> LENGTH: 30
<212> TYPE: PRT
<213> ORGANISM: Artificial
<220> FEATURE:
<223> OTHER INFORMATION: Domain of single chain antibody

<400> SEQUENCE: 40

Gln Val Gln Leu Gln Glu Ser Gly Gly Leu Val Gln Pro Gly Gly
1               5                   10                  15

Ser Leu Arg Leu Ser Cys Ser Ala Ser Gly Phe Thr Phe Gly
            20                  25                  30

<210> SEQ ID NO 41
<211> LENGTH: 5
<212> TYPE: PRT
<213> ORGANISM: Artificial
<220> FEATURE:
<223> OTHER INFORMATION: Domain of single chain antibody

<400> SEQUENCE: 41

Thr Tyr Ala Met Arg
1               5

<210> SEQ ID NO 42
<211> LENGTH: 14
<212> TYPE: PRT
<213> ORGANISM: Artificial
<220> FEATURE:
<223> OTHER INFORMATION: Domain of single chain antibody

<400> SEQUENCE: 42

Trp Val Arg Gln Thr Ser Gly Lys Gly Leu Glu Trp Val Ser
1               5                   10

<210> SEQ ID NO 43
<211> LENGTH: 16
<212> TYPE: PRT
<213> ORGANISM: Artificial
<220> FEATURE:
<223> OTHER INFORMATION: Domain of single chain antibody

<400> SEQUENCE: 43

Gly Ile Gly Val Ser Gly Asp Ala Tyr Tyr Thr Asp Ser Val Arg Gly
1               5                   10                  15

<210> SEQ ID NO 44
<211> LENGTH: 32
<212> TYPE: PRT
<213> ORGANISM: Artificial
<220> FEATURE:
<223> OTHER INFORMATION: Domain of single chain antibody

<400> SEQUENCE: 44

Arg Phe Thr Ile Ser Arg Asp Asn Ser Lys Asn Thr Leu Tyr Leu Gln
```

Met Asn Thr Leu Arg Ala Glu Asp Thr Ala Thr Tyr Tyr Cys Thr Arg
            20                  25                  30

<210> SEQ ID NO 45
<211> LENGTH: 9
<212> TYPE: PRT
<213> ORGANISM: Artificial
<220> FEATURE:
<223> OTHER INFORMATION: Domain of single chain antibody

<400> SEQUENCE: 45

Lys Ser Ser Thr Thr Ser Asn Asp Tyr
1               5

<210> SEQ ID NO 46
<211> LENGTH: 11
<212> TYPE: PRT
<213> ORGANISM: Artificial
<220> FEATURE:
<223> OTHER INFORMATION: Domain of single chain antibody

<400> SEQUENCE: 46

Trp Gly Arg Gly Thr Leu Val Thr Val Ser Ser
1               5                   10

<210> SEQ ID NO 47
<211> LENGTH: 30
<212> TYPE: PRT
<213> ORGANISM: Artificial
<220> FEATURE:
<223> OTHER INFORMATION: Domain of single chain antibody

<400> SEQUENCE: 47

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 48
<211> LENGTH: 5
<212> TYPE: PRT
<213> ORGANISM: Artificial
<220> FEATURE:
<223> OTHER INFORMATION: Domain of single chain antibody

<400> SEQUENCE: 48

Ser Tyr Ala Met His
1               5

<210> SEQ ID NO 49
<211> LENGTH: 14
<212> TYPE: PRT
<213> ORGANISM: Artificial
<220> FEATURE:
<223> OTHER INFORMATION: Domain of single chain antibody

<400> SEQUENCE: 49

Trp Val Arg Gln Ala Pro Gly Lys Gly Leu Glu Trp Val Ala
1               5                   10

<210> SEQ ID NO 50
<211> LENGTH: 17
<212> TYPE: PRT
<213> ORGANISM: Artificial
<220> FEATURE:

<223> OTHER INFORMATION: Domain of single chain antibody

<400> SEQUENCE: 50

Val Ile Ser Tyr Asp Gly Ser Asn Lys Tyr Tyr Ala Asp Ser Val Lys
1               5                   10                  15

Gly

<210> SEQ ID NO 51
<211> LENGTH: 32
<212> TYPE: PRT
<213> ORGANISM: Artificial
<220> FEATURE:
<223> OTHER INFORMATION: Domain of single chain antibody

<400> SEQUENCE: 51

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 52
<211> LENGTH: 10
<212> TYPE: PRT
<213> ORGANISM: Artificial
<220> FEATURE:
<223> OTHER INFORMATION: Domain of single chain antibody

<400> SEQUENCE: 52

Phe Ser Ser Gly Trp Tyr Tyr Phe Asp Tyr
1               5                   10

<210> SEQ ID NO 53
<211> LENGTH: 11
<212> TYPE: PRT
<213> ORGANISM: Artificial
<220> FEATURE:
<223> OTHER INFORMATION: Domain of single chain antibody

<400> SEQUENCE: 53

Trp Gly Gln Gly Thr Leu Val Thr Val Ser Ser
1               5                   10

<210> SEQ ID NO 54
<211> LENGTH: 30
<212> TYPE: PRT
<213> ORGANISM: Artificial
<220> FEATURE:
<223> OTHER INFORMATION: Domain of single chain antibody

<400> SEQUENCE: 54

Gln Val Gln Leu Leu Gln Ser Gly Gly Gly Leu Val Gln Pro Gly Gly
1               5                   10                  15

Ser Leu Arg Leu Ser Cys Ala Ala Ser Gly Phe Thr Phe Ser
                20                  25                  30

<210> SEQ ID NO 55
<211> LENGTH: 5
<212> TYPE: PRT
<213> ORGANISM: Artificial
<220> FEATURE:
<223> OTHER INFORMATION: Domain of single chain antibody

<400> SEQUENCE: 55

Ser Tyr Ala Met Ser
1               5

<210> SEQ ID NO 56
<211> LENGTH: 14
<212> TYPE: PRT
<213> ORGANISM: Artificial
<220> FEATURE:
<223> OTHER INFORMATION: Domain of single chain antibody

<400> SEQUENCE: 56

Trp Val Arg Gln Ala Pro Gly Lys Gly Leu Glu Trp Val Ser
1               5                   10

<210> SEQ ID NO 57
<211> LENGTH: 17
<212> TYPE: PRT
<213> ORGANISM: Artificial
<220> FEATURE:
<223> OTHER INFORMATION: Domain of single chain antibody

<400> SEQUENCE: 57

Ala Ile Ser Gly Ser Gly Gly Ser Thr Tyr Tyr Thr Asp Ser Val Lys
1               5                   10                  15

Gly

<210> SEQ ID NO 58
<211> LENGTH: 32
<212> TYPE: PRT
<213> ORGANISM: Artificial
<220> FEATURE:
<223> OTHER INFORMATION: Domain of single chain antibody

<400> SEQUENCE: 58

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 59
<211> LENGTH: 12
<212> TYPE: PRT
<213> ORGANISM: Artificial
<220> FEATURE:
<223> OTHER INFORMATION: Domain of single chain antibody

<400> SEQUENCE: 59

Ser His Asp Tyr Gly Asp Tyr Ala Gly Phe Asp Tyr
1               5                   10

<210> SEQ ID NO 60
<211> LENGTH: 11
<212> TYPE: PRT
<213> ORGANISM: Artificial
<220> FEATURE:
<223> OTHER INFORMATION: Domain of single chain antibody

<400> SEQUENCE: 60

Trp Gly Gln Gly Thr Leu Val Thr Val Ser Ser
1               5                   10

<210> SEQ ID NO 61
<211> LENGTH: 30
<212> TYPE: PRT
<213> ORGANISM: Artificial
<220> FEATURE:
<223> OTHER INFORMATION: Domain of single chain antibody -continued

```
<400> SEQUENCE: 61

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 62
<211> LENGTH: 5
<212> TYPE: PRT
<213> ORGANISM: Artificial
<220> FEATURE:
<223> OTHER INFORMATION: Domain of single chain antibody

<400> SEQUENCE: 62

Asn Ala Trp Met Asn
1               5

<210> SEQ ID NO 63
<211> LENGTH: 14
<212> TYPE: PRT
<213> ORGANISM: Artificial
<220> FEATURE:
<223> OTHER INFORMATION: Domain of single chain antibody

<400> SEQUENCE: 63

Trp Val Arg Gln Ala Pro Gly Lys Gly Leu Glu Trp Val Gly
1               5                   10

<210> SEQ ID NO 64
<211> LENGTH: 19
<212> TYPE: PRT
<213> ORGANISM: Artificial
<220> FEATURE:
<223> OTHER INFORMATION: Domain of single chain antibody

<400> SEQUENCE: 64

Arg Ile Lys Ser Lys Thr Asp Glu Gly Thr Thr Asp Tyr Ala Ala Pro
1               5                   10                  15

Val Lys Gly

<210> SEQ ID NO 65
<211> LENGTH: 32
<212> TYPE: PRT
<213> ORGANISM: Artificial
<220> FEATURE:
<223> OTHER INFORMATION: Domain of single chain antibody

<400> SEQUENCE: 65

Arg Phe Ser Ile Ser Arg Asp Asp Ser Lys Asn Thr Leu Tyr Leu Gln
1               5                   10                  15

Met Asn Ser Leu Lys Thr Glu Asp Thr Gly Val Tyr Tyr Cys Thr Ala
            20                  25                  30

<210> SEQ ID NO 66
<211> LENGTH: 8
<212> TYPE: PRT
<213> ORGANISM: Artificial
<220> FEATURE:
<223> OTHER INFORMATION: Domain of single chain antibody

<400> SEQUENCE: 66

Thr Lys Gly Leu Gly Gly Ser Lys
1               5
```

```
<210> SEQ ID NO 67
<211> LENGTH: 11
<212> TYPE: PRT
<213> ORGANISM: Artificial
<220> FEATURE:
<223> OTHER INFORMATION: Domain of single chain antibody

<400> SEQUENCE: 67

Leu Gly Gln Gly Thr Leu Val Thr Val Ser Ser
1               5                   10

<210> SEQ ID NO 68
<211> LENGTH: 30
<212> TYPE: PRT
<213> ORGANISM: Artificial
<220> FEATURE:
<223> OTHER INFORMATION: Domain of single chain antibody

<400> SEQUENCE: 68

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 69
<211> LENGTH: 5
<212> TYPE: PRT
<213> ORGANISM: Artificial
<220> FEATURE:
<223> OTHER INFORMATION: Domain of single chain antibody

<400> SEQUENCE: 69

Ser Phe Gly Met His
1               5

<210> SEQ ID NO 70
<211> LENGTH: 14
<212> TYPE: PRT
<213> ORGANISM: Artificial
<220> FEATURE:
<223> OTHER INFORMATION: Domain of single chain antibody

<400> SEQUENCE: 70

Trp Val Arg Arg Ala Pro Gly Lys Gly Leu Glu Trp Val Ala
1               5                   10

<210> SEQ ID NO 71
<211> LENGTH: 17
<212> TYPE: PRT
<213> ORGANISM: Artificial
<220> FEATURE:
<223> OTHER INFORMATION: Domain of single chain antibody

<400> SEQUENCE: 71

Val Ile Ser Tyr Asp Gly Ser Asn Gln Tyr Tyr Ala Asp Ser Val Lys
1               5                   10                  15

Gly

<210> SEQ ID NO 72
<211> LENGTH: 32
<212> TYPE: PRT
<213> ORGANISM: Artificial
<220> FEATURE:
<223> OTHER INFORMATION: Domain of single chain antibody

<400> SEQUENCE: 72
```

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Gly Ser
            20                  25                  30
```

<210> SEQ ID NO 73
<211> LENGTH: 14
<212> TYPE: PRT
<213> ORGANISM: Artificial
<220> FEATURE:
<223> OTHER INFORMATION: Domain of single chain antibody

<400> SEQUENCE: 73

```
Arg Pro Gly Gly Gly Tyr Ala Ser Gly Ser Thr Val Ala Tyr
1               5                   10
```

<210> SEQ ID NO 74
<211> LENGTH: 11
<212> TYPE: PRT
<213> ORGANISM: Artificial
<220> FEATURE:
<223> OTHER INFORMATION: Domain of single chain antibody

<400> SEQUENCE: 74

```
Trp Gly Gln Gly Thr Pro Val Thr Val Ser Ser
1               5                   10
```

<210> SEQ ID NO 75
<211> LENGTH: 30
<212> TYPE: PRT
<213> ORGANISM: Artificial
<220> FEATURE:
<223> OTHER INFORMATION: Domain of single chain antibody

<400> SEQUENCE: 75

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30
```

<210> SEQ ID NO 76
<211> LENGTH: 5
<212> TYPE: PRT
<213> ORGANISM: Artificial
<220> FEATURE:
<223> OTHER INFORMATION: Domain of single chain antibody

<400> SEQUENCE: 76

```
Ser Tyr Ala Met Gly
1               5
```

<210> SEQ ID NO 77
<211> LENGTH: 14
<212> TYPE: PRT
<213> ORGANISM: Artificial
<220> FEATURE:
<223> OTHER INFORMATION: Domain of single chain antibody

<400> SEQUENCE: 77

```
Trp Val Arg Gln Ala Pro Gly Lys Gly Leu Glu Trp Val Ser
1               5                   10
```

<210> SEQ ID NO 78
<211> LENGTH: 17
<212> TYPE: PRT
<213> ORGANISM: Artificial

```
<220> FEATURE:
<223> OTHER INFORMATION: Domain of single chain antibody

<400> SEQUENCE: 78

Ala Ile Ser Gly Ser Gly Gly Ser Thr Tyr Tyr Ala Asp Ser Val Lys
1               5                   10                  15

Gly

<210> SEQ ID NO 79
<211> LENGTH: 32
<212> TYPE: PRT
<213> ORGANISM: Artificial
<220> FEATURE:
<223> OTHER INFORMATION: Domain of single chain antibody

<400> SEQUENCE: 79

Arg Phe Thr Ile Ser Arg Asp Asn Ser Lys Asp Thr Leu Tyr Leu Gln
1               5                   10                  15

Met Asn Ser Leu Arg Ala Glu Asp Thr Ala Val Tyr Tyr Cys Ala Ser
                20                  25                  30

<210> SEQ ID NO 80
<211> LENGTH: 6
<212> TYPE: PRT
<213> ORGANISM: Artificial
<220> FEATURE:
<223> OTHER INFORMATION: Domain of single chain antibody

<400> SEQUENCE: 80

Arg Ser Leu Leu Asp Tyr
1               5

<210> SEQ ID NO 81
<211> LENGTH: 11
<212> TYPE: PRT
<213> ORGANISM: Artificial
<220> FEATURE:
<223> OTHER INFORMATION: Domain of single chain antibody

<400> SEQUENCE: 81

Trp Gly Gln Gly Thr Leu Val Thr Val Ser Ser
1               5                   10

<210> SEQ ID NO 82
<211> LENGTH: 30
<212> TYPE: PRT
<213> ORGANISM: Artificial
<220> FEATURE:
<223> OTHER INFORMATION: Domain of single chain antibody

<400> SEQUENCE: 82

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
                20                  25                  30

<210> SEQ ID NO 83
<211> LENGTH: 5
<212> TYPE: PRT
<213> ORGANISM: Artificial
<220> FEATURE:
<223> OTHER INFORMATION: Domain of single chain antibody

<400> SEQUENCE: 83

Ser Tyr Ala Met Ser
```

<210> SEQ ID NO 84
<211> LENGTH: 14
<212> TYPE: PRT
<213> ORGANISM: Artificial
<220> FEATURE:
<223> OTHER INFORMATION: Domain of single chain antibody

<400> SEQUENCE: 84

Trp Val Arg Gln Ala Pro Gly Lys Gly Leu Glu Trp Val Ser
1               5                   10

<210> SEQ ID NO 85
<211> LENGTH: 17
<212> TYPE: PRT
<213> ORGANISM: Artificial
<220> FEATURE:
<223> OTHER INFORMATION: Domain of single chain antibody

<400> SEQUENCE: 85

Ala Ile Ser Gly Ser Gly Gly Ser Thr Tyr Tyr Ala Asp Ser Val Lys
1               5                   10                  15

Gly

<210> SEQ ID NO 86
<211> LENGTH: 32
<212> TYPE: PRT
<213> ORGANISM: Artificial
<220> FEATURE:
<223> OTHER INFORMATION: Domain of single chain antibody

<400> SEQUENCE: 86

Arg Phe Thr Ile Ser Arg Asp Asn Ser Lys Asp Thr Leu Tyr Leu Gln
1               5                   10                  15

Met Asn Ser Leu Arg Ala Glu Asp Thr Ala Val Tyr Tyr Cys Ala Ser
            20                  25                  30

<210> SEQ ID NO 87
<211> LENGTH: 6
<212> TYPE: PRT
<213> ORGANISM: Artificial
<220> FEATURE:
<223> OTHER INFORMATION: Domain of single chain antibody

<400> SEQUENCE: 87

Arg Ser Leu Leu Asp Tyr
1               5

<210> SEQ ID NO 88
<211> LENGTH: 11
<212> TYPE: PRT
<213> ORGANISM: Artificial
<220> FEATURE:
<223> OTHER INFORMATION: Domain of single chain antibody

<400> SEQUENCE: 88

Trp Gly Gln Gly Thr Leu Val Thr Val Ser Ser
1               5                   10

<210> SEQ ID NO 89
<211> LENGTH: 30
<212> TYPE: PRT
<213> ORGANISM: Artificial
<220> FEATURE:
<223> OTHER INFORMATION: Domain of single chain antibody

```
<400> SEQUENCE: 89

Gln Val Gln Leu Gln Glu Ser Gly Gly Gly Leu Val Gln Leu Gly Gly
1               5                   10                  15

Ser Leu Arg Leu Ser Cys Ala Ala Ser Gly Phe Thr Phe Ser
            20                  25                  30

<210> SEQ ID NO 90
<211> LENGTH: 5
<212> TYPE: PRT
<213> ORGANISM: Artificial
<220> FEATURE:
<223> OTHER INFORMATION: Domain of single chain antibody

<400> SEQUENCE: 90

Ser Tyr Ala Met Ser
1               5

<210> SEQ ID NO 91
<211> LENGTH: 14
<212> TYPE: PRT
<213> ORGANISM: Artificial
<220> FEATURE:
<223> OTHER INFORMATION: Domain of single chain antibody

<400> SEQUENCE: 91

Trp Val Arg Gln Ala Pro Gly Lys Gly Leu Glu Trp Val Ser
1               5                   10

<210> SEQ ID NO 92
<211> LENGTH: 17
<212> TYPE: PRT
<213> ORGANISM: Artificial
<220> FEATURE:
<223> OTHER INFORMATION: Domain of single chain antibody

<400> SEQUENCE: 92

Ala Ile Ser Gly Ser Gly Gly Ser Thr Tyr Tyr Ala Asp Ser Val Lys
1               5                   10                  15

Gly

<210> SEQ ID NO 93
<211> LENGTH: 32
<212> TYPE: PRT
<213> ORGANISM: Artificial
<220> FEATURE:
<223> OTHER INFORMATION: Domain of single chain antibody

<400> SEQUENCE: 93

Arg Phe Thr Ile Ser Arg Asp Asn Ser Lys Asn Thr Leu Tyr Leu Gln
1               5                   10                  15

Met Ser Ser Leu Arg Ala Glu Asp Thr Ala Phe Tyr Tyr Cys Ala Asn
            20                  25                  30

<210> SEQ ID NO 94
<211> LENGTH: 10
<212> TYPE: PRT
<213> ORGANISM: Artificial
<220> FEATURE:
<223> OTHER INFORMATION: Domain of single chain antibody

<400> SEQUENCE: 94

Ser Ala Tyr Thr Gly Gly Trp Tyr Asp Tyr
1               5                   10
```

<210> SEQ ID NO 95
<211> LENGTH: 11
<212> TYPE: PRT
<213> ORGANISM: Artificial
<220> FEATURE:
<223> OTHER INFORMATION: Domain of single chain antibody

<400> SEQUENCE: 95

Trp Gly His Gly Thr Leu Val Thr Val Ser Ser
1               5                   10

<210> SEQ ID NO 96
<211> LENGTH: 30
<212> TYPE: PRT
<213> ORGANISM: Artificial
<220> FEATURE:
<223> OTHER INFORMATION: Domain of single chain antibody

<400> SEQUENCE: 96

Gln Val Asn Leu Arg Glu Ser Gly Gly Leu Val Gln Pro Gly Gly
1               5                   10                  15

Phe Leu Arg Leu Ser Cys Ala Ala Phe Gly Phe Thr Phe Ser
            20                  25                  30

<210> SEQ ID NO 97
<211> LENGTH: 5
<212> TYPE: PRT
<213> ORGANISM: Artificial
<220> FEATURE:
<223> OTHER INFORMATION: Domain of single chain antibody

<400> SEQUENCE: 97

Gly Tyr Trp Met Ser
1               5

<210> SEQ ID NO 98
<211> LENGTH: 14
<212> TYPE: PRT
<213> ORGANISM: Artificial
<220> FEATURE:
<223> OTHER INFORMATION: Domain of single chain antibody

<400> SEQUENCE: 98

Trp Val His Pro Ala Pro Gly Lys Gly Leu Glu Trp Val Ala
1               5                   10

<210> SEQ ID NO 99
<211> LENGTH: 17
<212> TYPE: PRT
<213> ORGANISM: Artificial
<220> FEATURE:
<223> OTHER INFORMATION: Domain of single chain antibody

<400> SEQUENCE: 99

Asn Ile Lys Gln Asp Gly Ser Glu Lys Phe Tyr Val Asp Ser Val Lys
1               5                   10                  15

Gly

<210> SEQ ID NO 100
<211> LENGTH: 32
<212> TYPE: PRT
<213> ORGANISM: Artificial
<220> FEATURE:
<223> OTHER INFORMATION: Domain of single chain antibody

<400> SEQUENCE: 100

```
Arg Phe Thr Ile Ser Arg Asp Asn Ala Lys Asn Ser Leu Phe Leu Gln
1               5                   10                  15

Met Asn Ser Leu Arg Ala Glu Asp Thr Ala Val Tyr Phe Cys Ala Arg
            20                  25                  30

<210> SEQ ID NO 101
<211> LENGTH: 6
<212> TYPE: PRT
<213> ORGANISM: Artificial
<220> FEATURE:
<223> OTHER INFORMATION: Domain of single chain antibody

<400> SEQUENCE: 101

Gly Leu Leu Ser Asp Tyr
1               5

<210> SEQ ID NO 102
<211> LENGTH: 11
<212> TYPE: PRT
<213> ORGANISM: Artificial
<220> FEATURE:
<223> OTHER INFORMATION: Domain of single chain antibody

<400> SEQUENCE: 102

Trp Gly Gln Gly Thr Leu Val Pro Val Ser Ser
1               5                   10

<210> SEQ ID NO 103
<211> LENGTH: 30
<212> TYPE: PRT
<213> ORGANISM: Artificial
<220> FEATURE:
<223> OTHER INFORMATION: Domain of single chain antibody

<400> SEQUENCE: 103

Gln Val Gln Leu Gln Glu Ser Gly Gly Leu Val Lys Pro Gly Gly
1               5                   10                  15

Pro Leu Arg Leu Ser Cys Ala Ala Ser Gly Phe Thr Phe Ser
            20                  25                  30

<210> SEQ ID NO 104
<211> LENGTH: 5
<212> TYPE: PRT
<213> ORGANISM: Artificial
<220> FEATURE:
<223> OTHER INFORMATION: Domain of single chain antibody

<400> SEQUENCE: 104

Ser Tyr Gly Met Tyr
1               5

<210> SEQ ID NO 105
<211> LENGTH: 14
<212> TYPE: PRT
<213> ORGANISM: Artificial
<220> FEATURE:
<223> OTHER INFORMATION: Domain of single chain antibody

<400> SEQUENCE: 105

Trp Val Arg Gln Ala Pro Gly Lys Gly Leu Glu Trp Val Ser
1               5                   10

<210> SEQ ID NO 106
<211> LENGTH: 17
<212> TYPE: PRT
```

```
<213> ORGANISM: Artificial
<220> FEATURE:
<223> OTHER INFORMATION: Domain of single chain antibody

<400> SEQUENCE: 106

Thr Leu Ser Arg Ser Gly Ser Gly Thr Tyr Tyr Ala Glu Ser Val Lys
1               5                   10                  15

Gly

<210> SEQ ID NO 107
<211> LENGTH: 32
<212> TYPE: PRT
<213> ORGANISM: Artificial
<220> FEATURE:
<223> OTHER INFORMATION: Domain of single chain antibody

<400> SEQUENCE: 107

Arg Phe Thr Ile Ser Arg Asp Asn Ser Lys Asn Thr Leu Tyr Phe Gln
1               5                   10                  15

Met Asn Ser Leu Arg Ala Glu Asp Thr Ala Val Tyr Tyr Cys Ala Ser
            20                  25                  30

<210> SEQ ID NO 108
<211> LENGTH: 10
<212> TYPE: PRT
<213> ORGANISM: Artificial
<220> FEATURE:
<223> OTHER INFORMATION: Domain of single chain antibody

<400> SEQUENCE: 108

Ile Ala Val Ala Gly Asn Tyr Phe Glu Tyr
1               5                   10

<210> SEQ ID NO 109
<211> LENGTH: 11
<212> TYPE: PRT
<213> ORGANISM: Artificial
<220> FEATURE:
<223> OTHER INFORMATION: Domain of single chain antibody

<400> SEQUENCE: 109

Trp Gly Gln Gly Thr Leu Val Thr Val Ser Ser
1               5                   10

<210> SEQ ID NO 110
<211> LENGTH: 30
<212> TYPE: PRT
<213> ORGANISM: Artificial
<220> FEATURE:
<223> OTHER INFORMATION: Domain of single chain antibody

<400> SEQUENCE: 110

Gln Val Gln Leu Gln Glu Ser Gly Gly Gly Leu Val Lys Pro Gly Glu
1               5                   10                  15

Ser Leu Arg Leu Ser Cys Ala Ala Ser Gly Phe Thr Phe Ser
            20                  25                  30

<210> SEQ ID NO 111
<211> LENGTH: 5
<212> TYPE: PRT
<213> ORGANISM: Artificial
<220> FEATURE:
<223> OTHER INFORMATION: Domain of single chain antibody

<400> SEQUENCE: 111
```

Asp His Tyr Met Asp
1               5

<210> SEQ ID NO 112
<211> LENGTH: 14
<212> TYPE: PRT
<213> ORGANISM: Artificial
<220> FEATURE:
<223> OTHER INFORMATION: Domain of single chain antibody

<400> SEQUENCE: 112

Trp Val Arg Gln Ala Pro Gly Lys Gly Leu Glu Trp Val Ala
1               5                   10

<210> SEQ ID NO 113
<211> LENGTH: 17
<212> TYPE: PRT
<213> ORGANISM: Artificial
<220> FEATURE:
<223> OTHER INFORMATION: Domain of single chain antibody

<400> SEQUENCE: 113

Tyr Ile Arg Tyr Asp Gly Ser Thr Lys Tyr Tyr Ala Asp Ser Val Lys
1               5                   10                  15

Gly

<210> SEQ ID NO 114
<211> LENGTH: 32
<212> TYPE: PRT
<213> ORGANISM: Artificial
<220> FEATURE:
<223> OTHER INFORMATION: Domain of single chain antibody

<400> SEQUENCE: 114

Arg Phe Thr Ile Ser Arg Asp Asn Ser Lys Asn Thr Leu Tyr Leu Gln
1               5                   10                  15

Met Asn Ser Leu Arg Pro Glu Asp Thr Ala Phe Tyr Tyr Cys Ala Arg
            20                  25                  30

<210> SEQ ID NO 115
<211> LENGTH: 11
<212> TYPE: PRT
<213> ORGANISM: Artificial
<220> FEATURE:
<223> OTHER INFORMATION: Domain of single chain antibody

<400> SEQUENCE: 115

Leu Ile Ala Glu Ala Glu Gly Trp Phe Asp Pro
1               5                   10

<210> SEQ ID NO 116
<211> LENGTH: 11
<212> TYPE: PRT
<213> ORGANISM: Artificial
<220> FEATURE:
<223> OTHER INFORMATION: Domain of single chain antibody

<400> SEQUENCE: 116

Trp Gly Gln Gly Thr Leu Val Thr Val Ser Ser
1               5                   10

<210> SEQ ID NO 117
<211> LENGTH: 30
<212> TYPE: PRT
<213> ORGANISM: Artificial
<220> FEATURE:

<223> OTHER INFORMATION: Domain of single chain antibody

<400> SEQUENCE: 117

Gln Val Gln Leu Leu Gln Ser Ala Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 118
<211> LENGTH: 5
<212> TYPE: PRT
<213> ORGANISM: Artificial
<220> FEATURE:
<223> OTHER INFORMATION: Domain of single chain antibody

<400> SEQUENCE: 118

Thr Tyr Ala Met Asn
1               5

<210> SEQ ID NO 119
<211> LENGTH: 14
<212> TYPE: PRT
<213> ORGANISM: Artificial
<220> FEATURE:
<223> OTHER INFORMATION: Domain of single chain antibody

<400> SEQUENCE: 119

Trp Val Arg Gln Ala Pro Gly Lys Gly Leu Glu Trp Val Ser
1               5                   10

<210> SEQ ID NO 120
<211> LENGTH: 17
<212> TYPE: PRT
<213> ORGANISM: Artificial
<220> FEATURE:
<223> OTHER INFORMATION: Domain of single chain antibody

<400> SEQUENCE: 120

Gly Ile Ser Gly Ser Gly Gly Ser Thr Asn Tyr Ala Asp Ser Val Lys
1               5                   10                  15

Gly

<210> SEQ ID NO 121
<211> LENGTH: 32
<212> TYPE: PRT
<213> ORGANISM: Artificial
<220> FEATURE:
<223> OTHER INFORMATION: Domain of single chain antibody

<400> SEQUENCE: 121

Arg Phe Thr Ile Ser Arg Asp Ser Ser Lys Asn Thr Leu Phe Leu Gln
1               5                   10                  15

Met Asn Ser Leu Arg Ala Glu Asp Thr Ala Val Tyr Tyr Cys Ala Lys
            20                  25                  30

<210> SEQ ID NO 122
<211> LENGTH: 9
<212> TYPE: PRT
<213> ORGANISM: Artificial
<220> FEATURE:
<223> OTHER INFORMATION: Domain of single chain antibody

<400> SEQUENCE: 122

Asp Tyr Gly Ser Gly Trp Tyr Asp Tyr
1               5

<210> SEQ ID NO 123
<211> LENGTH: 11
<212> TYPE: PRT
<213> ORGANISM: Artificial
<220> FEATURE:
<223> OTHER INFORMATION: Domain of single chain antibody

<400> SEQUENCE: 123

Trp Gly Gln Gly Thr Leu Val Thr Val Ser Ser
1               5                   10

<210> SEQ ID NO 124
<211> LENGTH: 30
<212> TYPE: PRT
<213> ORGANISM: Artificial
<220> FEATURE:
<223> OTHER INFORMATION: Domain of single chain antibody

<400> SEQUENCE: 124

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 125
<211> LENGTH: 5
<212> TYPE: PRT
<213> ORGANISM: Artificial
<220> FEATURE:
<223> OTHER INFORMATION: Domain of single chain antibody

<400> SEQUENCE: 125

Ser Tyr Ala Met Ser
1               5

<210> SEQ ID NO 126
<211> LENGTH: 14
<212> TYPE: PRT
<213> ORGANISM: Artificial
<220> FEATURE:
<223> OTHER INFORMATION: Domain of single chain antibody

<400> SEQUENCE: 126

Trp Val His Gln Ala Pro Gly Lys Gly Leu Glu Trp Val Ser
1               5                   10

<210> SEQ ID NO 127
<211> LENGTH: 17
<212> TYPE: PRT
<213> ORGANISM: Artificial
<220> FEATURE:
<223> OTHER INFORMATION: Domain of single chain antibody

<400> SEQUENCE: 127

Ala Ile Ser Gly Ser Gly Gly Ser Thr Tyr Tyr Ala Asp Ser Val Lys
1               5                   10                  15

Gly

<210> SEQ ID NO 128
<211> LENGTH: 32
<212> TYPE: PRT
<213> ORGANISM: Artificial
<220> FEATURE:
<223> OTHER INFORMATION: Domain of single chain antibody -continued

<400> SEQUENCE: 128

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
                20                  25                  30

<210> SEQ ID NO 129
<211> LENGTH: 12
<212> TYPE: PRT
<213> ORGANISM: Artificial
<220> FEATURE:
<223> OTHER INFORMATION: Domain of single chain antibody

<400> SEQUENCE: 129

Thr Tyr Tyr Gly Phe Trp Ser Gly Tyr Tyr Asp Tyr
1               5                   10

<210> SEQ ID NO 130
<211> LENGTH: 11
<212> TYPE: PRT
<213> ORGANISM: Artificial
<220> FEATURE:
<223> OTHER INFORMATION: Domain of single chain antibody

<400> SEQUENCE: 130

Leu Gly Gln Gly Thr Leu Val Thr Val Ser Ser
1               5                   10

<210> SEQ ID NO 131
<211> LENGTH: 30
<212> TYPE: PRT
<213> ORGANISM: Artificial
<220> FEATURE:
<223> OTHER INFORMATION: Domain of single chain antibody

<400> SEQUENCE: 131

Gln Val Gln Leu Leu Glu Ser Gly Gly Val Val Gln Pro Gly Thr
1               5                   10                  15

Ser Leu Arg Leu Ser Cys Ala Ala Ser Gly Phe Thr Phe Ser
                20                  25                  30

<210> SEQ ID NO 132
<211> LENGTH: 5
<212> TYPE: PRT
<213> ORGANISM: Artificial
<220> FEATURE:
<223> OTHER INFORMATION: Domain of single chain antibody

<400> SEQUENCE: 132

Asn Tyr Ala Ile Asn
1               5

<210> SEQ ID NO 133
<211> LENGTH: 14
<212> TYPE: PRT
<213> ORGANISM: Artificial
<220> FEATURE:
<223> OTHER INFORMATION: Domain of single chain antibody

<400> SEQUENCE: 133

Trp Val Arg Gln Ala Ala Gly Lys Gly Leu Glu Trp Val Ser
1               5                   10

<210> SEQ ID NO 134
<211> LENGTH: 17

```
<212> TYPE: PRT
<213> ORGANISM: Artificial
<220> FEATURE:
<223> OTHER INFORMATION: Domain of single chain antibody

<400> SEQUENCE: 134

Gly Ile Ser Gly Ser Gly Val Ser Thr Ser Tyr Ala Asp Ser Val Lys
1               5                   10                  15

Gly

<210> SEQ ID NO 135
<211> LENGTH: 32
<212> TYPE: PRT
<213> ORGANISM: Artificial
<220> FEATURE:
<223> OTHER INFORMATION: Domain of single chain antibody

<400> SEQUENCE: 135

Arg Phe Thr Val Ser Arg Asp Asn Ser Lys Asn Thr Leu Tyr Leu Gln
1               5                   10                  15

Met Asn Ser Leu Arg Val Glu Asp Thr Ala Leu Tyr Tyr Cys Ala Lys
            20                  25                  30

<210> SEQ ID NO 136
<211> LENGTH: 10
<212> TYPE: PRT
<213> ORGANISM: Artificial
<220> FEATURE:
<223> OTHER INFORMATION: Domain of single chain antibody

<400> SEQUENCE: 136

Asn Gly Gly Gly Pro Glu Tyr Leu Gln His
1               5                   10

<210> SEQ ID NO 137
<211> LENGTH: 11
<212> TYPE: PRT
<213> ORGANISM: Artificial
<220> FEATURE:
<223> OTHER INFORMATION: Domain of single chain antibody

<400> SEQUENCE: 137

Trp Gly Gln Gly Thr Leu Val Thr Val Ser Ser
1               5                   10

<210> SEQ ID NO 138
<211> LENGTH: 30
<212> TYPE: PRT
<213> ORGANISM: Artificial
<220> FEATURE:
<223> OTHER INFORMATION: Domain of single chain antibody

<400> SEQUENCE: 138

Gln Val Gln Leu Gln Glu Ser Gly Gly Thr Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 139
<211> LENGTH: 5
<212> TYPE: PRT
<213> ORGANISM: Artificial
<220> FEATURE:
<223> OTHER INFORMATION: Domain of single chain antibody

<400> SEQUENCE: 139
```

Ser Tyr Ala Met Ser
1               5

<210> SEQ ID NO 140
<211> LENGTH: 14
<212> TYPE: PRT
<213> ORGANISM: Artificial
<220> FEATURE:
<223> OTHER INFORMATION: Domain of single chain antibody

<400> SEQUENCE: 140

Trp Val Arg Gln Ala Pro Gly Arg Gly Leu Glu Trp Val Ser
1               5                   10

<210> SEQ ID NO 141
<211> LENGTH: 17
<212> TYPE: PRT
<213> ORGANISM: Artificial
<220> FEATURE:
<223> OTHER INFORMATION: Domain of single chain antibody

<400> SEQUENCE: 141

Thr Ile Ser Gly Ser Gly Gly Ser Thr Tyr Tyr Ala Asp Ser Val Lys
1               5                   10                  15

Gly

<210> SEQ ID NO 142
<211> LENGTH: 32
<212> TYPE: PRT
<213> ORGANISM: Artificial
<220> FEATURE:
<223> OTHER INFORMATION: Domain of single chain antibody

<400> SEQUENCE: 142

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
                20                  25                  30

<210> SEQ ID NO 143
<211> LENGTH: 7
<212> TYPE: PRT
<213> ORGANISM: Artificial
<220> FEATURE:
<223> OTHER INFORMATION: Domain of single chain antibody

<400> SEQUENCE: 143

Gly Ala Tyr Ser Gly Ser Tyr
1               5

<210> SEQ ID NO 144
<211> LENGTH: 11
<212> TYPE: PRT
<213> ORGANISM: Artificial
<220> FEATURE:
<223> OTHER INFORMATION: Domain of single chain antibody

<400> SEQUENCE: 144

Trp Gly Gln Gly Thr Leu Val Thr Val Ser Ser
1               5                   10

<210> SEQ ID NO 145
<211> LENGTH: 30
<212> TYPE: PRT
<213> ORGANISM: Artificial

<220> FEATURE:
<223> OTHER INFORMATION: Domain of single chain antibody

<400> SEQUENCE: 145

Gln Val Gln Leu Gln Glu Ser Gly Gly Thr Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 146
<211> LENGTH: 5
<212> TYPE: PRT
<213> ORGANISM: Artificial
<220> FEATURE:
<223> OTHER INFORMATION: Domain of single chain antibody

<400> SEQUENCE: 146

Ser Tyr Ala Met Ser
1               5

<210> SEQ ID NO 147
<211> LENGTH: 14
<212> TYPE: PRT
<213> ORGANISM: Artificial
<220> FEATURE:
<223> OTHER INFORMATION: Domain of single chain antibody

<400> SEQUENCE: 147

Trp Val Arg Gln Ala Pro Gly Arg Gly Leu Glu Trp Val Ser
1               5                   10

<210> SEQ ID NO 148
<211> LENGTH: 17
<212> TYPE: PRT
<213> ORGANISM: Artificial
<220> FEATURE:
<223> OTHER INFORMATION: Domain of single chain antibody

<400> SEQUENCE: 148

Thr Ile Ser Gly Ser Gly Gly Ser Thr Tyr Tyr Ala Asp Ser Val Lys
1               5                   10                  15

Gly

<210> SEQ ID NO 149
<211> LENGTH: 32
<212> TYPE: PRT
<213> ORGANISM: Artificial
<220> FEATURE:
<223> OTHER INFORMATION: Domain of single chain antibody

<400> SEQUENCE: 149

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 150
<211> LENGTH: 7
<212> TYPE: PRT
<213> ORGANISM: Artificial
<220> FEATURE:
<223> OTHER INFORMATION: Domain of single chain antibody

<400> SEQUENCE: 150

Gly Ala Tyr Ser Gly Ser His

<210> SEQ ID NO 151
<211> LENGTH: 11
<212> TYPE: PRT
<213> ORGANISM: Artificial
<220> FEATURE:
<223> OTHER INFORMATION: Domain of single chain antibody

<400> SEQUENCE: 151

Trp Gly Gln Gly Thr Leu Val Thr Val Ser Ser
1               5                   10

<210> SEQ ID NO 152
<211> LENGTH: 30
<212> TYPE: PRT
<213> ORGANISM: Artificial
<220> FEATURE:
<223> OTHER INFORMATION: Domain of single chain antibody

<400> SEQUENCE: 152

Gln Val Gln Leu Val Glu Ser Gly Ala Glu Val Lys Lys Pro Gly Ala
1               5                   10                  15
Ser Val Lys Val Ser Cys Lys Ala Ser Gly Tyr Thr Phe Thr
            20                  25                  30

<210> SEQ ID NO 153
<211> LENGTH: 5
<212> TYPE: PRT
<213> ORGANISM: Artificial
<220> FEATURE:
<223> OTHER INFORMATION: Domain of single chain antibody

<400> SEQUENCE: 153

Ser Tyr Gly Ile Ser
1               5

<210> SEQ ID NO 154
<211> LENGTH: 14
<212> TYPE: PRT
<213> ORGANISM: Artificial
<220> FEATURE:
<223> OTHER INFORMATION: Domain of single chain antibody

<400> SEQUENCE: 154

Trp Val Arg Gln Ala Pro Gly Gln Gly Leu Glu Trp Met Gly
1               5                   10

<210> SEQ ID NO 155
<211> LENGTH: 17
<212> TYPE: PRT
<213> ORGANISM: Artificial
<220> FEATURE:
<223> OTHER INFORMATION: Domain of single chain antibody

<400> SEQUENCE: 155

Trp Ile Ser Ala Tyr Asn Gly Asn Thr Asn Tyr Ala Gln Lys Leu Gln
1               5                   10                  15
Gly

<210> SEQ ID NO 156
<211> LENGTH: 32
<212> TYPE: PRT
<213> ORGANISM: Artificial
<220> FEATURE:
<223> OTHER INFORMATION: Domain of single chain antibody

<400> SEQUENCE: 156

Arg Val Thr Met Thr Thr Asp Thr Ser Thr Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 157
<211> LENGTH: 13
<212> TYPE: PRT
<213> ORGANISM: Artificial
<220> FEATURE:
<223> OTHER INFORMATION: Domain of single chain antibody

<400> SEQUENCE: 157

Pro Ile Tyr Asp Ser Ser Gly Tyr Asp Ala Phe Asp Ile
1               5                   10

<210> SEQ ID NO 158
<211> LENGTH: 11
<212> TYPE: PRT
<213> ORGANISM: Artificial
<220> FEATURE:
<223> OTHER INFORMATION: Domain of single chain antibody

<400> SEQUENCE: 158

Trp Gly Gln Gly Thr Met Val Thr Val Ser Ser
1               5                   10

<210> SEQ ID NO 159
<211> LENGTH: 30
<212> TYPE: PRT
<213> ORGANISM: Artificial
<220> FEATURE:
<223> OTHER INFORMATION: Domain of single chain antibody

<400> SEQUENCE: 159

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 160
<211> LENGTH: 5
<212> TYPE: PRT
<213> ORGANISM: Artificial
<220> FEATURE:
<223> OTHER INFORMATION: Domain of single chain antibody

<400> SEQUENCE: 160

Ser Tyr Ala Met His
1               5

<210> SEQ ID NO 161
<211> LENGTH: 14
<212> TYPE: PRT
<213> ORGANISM: Artificial
<220> FEATURE:
<223> OTHER INFORMATION: Domain of single chain antibody

<400> SEQUENCE: 161

Trp Val Arg Gln Ala Pro Gly Lys Gly Leu Glu Trp Val Ala
1               5                   10

<210> SEQ ID NO 162

```
<211> LENGTH: 17
<212> TYPE: PRT
<213> ORGANISM: Artificial
<220> FEATURE:
<223> OTHER INFORMATION: Domain of single chain antibody

<400> SEQUENCE: 162

Val Ile Ser Tyr Asp Gly Ser Asn Lys Tyr Tyr Ala Asp Ser Val Lys
1               5                   10                  15
Gly

<210> SEQ ID NO 163
<211> LENGTH: 32
<212> TYPE: PRT
<213> ORGANISM: Artificial
<220> FEATURE:
<223> OTHER INFORMATION: Domain of single chain antibody

<400> SEQUENCE: 163

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Phe Cys Val Arg
                20                  25                  30

<210> SEQ ID NO 164
<211> LENGTH: 10
<212> TYPE: PRT
<213> ORGANISM: Artificial
<220> FEATURE:
<223> OTHER INFORMATION: Domain of single chain antibody

<400> SEQUENCE: 164

Pro Ser Asp Ser Gly Trp Ser Phe Glu His
1               5                   10

<210> SEQ ID NO 165
<211> LENGTH: 11
<212> TYPE: PRT
<213> ORGANISM: Artificial
<220> FEATURE:
<223> OTHER INFORMATION: Domain of single chain antibody

<400> SEQUENCE: 165

Trp Gly Gln Gly Thr Leu Val Pro Val Ser Ser
1               5                   10

<210> SEQ ID NO 166
<211> LENGTH: 30
<212> TYPE: PRT
<213> ORGANISM: Artificial
<220> FEATURE:
<223> OTHER INFORMATION: Domain of single chain antibody

<400> SEQUENCE: 166

Gln Val Gln Leu Gln Glu Ser Gly Gly Leu Val Gln Pro Gly Gly
1               5                   10                  15
Ser Leu Arg Leu Ser Cys Ala Ala Ser Gly Phe Thr Phe Ser
                20                  25                  30

<210> SEQ ID NO 167
<211> LENGTH: 5
<212> TYPE: PRT
<213> ORGANISM: Artificial
<220> FEATURE:
<223> OTHER INFORMATION: Domain of single chain antibody
```

<400> SEQUENCE: 167

Ser Tyr Ala Met Ser
1               5

<210> SEQ ID NO 168
<211> LENGTH: 14
<212> TYPE: PRT
<213> ORGANISM: Artificial
<220> FEATURE:
<223> OTHER INFORMATION: Domain of single chain antibody

<400> SEQUENCE: 168

Trp Val Arg Gln Ala Pro Gly Lys Gly Leu Glu Trp Val Ala
1               5                   10

<210> SEQ ID NO 169
<211> LENGTH: 17
<212> TYPE: PRT
<213> ORGANISM: Artificial
<220> FEATURE:
<223> OTHER INFORMATION: Domain of single chain antibody

<400> SEQUENCE: 169

Val Ile Ser Tyr Asp Gly Ser Asn Lys Tyr Tyr Ala Asp Ser Val Lys
1               5                   10                  15

Gly

<210> SEQ ID NO 170
<211> LENGTH: 32
<212> TYPE: PRT
<213> ORGANISM: Artificial
<220> FEATURE:
<223> OTHER INFORMATION: Domain of single chain antibody

<400> SEQUENCE: 170

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Val Arg
            20                  25                  30

<210> SEQ ID NO 171
<211> LENGTH: 12
<212> TYPE: PRT
<213> ORGANISM: Artificial
<220> FEATURE:
<223> OTHER INFORMATION: Domain of single chain antibody

<400> SEQUENCE: 171

Gly Asp Arg Ser Tyr Gly Ala Glu Tyr Phe Gln His
1               5                   10

<210> SEQ ID NO 172
<211> LENGTH: 11
<212> TYPE: PRT
<213> ORGANISM: Artificial
<220> FEATURE:
<223> OTHER INFORMATION: Domain of single chain antibody

<400> SEQUENCE: 172

Trp Gly Gln Gly Thr Leu Val Thr Val Ser Ser
1               5                   10

<210> SEQ ID NO 173
<211> LENGTH: 30
<212> TYPE: PRT

<213> ORGANISM: Artificial
<220> FEATURE:
<223> OTHER INFORMATION: Domain of single chain antibody

<400> SEQUENCE: 173

```
Gln Val Gln Leu Gln Glu Ser Gly Gly Gly Leu Val Lys Pro Gly Gly
 1               5                  10                  15

Ser Leu Arg Leu Ser Cys Ala Ala Ser Gly Phe Thr Ser Ser
            20                  25                  30
```

<210> SEQ ID NO 174
<211> LENGTH: 5
<212> TYPE: PRT
<213> ORGANISM: Artificial
<220> FEATURE:
<223> OTHER INFORMATION: Domain of single chain antibody

<400> SEQUENCE: 174

```
Ser Tyr Ala Met His
 1               5
```

<210> SEQ ID NO 175
<211> LENGTH: 14
<212> TYPE: PRT
<213> ORGANISM: Artificial
<220> FEATURE:
<223> OTHER INFORMATION: Domain of single chain antibody

<400> SEQUENCE: 175

```
Trp Val Arg Gln Ala Pro Gly Lys Gly Leu Glu Tyr Val Ser
 1               5                  10
```

<210> SEQ ID NO 176
<211> LENGTH: 16
<212> TYPE: PRT
<213> ORGANISM: Artificial
<220> FEATURE:
<223> OTHER INFORMATION: Domain of single chain antibody

<400> SEQUENCE: 176

```
Ala Ile Gly Gly Asn Gly Gly Thr Tyr Tyr Ala Asp Ser Val Lys Gly
 1               5                  10                  15
```

<210> SEQ ID NO 177
<211> LENGTH: 32
<212> TYPE: PRT
<213> ORGANISM: Artificial
<220> FEATURE:
<223> OTHER INFORMATION: Domain of single chain antibody

<400> SEQUENCE: 177

```
Arg Phe Thr Ile Ser Arg Asp Asn Ser Lys Asn Thr Leu Tyr Leu Gln
 1               5                  10                  15

Met Asn Ser Leu Arg Ala Glu Asp Thr Ala Val Tyr Tyr Cys Ala Lys
            20                  25                  30
```

<210> SEQ ID NO 178
<211> LENGTH: 16
<212> TYPE: PRT
<213> ORGANISM: Artificial
<220> FEATURE:
<223> OTHER INFORMATION: Domain of single chain antibody

<400> SEQUENCE: 178

```
Glu Gly Glu Gln Trp Leu Glu Tyr Arg Tyr Tyr Gly Met Asp Val
 1               5                  10                  15
```

```
<210> SEQ ID NO 179
<211> LENGTH: 11
<212> TYPE: PRT
<213> ORGANISM: Artificial
<220> FEATURE:
<223> OTHER INFORMATION: Domain of single chain antibody

<400> SEQUENCE: 179

Trp Gly Gln Gly Thr Thr Val Thr Val Ser Ser
1               5                   10

<210> SEQ ID NO 180
<211> LENGTH: 30
<212> TYPE: PRT
<213> ORGANISM: Artificial
<220> FEATURE:
<223> OTHER INFORMATION: Domain of single chain antibody

<400> SEQUENCE: 180

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser
            20                  25                  30

<210> SEQ ID NO 181
<211> LENGTH: 5
<212> TYPE: PRT
<213> ORGANISM: Artificial
<220> FEATURE:
<223> OTHER INFORMATION: Domain of single chain antibody

<400> SEQUENCE: 181

Ser Tyr Gly Met His
1               5

<210> SEQ ID NO 182
<211> LENGTH: 14
<212> TYPE: PRT
<213> ORGANISM: Artificial
<220> FEATURE:
<223> OTHER INFORMATION: Domain of single chain antibody

<400> SEQUENCE: 182

Trp Val Arg Gln Ala Pro Gly Lys Gly Leu Glu Trp Val Ala
1               5                   10

<210> SEQ ID NO 183
<211> LENGTH: 17
<212> TYPE: PRT
<213> ORGANISM: Artificial
<220> FEATURE:
<223> OTHER INFORMATION: Domain of single chain antibody

<400> SEQUENCE: 183

Val Ile Ser Tyr Asp Gly Ser Asn Lys Tyr Tyr Ala Asp Ser Val Lys
1               5                   10                  15

Gly

<210> SEQ ID NO 184
<211> LENGTH: 32
<212> TYPE: PRT
<213> ORGANISM: Artificial
<220> FEATURE:
<223> OTHER INFORMATION: Domain of single chain antibody
```

<400> SEQUENCE: 184

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 185
<211> LENGTH: 18
<212> TYPE: PRT
<213> ORGANISM: Artificial
<220> FEATURE:
<223> OTHER INFORMATION: Domain of single chain antibody

<400> SEQUENCE: 185

Gly Gly Arg Tyr Ser Ser Asn Trp Phe Ser Tyr Tyr Tyr Gly Met
1               5                   10                  15

Asp Val

<210> SEQ ID NO 186
<211> LENGTH: 11
<212> TYPE: PRT
<213> ORGANISM: Artificial
<220> FEATURE:
<223> OTHER INFORMATION: Domain of single chain antibody

<400> SEQUENCE: 186

Trp Gly Gln Gly Thr Thr Val Thr Val Ser Ser
1               5                   10

<210> SEQ ID NO 187
<211> LENGTH: 22
<212> TYPE: PRT
<213> ORGANISM: Artificial
<220> FEATURE:
<223> OTHER INFORMATION: Domain of single chain antibody

<400> SEQUENCE: 187

Ser Tyr Val Leu Thr Gln Asp Pro Ala Val Ser Val Ala Leu Gly Gln
1               5                   10                  15

Thr Val Arg Ile Thr Cys
            20

<210> SEQ ID NO 188
<211> LENGTH: 11
<212> TYPE: PRT
<213> ORGANISM: Artificial
<220> FEATURE:
<223> OTHER INFORMATION: Domain of single chain antibody

<400> SEQUENCE: 188

Gln Gly Asp Ser Leu Arg Ser Tyr Tyr Ala Ser
1               5                   10

<210> SEQ ID NO 189
<211> LENGTH: 14
<212> TYPE: PRT
<213> ORGANISM: Artificial
<220> FEATURE:
<223> OTHER INFORMATION: Domain of single chain antibody

<400> SEQUENCE: 189

Trp Tyr Gln Glu Arg Pro Gly Gln Ala Pro Leu Leu Val Ile
1               5                   10

```
<210> SEQ ID NO 190
<211> LENGTH: 8
<212> TYPE: PRT
<213> ORGANISM: Artificial
<220> FEATURE:
<223> OTHER INFORMATION: Domain of single chain antibody

<400> SEQUENCE: 190

Tyr Gly Lys Asn Asn Arg Pro Ser
1               5

<210> SEQ ID NO 191
<211> LENGTH: 32
<212> TYPE: PRT
<213> ORGANISM: Artificial
<220> FEATURE:
<223> OTHER INFORMATION: Domain of single chain antibody

<400> SEQUENCE: 191

Gly Ile Pro Asp Arg Phe Ser Gly Ser Asn Ser Gly Ser Thr Ala Thr
1               5                   10                  15

Leu Thr Ile Ser Arg Val Glu Ala Gly Asp Glu Gly Asp Tyr Tyr Cys
            20                  25                  30

<210> SEQ ID NO 192
<211> LENGTH: 11
<212> TYPE: PRT
<213> ORGANISM: Artificial
<220> FEATURE:
<223> OTHER INFORMATION: Domain of single chain antibody

<400> SEQUENCE: 192

Gln Val Trp Asp Ser Ile Asn Glu Gln Val Val
1               5                   10

<210> SEQ ID NO 193
<211> LENGTH: 10
<212> TYPE: PRT
<213> ORGANISM: Artificial
<220> FEATURE:
<223> OTHER INFORMATION: Domain of single chain antibody

<400> SEQUENCE: 193

Phe Gly Gly Gly Thr Lys Val Thr Val Leu
1               5                   10

<210> SEQ ID NO 194
<211> LENGTH: 22
<212> TYPE: PRT
<213> ORGANISM: Artificial
<220> FEATURE:
<223> OTHER INFORMATION: Domain of single chain antibody

<400> SEQUENCE: 194

Asn Phe Met Leu Thr Gln Pro Pro Ser Val Ser Val Ala Pro Gly Gln
1               5                   10                  15

Thr Ala Lys Ile Thr Cys
            20

<210> SEQ ID NO 195
<211> LENGTH: 11
<212> TYPE: PRT
<213> ORGANISM: Artificial
<220> FEATURE:
<223> OTHER INFORMATION: Domain of single chain antibody

<400> SEQUENCE: 195
```

```
Asp Gly Tyr Ser Ile Arg Thr Lys Ser Val His
1               5                   10

<210> SEQ ID NO 196
<211> LENGTH: 14
<212> TYPE: PRT
<213> ORGANISM: Artificial
<220> FEATURE:
<223> OTHER INFORMATION: Domain of single chain antibody

<400> SEQUENCE: 196

Trp Tyr Gln Gln Lys Pro Gly Gln Ala Pro Val Val Val Val
1               5                   10

<210> SEQ ID NO 197
<211> LENGTH: 8
<212> TYPE: PRT
<213> ORGANISM: Artificial
<220> FEATURE:
<223> OTHER INFORMATION: Domain of single chain antibody

<400> SEQUENCE: 197

His Asp Asp Ser Asp Arg Pro Ser
1               5

<210> SEQ ID NO 198
<211> LENGTH: 32
<212> TYPE: PRT
<213> ORGANISM: Artificial
<220> FEATURE:
<223> OTHER INFORMATION: Domain of single chain antibody

<400> SEQUENCE: 198

Gly Ile Pro Glu Arg Phe Ser Gly Ser Asn Ser Gly Thr Thr Ala Thr
1               5                   10                  15

Leu Thr Ile Ser Arg Val Glu Ala Gly Asp Glu Ala Asp Tyr Tyr Cys
                20                  25                  30

<210> SEQ ID NO 199
<211> LENGTH: 11
<212> TYPE: PRT
<213> ORGANISM: Artificial
<220> FEATURE:
<223> OTHER INFORMATION: Domain of single chain antibody

<400> SEQUENCE: 199

Gln Ala Trp Asp Ser Ile Ser Glu Glu Val Val
1               5                   10

<210> SEQ ID NO 200
<211> LENGTH: 10
<212> TYPE: PRT
<213> ORGANISM: Artificial
<220> FEATURE:
<223> OTHER INFORMATION: Domain of single chain antibody

<400> SEQUENCE: 200

Phe Gly Gly Gly Thr Lys Leu Thr Val Leu
1               5                   10

<210> SEQ ID NO 201
<211> LENGTH: 22
<212> TYPE: PRT
<213> ORGANISM: Artificial
<220> FEATURE:
<223> OTHER INFORMATION: Domain of single chain antibody
```

<400> SEQUENCE: 201

Ser Tyr Val Leu Thr Gln Asp Pro Ala Val Ser Val Ala Leu Gly Gln
1               5                   10                  15

Thr Val Arg Ile Thr Cys
            20

<210> SEQ ID NO 202
<211> LENGTH: 11
<212> TYPE: PRT
<213> ORGANISM: Artificial
<220> FEATURE:
<223> OTHER INFORMATION: Domain of single chain antibody

<400> SEQUENCE: 202

Gln Gly Asp Asn Ile Gly Ser Lys Ser Val His
1               5                   10

<210> SEQ ID NO 203
<211> LENGTH: 14
<212> TYPE: PRT
<213> ORGANISM: Artificial
<220> FEATURE:
<223> OTHER INFORMATION: Domain of single chain antibody

<400> SEQUENCE: 203

Trp Tyr Gln Gln Lys Pro Gly Gln Ala Pro Val Leu Val Val
1               5                   10

<210> SEQ ID NO 204
<211> LENGTH: 8
<212> TYPE: PRT
<213> ORGANISM: Artificial
<220> FEATURE:
<223> OTHER INFORMATION: Domain of single chain antibody

<400> SEQUENCE: 204

Tyr Asp Asp Ser Asp Arg Pro Ser
1               5

<210> SEQ ID NO 205
<211> LENGTH: 32
<212> TYPE: PRT
<213> ORGANISM: Artificial
<220> FEATURE:
<223> OTHER INFORMATION: Domain of single chain antibody

<400> SEQUENCE: 205

Gly Ile Pro Glu Arg Phe Ser Gly Ser Asn Ser Gly Thr Thr Ala Thr
1               5                   10                  15

Leu Thr Ile Ser Ser Val Glu Ala Gly Asp Glu Ala Asp Tyr Tyr Cys
            20                  25                  30

<210> SEQ ID NO 206
<211> LENGTH: 11
<212> TYPE: PRT
<213> ORGANISM: Artificial
<220> FEATURE:
<223> OTHER INFORMATION: Domain of single chain antibody

<400> SEQUENCE: 206

Gln Ala Trp Asp Ser Ile Ser Glu His Val Ile
1               5                   10

<210> SEQ ID NO 207

```
<211> LENGTH: 10
<212> TYPE: PRT
<213> ORGANISM: Artificial
<220> FEATURE:
<223> OTHER INFORMATION: Domain of single chain antibody

<400> SEQUENCE: 207

Phe Gly Gly Gly Thr Lys Val Thr Val Leu
1               5                   10

<210> SEQ ID NO 208
<211> LENGTH: 23
<212> TYPE: PRT
<213> ORGANISM: Artificial
<220> FEATURE:
<223> OTHER INFORMATION: Domain of single chain antibody

<400> SEQUENCE: 208

Asp Ile Gln Met Thr Gln Ser Pro Ser Phe Leu Ser Ala Ser Val Gly
1               5                   10                  15

Asp Arg Ile Thr Ile Thr Cys
            20

<210> SEQ ID NO 209
<211> LENGTH: 11
<212> TYPE: PRT
<213> ORGANISM: Artificial
<220> FEATURE:
<223> OTHER INFORMATION: Domain of single chain antibody

<400> SEQUENCE: 209

Arg Ala Ser His Asp Ile Ser Ser Tyr Phe Ala
1               5                   10

<210> SEQ ID NO 210
<211> LENGTH: 14
<212> TYPE: PRT
<213> ORGANISM: Artificial
<220> FEATURE:
<223> OTHER INFORMATION: Domain of single chain antibody

<400> SEQUENCE: 210

Trp Tyr Gln Gln Lys Pro Gly Lys Ala Pro Lys Pro Leu Ile
1               5                   10

<210> SEQ ID NO 211
<211> LENGTH: 8
<212> TYPE: PRT
<213> ORGANISM: Artificial
<220> FEATURE:
<223> OTHER INFORMATION: Domain of single chain antibody

<400> SEQUENCE: 211

Tyr Ala Ala Ser Thr Leu Gln Ser
1               5

<210> SEQ ID NO 212
<211> LENGTH: 32
<212> TYPE: PRT
<213> ORGANISM: Artificial
<220> FEATURE:
<223> OTHER INFORMATION: Domain of single chain antibody

<400> SEQUENCE: 212

Gly Val Pro Ser Arg Phe Ser Gly Ser Gly Ser Gly Thr Glu Phe Thr
1               5                   10                  15
```

```
Leu Thr Ile Ser Ser Leu Gln Pro Glu Asp Phe Ala Thr Tyr Tyr Cys
        20                  25                  30

<210> SEQ ID NO 213
<211> LENGTH: 9
<212> TYPE: PRT
<213> ORGANISM: Artificial
<220> FEATURE:
<223> OTHER INFORMATION: Domain of single chain antibody

<400> SEQUENCE: 213

Gln Gln Leu Gly Ser Tyr Pro Leu Thr
1               5

<210> SEQ ID NO 214
<211> LENGTH: 10
<212> TYPE: PRT
<213> ORGANISM: Artificial
<220> FEATURE:
<223> OTHER INFORMATION: Domain of single chain antibody

<400> SEQUENCE: 214

Phe Gly Gly Gly Thr Lys Leu Glu Ile Lys
1               5                   10

<210> SEQ ID NO 215
<211> LENGTH: 22
<212> TYPE: PRT
<213> ORGANISM: Artificial
<220> FEATURE:
<223> OTHER INFORMATION: Domain of single chain antibody

<400> SEQUENCE: 215

His Val Ile Leu Thr Gln Asp Pro Ala Val Ser Val Ala Leu Gly Gln
1               5                   10                  15

Thr Val Arg Ile Thr Cys
            20

<210> SEQ ID NO 216
<211> LENGTH: 11
<212> TYPE: PRT
<213> ORGANISM: Artificial
<220> FEATURE:
<223> OTHER INFORMATION: Domain of single chain antibody

<400> SEQUENCE: 216

Gln Gly Asp Ser Leu Lys Ser Tyr Tyr Ala Ser
1               5                   10

<210> SEQ ID NO 217
<211> LENGTH: 14
<212> TYPE: PRT
<213> ORGANISM: Artificial
<220> FEATURE:
<223> OTHER INFORMATION: Domain of single chain antibody

<400> SEQUENCE: 217

Trp Tyr Gln Gln Lys Pro Gly Gln Ala Pro Val Leu Val Ile
1               5                   10

<210> SEQ ID NO 218
<211> LENGTH: 8
<212> TYPE: PRT
<213> ORGANISM: Artificial
<220> FEATURE:
<223> OTHER INFORMATION: Domain of single chain antibody
```

```
<400> SEQUENCE: 218

Tyr Gly Lys Asn Asn Arg Pro Ser
1               5

<210> SEQ ID NO 219
<211> LENGTH: 32
<212> TYPE: PRT
<213> ORGANISM: Artificial
<220> FEATURE:
<223> OTHER INFORMATION: Domain of single chain antibody

<400> SEQUENCE: 219

Gly Ile Pro Asp Arg Phe Ser Gly Ser Ser Gly Thr Thr Ala Ser
1               5                   10                  15

Leu Thr Ile Thr Gly Ala Gln Ala Glu Asp Glu Ala Asp Tyr Tyr Cys
            20                  25                  30

<210> SEQ ID NO 220
<211> LENGTH: 12
<212> TYPE: PRT
<213> ORGANISM: Artificial
<220> FEATURE:
<223> OTHER INFORMATION: Domain of single chain antibody

<400> SEQUENCE: 220

His Ser Arg Asp Ser Ser Gly Thr His Leu Arg Val
1               5                   10

<210> SEQ ID NO 221
<211> LENGTH: 10
<212> TYPE: PRT
<213> ORGANISM: Artificial
<220> FEATURE:
<223> OTHER INFORMATION: Domain of single chain antibody

<400> SEQUENCE: 221

Phe Gly Gly Gly Thr Lys Leu Thr Val Leu
1               5                   10

<210> SEQ ID NO 222
<211> LENGTH: 22
<212> TYPE: PRT
<213> ORGANISM: Artificial
<220> FEATURE:
<223> OTHER INFORMATION: Domain of single chain antibody

<400> SEQUENCE: 222

Gln Ser Val Leu Thr Gln Pro Pro Ser Ala Ser Gly Thr Pro Gly Gln
1               5                   10                  15

Arg Val Thr Ile Ser Cys
            20

<210> SEQ ID NO 223
<211> LENGTH: 13
<212> TYPE: PRT
<213> ORGANISM: Artificial
<220> FEATURE:
<223> OTHER INFORMATION: Domain of single chain antibody

<400> SEQUENCE: 223

Ser Gly Ser Ser Ser Asn Ile Gly Asn Asn Thr Val Asn
1               5                   10

<210> SEQ ID NO 224
<211> LENGTH: 14
```

```
<212> TYPE: PRT
<213> ORGANISM: Artificial
<220> FEATURE:
<223> OTHER INFORMATION: Domain of single chain antibody

<400> SEQUENCE: 224

Trp Ser Arg Gln Leu Pro Gly Thr Ala Pro Lys Leu Leu Ile
1               5                   10

<210> SEQ ID NO 225
<211> LENGTH: 8
<212> TYPE: PRT
<213> ORGANISM: Artificial
<220> FEATURE:
<223> OTHER INFORMATION: Domain of single chain antibody

<400> SEQUENCE: 225

Tyr Ser Asn Asp Gln Arg Pro Ser
1               5

<210> SEQ ID NO 226
<211> LENGTH: 32
<212> TYPE: PRT
<213> ORGANISM: Artificial
<220> FEATURE:
<223> OTHER INFORMATION: Domain of single chain antibody

<400> SEQUENCE: 226

Gly Val Pro Asp Arg Phe Ser Gly Ser Lys Ser Gly Thr Ser Ala Ser
1               5                   10                  15

Leu Ala Ile Thr Gly Leu Gln Pro Glu Asp Glu Ala Asp Tyr Tyr Cys
            20                  25                  30

<210> SEQ ID NO 227
<211> LENGTH: 11
<212> TYPE: PRT
<213> ORGANISM: Artificial
<220> FEATURE:
<223> OTHER INFORMATION: Domain of single chain antibody

<400> SEQUENCE: 227

Gly Thr Trp Asp Ser Ser Leu Ser Ala Tyr Val
1               5                   10

<210> SEQ ID NO 228
<211> LENGTH: 10
<212> TYPE: PRT
<213> ORGANISM: Artificial
<220> FEATURE:
<223> OTHER INFORMATION: Domain of single chain antibody

<400> SEQUENCE: 228

Phe Gly Thr Gly Thr Lys Leu Thr Val Leu
1               5                   10

<210> SEQ ID NO 229
<211> LENGTH: 22
<212> TYPE: PRT
<213> ORGANISM: Artificial
<220> FEATURE:
<223> OTHER INFORMATION: Domain of single chain antibody

<400> SEQUENCE: 229

Ser Ser Glu Leu Thr Gln Asp Pro Ala Val Ser Val Ala Leu Gly Gln
1               5                   10                  15

Thr Val Arg Ile Thr Cys
```

```
                        20

<210> SEQ ID NO 230
<211> LENGTH: 11
<212> TYPE: PRT
<213> ORGANISM: Artificial
<220> FEATURE:
<223> OTHER INFORMATION: Domain of single chain antibody

<400> SEQUENCE: 230

Gln Gly Asp Ser Leu Arg Ser Tyr Tyr Ala Ser
1               5                   10

<210> SEQ ID NO 231
<211> LENGTH: 14
<212> TYPE: PRT
<213> ORGANISM: Artificial
<220> FEATURE:
<223> OTHER INFORMATION: Domain of single chain antibody

<400> SEQUENCE: 231

Trp Tyr Gln Gln Lys Pro Gly Gln Ala Pro Leu Leu Val Ile
1               5                   10

<210> SEQ ID NO 232
<211> LENGTH: 8
<212> TYPE: PRT
<213> ORGANISM: Artificial
<220> FEATURE:
<223> OTHER INFORMATION: Domain of single chain antibody

<400> SEQUENCE: 232

Tyr Gly Gln Asn Ile Arg Pro Ser
1               5

<210> SEQ ID NO 233
<211> LENGTH: 32
<212> TYPE: PRT
<213> ORGANISM: Artificial
<220> FEATURE:
<223> OTHER INFORMATION: Domain of single chain antibody

<400> SEQUENCE: 233

Gly Ile Pro Asp Arg Phe Ser Gly Ser Ser Gly Asn Ser Ala Ser
1               5                   10                  15

Leu Thr Ile Thr Gly Ala Gln Ala Glu Asp Glu Ala Asp Tyr Tyr Cys
            20                  25                  30

<210> SEQ ID NO 234
<211> LENGTH: 10
<212> TYPE: PRT
<213> ORGANISM: Artificial
<220> FEATURE:
<223> OTHER INFORMATION: Domain of single chain antibody

<400> SEQUENCE: 234

His Ser Arg Asp Ser Ser Gly Lys Tyr Val
1               5                   10

<210> SEQ ID NO 235
<211> LENGTH: 10
<212> TYPE: PRT
<213> ORGANISM: Artificial
<220> FEATURE:
<223> OTHER INFORMATION: Domain of single chain antibody

<400> SEQUENCE: 235
```

```
Phe Gly Val Gly Thr Lys Val Thr Val Leu
1               5                   10
```

<210> SEQ ID NO 236
<211> LENGTH: 22
<212> TYPE: PRT
<213> ORGANISM: Artificial
<220> FEATURE:
<223> OTHER INFORMATION: Domain of single chain antibody

<400> SEQUENCE: 236

```
Asn Phe Met Leu Thr Gln Asp Pro Ala Val Ser Val Ala Leu Gly Gln
1               5                   10                  15

Thr Val Arg Ile Thr Cys
            20
```

<210> SEQ ID NO 237
<211> LENGTH: 11
<212> TYPE: PRT
<213> ORGANISM: Artificial
<220> FEATURE:
<223> OTHER INFORMATION: Domain of single chain antibody

<400> SEQUENCE: 237

```
Gln Gly Asp Ser Leu Arg Ser Tyr Tyr Ala Ser
1               5                   10
```

<210> SEQ ID NO 238
<211> LENGTH: 14
<212> TYPE: PRT
<213> ORGANISM: Artificial
<220> FEATURE:
<223> OTHER INFORMATION: Domain of single chain antibody

<400> SEQUENCE: 238

```
Trp Tyr Gln Gln Lys Pro Gly Gln Ala Pro Leu Leu Val Ile
1               5                   10
```

<210> SEQ ID NO 239
<211> LENGTH: 8
<212> TYPE: PRT
<213> ORGANISM: Artificial
<220> FEATURE:
<223> OTHER INFORMATION: Domain of single chain antibody

<400> SEQUENCE: 239

```
Tyr Gly Lys Asn Asn Arg Pro Ser
1               5
```

<210> SEQ ID NO 240
<211> LENGTH: 32
<212> TYPE: PRT
<213> ORGANISM: Artificial
<220> FEATURE:
<223> OTHER INFORMATION: Domain of single chain antibody

<400> SEQUENCE: 240

```
Gly Ile Pro Asp Arg Phe Ser Gly Ser Ser Gly Asn Thr Ala Ser
1               5                   10                  15

Leu Thr Ile Thr Gly Ala Gln Ala Glu Asp Glu Ala Asp Tyr Tyr Cys
                20                  25                  30
```

<210> SEQ ID NO 241
<211> LENGTH: 10
<212> TYPE: PRT

<213> ORGANISM: Artificial
<220> FEATURE:
<223> OTHER INFORMATION: Domain of single chain antibody

<400> SEQUENCE: 241

Asn Ser Arg Asp Ser Ser Gly Asn Pro Val
1               5                   10

<210> SEQ ID NO 242
<211> LENGTH: 10
<212> TYPE: PRT
<213> ORGANISM: Artificial
<220> FEATURE:
<223> OTHER INFORMATION: Domain of single chain antibody

<400> SEQUENCE: 242

Phe Gly Gly Gly Thr Lys Val Thr Val Leu
1               5                   10

<210> SEQ ID NO 243
<211> LENGTH: 22
<212> TYPE: PRT
<213> ORGANISM: Artificial
<220> FEATURE:
<223> OTHER INFORMATION: Domain of single chain antibody

<400> SEQUENCE: 243

Asn Phe Met Leu Thr Gln Asp Pro Ala Val Ser Val Ala Leu Gly Gln
1               5                   10                  15

Thr Val Arg Ile Thr Cys
            20

<210> SEQ ID NO 244
<211> LENGTH: 11
<212> TYPE: PRT
<213> ORGANISM: Artificial
<220> FEATURE:
<223> OTHER INFORMATION: Domain of single chain antibody

<400> SEQUENCE: 244

Gln Gly Asp Ser Leu Arg Ser Tyr Tyr Ala Ser
1               5                   10

<210> SEQ ID NO 245
<211> LENGTH: 14
<212> TYPE: PRT
<213> ORGANISM: Artificial
<220> FEATURE:
<223> OTHER INFORMATION: Domain of single chain antibody

<400> SEQUENCE: 245

Trp Tyr Gln Gln Lys Pro Gly Gln Ala Pro Leu Leu Val Ile
1               5                   10

<210> SEQ ID NO 246
<211> LENGTH: 8
<212> TYPE: PRT
<213> ORGANISM: Artificial
<220> FEATURE:
<223> OTHER INFORMATION: Domain of single chain antibody

<400> SEQUENCE: 246

Tyr Gly Lys Asn Asn Arg Pro Ser
1               5

<210> SEQ ID NO 247

```
<211> LENGTH: 32
<212> TYPE: PRT
<213> ORGANISM: Artificial
<220> FEATURE:
<223> OTHER INFORMATION: Domain of single chain antibody

<400> SEQUENCE: 247

Gly Ile Pro Asp Arg Phe Ser Gly Ser Ser Ser Gly Asn Thr Ala Ser
1               5                   10                  15

Leu Thr Ile Thr Gly Ala Gln Ala Glu Asp Glu Ala Asp Tyr Tyr Cys
            20                  25                  30

<210> SEQ ID NO 248
<211> LENGTH: 10
<212> TYPE: PRT
<213> ORGANISM: Artificial
<220> FEATURE:
<223> OTHER INFORMATION: Domain of single chain antibody

<400> SEQUENCE: 248

Asn Ser Arg Asp Ser Ser Gly Asn Pro Val
1               5                   10

<210> SEQ ID NO 249
<211> LENGTH: 10
<212> TYPE: PRT
<213> ORGANISM: Artificial
<220> FEATURE:
<223> OTHER INFORMATION: Domain of single chain antibody

<400> SEQUENCE: 249

Phe Gly Gly Gly Thr Lys Val Thr Val Leu
1               5                   10

<210> SEQ ID NO 250
<211> LENGTH: 22
<212> TYPE: PRT
<213> ORGANISM: Artificial
<220> FEATURE:
<223> OTHER INFORMATION: Domain of single chain antibody

<400> SEQUENCE: 250

Ser Ser Glu Leu Thr Gln Asp Pro Ala Val Ser Val Ala Leu Gly Gln
1               5                   10                  15

Thr Val Lys Ile Thr Cys
            20

<210> SEQ ID NO 251
<211> LENGTH: 11
<212> TYPE: PRT
<213> ORGANISM: Artificial
<220> FEATURE:
<223> OTHER INFORMATION: Domain of single chain antibody

<400> SEQUENCE: 251

Gln Gly Asp Ser Leu Arg Thr Tyr Tyr Ala Ser
1               5                   10

<210> SEQ ID NO 252
<211> LENGTH: 14
<212> TYPE: PRT
<213> ORGANISM: Artificial
<220> FEATURE:
<223> OTHER INFORMATION: Domain of single chain antibody

<400> SEQUENCE: 252
```

```
Trp Tyr Gln Gln Arg Pro Gly Gln Ala Pro Val Leu Val Ile
1               5                   10

<210> SEQ ID NO 253
<211> LENGTH: 8
<212> TYPE: PRT
<213> ORGANISM: Artificial
<220> FEATURE:
<223> OTHER INFORMATION: Domain of single chain antibody

<400> SEQUENCE: 253

Tyr Gly Glu Asn Ser Arg Pro Ser
1               5

<210> SEQ ID NO 254
<211> LENGTH: 32
<212> TYPE: PRT
<213> ORGANISM: Artificial
<220> FEATURE:
<223> OTHER INFORMATION: Domain of single chain antibody

<400> SEQUENCE: 254

Gly Ile Pro Asp Arg Phe Ser Gly Ser Ser Ser Gly Asn Thr Ala Ser
1               5                   10                  15

Leu Thr Ile Thr Gly Ala Gln Ala Glu Asp Glu Ala Asp Tyr Tyr Cys
            20                  25                  30

<210> SEQ ID NO 255
<211> LENGTH: 12
<212> TYPE: PRT
<213> ORGANISM: Artificial
<220> FEATURE:
<223> OTHER INFORMATION: Domain of single chain antibody

<400> SEQUENCE: 255

Asn Ser Arg Asp Ser Ser Gly Asn His Leu Arg Val
1               5                   10

<210> SEQ ID NO 256
<211> LENGTH: 10
<212> TYPE: PRT
<213> ORGANISM: Artificial
<220> FEATURE:
<223> OTHER INFORMATION: Domain of single chain antibody

<400> SEQUENCE: 256

Phe Gly Gly Gly Thr Lys Leu Thr Val Leu
1               5                   10

<210> SEQ ID NO 257
<211> LENGTH: 22
<212> TYPE: PRT
<213> ORGANISM: Artificial
<220> FEATURE:
<223> OTHER INFORMATION: Domain of single chain antibody

<400> SEQUENCE: 257

Asn Phe Met Leu Thr Gln Pro Pro Ser Val Ser Val Ala Pro Gly Lys
1               5                   10                  15

Thr Ala Ser Leu Thr Cys
            20

<210> SEQ ID NO 258
<211> LENGTH: 11
<212> TYPE: PRT
<213> ORGANISM: Artificial
```

```
<220> FEATURE:
<223> OTHER INFORMATION: Domain of single chain antibody

<400> SEQUENCE: 258

Gly Gly Tyr Asn Ile Gly Thr Lys Ser Val His
1               5                   10

<210> SEQ ID NO 259
<211> LENGTH: 14
<212> TYPE: PRT
<213> ORGANISM: Artificial
<220> FEATURE:
<223> OTHER INFORMATION: Domain of single chain antibody

<400> SEQUENCE: 259

Trp Tyr Gln Gln Lys Pro Gly Gln Ala Pro Val Val Val Val
1               5                   10

<210> SEQ ID NO 260
<211> LENGTH: 8
<212> TYPE: PRT
<213> ORGANISM: Artificial
<220> FEATURE:
<223> OTHER INFORMATION: Domain of single chain antibody

<400> SEQUENCE: 260

His Asp Asp Ser Asp Arg Pro Ser
1               5

<210> SEQ ID NO 261
<211> LENGTH: 32
<212> TYPE: PRT
<213> ORGANISM: Artificial
<220> FEATURE:
<223> OTHER INFORMATION: Domain of single chain antibody

<400> SEQUENCE: 261

Gly Ile Pro Glu Arg Phe Ser Gly Ser Asn Ser Gly Thr Thr Ala Thr
1               5                   10                  15

Leu Thr Ile Ile Arg Val Glu Ala Gly Asp Glu Ala Asp Tyr Tyr Cys
                20                  25                  30

<210> SEQ ID NO 262
<211> LENGTH: 11
<212> TYPE: PRT
<213> ORGANISM: Artificial
<220> FEATURE:
<223> OTHER INFORMATION: Domain of single chain antibody

<400> SEQUENCE: 262

Gln Ala Trp Asp Ser Ile Ser Glu Glu Val Val
1               5                   10

<210> SEQ ID NO 263
<211> LENGTH: 10
<212> TYPE: PRT
<213> ORGANISM: Artificial
<220> FEATURE:
<223> OTHER INFORMATION: Domain of single chain antibody

<400> SEQUENCE: 263

Phe Gly Gly Gly Thr Lys Leu Thr Val Leu
1               5                   10

<210> SEQ ID NO 264
<211> LENGTH: 22
```

```
<212> TYPE: PRT
<213> ORGANISM: Artificial
<220> FEATURE:
<223> OTHER INFORMATION: Domain of single chain antibody

<400> SEQUENCE: 264

Ser Tyr Val Leu Thr Gln Asp Pro Ala Val Ser Val Ala Leu Gly Gln
1               5                   10                  15

Thr Val Arg Ile Thr Cys
            20

<210> SEQ ID NO 265
<211> LENGTH: 11
<212> TYPE: PRT
<213> ORGANISM: Artificial
<220> FEATURE:
<223> OTHER INFORMATION: Domain of single chain antibody

<400> SEQUENCE: 265

Gln Gly Asp Ser Leu Arg Ser Tyr Tyr Ala Ser
1               5                   10

<210> SEQ ID NO 266
<211> LENGTH: 14
<212> TYPE: PRT
<213> ORGANISM: Artificial
<220> FEATURE:
<223> OTHER INFORMATION: Domain of single chain antibody

<400> SEQUENCE: 266

Trp Tyr Gln Glu Arg Pro Gly Gln Ala Pro Leu Leu Val Ile
1               5                   10

<210> SEQ ID NO 267
<211> LENGTH: 8
<212> TYPE: PRT
<213> ORGANISM: Artificial
<220> FEATURE:
<223> OTHER INFORMATION: Domain of single chain antibody

<400> SEQUENCE: 267

Tyr Gly Lys Asn Asn Arg Pro Ser
1               5

<210> SEQ ID NO 268
<211> LENGTH: 32
<212> TYPE: PRT
<213> ORGANISM: Artificial
<220> FEATURE:
<223> OTHER INFORMATION: Domain of single chain antibody

<400> SEQUENCE: 268

Gly Ile Pro Asp Arg Phe Ser Gly Ser Asn Ser Gly Ser Thr Ala Thr
1               5                   10                  15

Leu Thr Ile Ser Arg Val Glu Ala Gly Asp Glu Gly Asp Tyr Tyr Cys
            20                  25                  30

<210> SEQ ID NO 269
<211> LENGTH: 11
<212> TYPE: PRT
<213> ORGANISM: Artificial
<220> FEATURE:
<223> OTHER INFORMATION: Domain of single chain antibody

<400> SEQUENCE: 269

Gln Val Trp Asp Ser Ile Asn Glu Gln Val Val
```

```
1               5                   10
```

<210> SEQ ID NO 270
<211> LENGTH: 10
<212> TYPE: PRT
<213> ORGANISM: Artificial
<220> FEATURE:
<223> OTHER INFORMATION: Domain of single chain antibody

<400> SEQUENCE: 270

```
Phe Gly Gly Gly Thr Lys Val Thr Val Leu
1               5                   10
```

<210> SEQ ID NO 271
<211> LENGTH: 22
<212> TYPE: PRT
<213> ORGANISM: Artificial
<220> FEATURE:
<223> OTHER INFORMATION: Domain of single chain antibody

<400> SEQUENCE: 271

```
Asn Phe Met Leu Thr Gln Pro Pro Ser Val Ser Val Ala Pro Gly Lys
1               5                   10                  15

Thr Ala Arg Ile Thr Cys
            20
```

<210> SEQ ID NO 272
<211> LENGTH: 11
<212> TYPE: PRT
<213> ORGANISM: Artificial
<220> FEATURE:
<223> OTHER INFORMATION: Domain of single chain antibody

<400> SEQUENCE: 272

```
Gly Gly Asn Asn Ile Gly Ser Lys Ser Val Tyr
1               5                   10
```

<210> SEQ ID NO 273
<211> LENGTH: 14
<212> TYPE: PRT
<213> ORGANISM: Artificial
<220> FEATURE:
<223> OTHER INFORMATION: Domain of single chain antibody

<400> SEQUENCE: 273

```
Trp Tyr Gln Gln Lys Pro Gly Gln Ala Pro Val Leu Val Val
1               5                   10
```

<210> SEQ ID NO 274
<211> LENGTH: 8
<212> TYPE: PRT
<213> ORGANISM: Artificial
<220> FEATURE:
<223> OTHER INFORMATION: Domain of single chain antibody

<400> SEQUENCE: 274

```
Tyr Asp Asp Ser Asp Arg Pro Ser
1               5
```

<210> SEQ ID NO 275
<211> LENGTH: 32
<212> TYPE: PRT
<213> ORGANISM: Artificial
<220> FEATURE:
<223> OTHER INFORMATION: Domain of single chain antibody

<400> SEQUENCE: 275

```
Gly Ile Pro Glu Arg Phe Ser Gly Ser Asn Ser Gly Asn Thr Ala Thr
1               5                   10                  15

Leu Thr Ile Ser Arg Val Glu Ala Gly Asp Glu Ala Asp Tyr Tyr Cys
            20                  25                  30
```

```
<210> SEQ ID NO 276
<211> LENGTH: 11
<212> TYPE: PRT
<213> ORGANISM: Artificial
<220> FEATURE:
<223> OTHER INFORMATION: Domain of single chain antibody

<400> SEQUENCE: 276

Gln Val Trp Asp Ser Ser Ser Asp His Val Val
1               5                   10
```

```
<210> SEQ ID NO 277
<211> LENGTH: 10
<212> TYPE: PRT
<213> ORGANISM: Artificial
<220> FEATURE:
<223> OTHER INFORMATION: Domain of single chain antibody

<400> SEQUENCE: 277

Phe Gly Gly Gly Thr Lys Val Thr Val Leu
1               5                   10
```

```
<210> SEQ ID NO 278
<211> LENGTH: 22
<212> TYPE: PRT
<213> ORGANISM: Artificial
<220> FEATURE:
<223> OTHER INFORMATION: Domain of single chain antibody

<400> SEQUENCE: 278

Ser Ser Glu Leu Thr Gln Asp Pro Ala Val Ser Val Ala Leu Gly Gln
1               5                   10                  15

Thr Val Arg Ile Thr Cys
            20
```

```
<210> SEQ ID NO 279
<211> LENGTH: 11
<212> TYPE: PRT
<213> ORGANISM: Artificial
<220> FEATURE:
<223> OTHER INFORMATION: Domain of single chain antibody

<400> SEQUENCE: 279

Gln Gly Asp Ser Leu Arg Ser Tyr Tyr Ala Ser
1               5                   10
```

```
<210> SEQ ID NO 280
<211> LENGTH: 14
<212> TYPE: PRT
<213> ORGANISM: Artificial
<220> FEATURE:
<223> OTHER INFORMATION: Domain of single chain antibody

<400> SEQUENCE: 280

Trp Tyr Gln Glu Arg Pro Gly Gln Ala Pro Leu Leu Val Ile
1               5                   10
```

```
<210> SEQ ID NO 281
<211> LENGTH: 8
<212> TYPE: PRT
```

```
<213> ORGANISM: Artificial
<220> FEATURE:
<223> OTHER INFORMATION: Domain of single chain antibody

<400> SEQUENCE: 281

Tyr Gly Arg Asn Glu Arg Pro Ser
1               5

<210> SEQ ID NO 282
<211> LENGTH: 32
<212> TYPE: PRT
<213> ORGANISM: Artificial
<220> FEATURE:
<223> OTHER INFORMATION: Domain of single chain antibody

<400> SEQUENCE: 282

Gly Ile Pro Asp Arg Phe Ser Ala Ser Ser Gly Asn Thr Ala Ser
1               5                   10                  15

Leu Thr Ile Thr Gly Ala Gln Ala Glu Asp Glu Ala Asp Tyr Tyr Cys
            20                  25                  30

<210> SEQ ID NO 283
<211> LENGTH: 11
<212> TYPE: PRT
<213> ORGANISM: Artificial
<220> FEATURE:
<223> OTHER INFORMATION: Domain of single chain antibody

<400> SEQUENCE: 283

Gln Val Trp Asp Ser Phe Asn Glu Gln Val Val
1               5                   10

<210> SEQ ID NO 284
<211> LENGTH: 10
<212> TYPE: PRT
<213> ORGANISM: Artificial
<220> FEATURE:
<223> OTHER INFORMATION: Domain of single chain antibody

<400> SEQUENCE: 284

Phe Gly Gly Gly Thr Lys Leu Thr Val Leu
1               5                   10

<210> SEQ ID NO 285
<211> LENGTH: 22
<212> TYPE: PRT
<213> ORGANISM: Artificial
<220> FEATURE:
<223> OTHER INFORMATION: Domain of single chain antibody

<400> SEQUENCE: 285

Ser Ser Glu Leu Thr Gln Asp Pro Ala Val Ser Val Gly Leu Gly Gln
1               5                   10                  15

Thr Val Thr Ile Thr Cys
            20

<210> SEQ ID NO 286
<211> LENGTH: 11
<212> TYPE: PRT
<213> ORGANISM: Artificial
<220> FEATURE:
<223> OTHER INFORMATION: Domain of single chain antibody

<400> SEQUENCE: 286

Gln Gly Asp Ser Leu Arg Ser Tyr Tyr Ala Asn
1               5                   10
```

<210> SEQ ID NO 287
<211> LENGTH: 14
<212> TYPE: PRT
<213> ORGANISM: Artificial
<220> FEATURE:
<223> OTHER INFORMATION: Domain of single chain antibody

<400> SEQUENCE: 287

Trp Tyr Gln Gln Lys Pro Gly Gln Ala Pro Ile Leu Val Ile
1               5                   10

<210> SEQ ID NO 288
<211> LENGTH: 8
<212> TYPE: PRT
<213> ORGANISM: Artificial
<220> FEATURE:
<223> OTHER INFORMATION: Domain of single chain antibody

<400> SEQUENCE: 288

Tyr Gly Glu Asn Asn Arg Pro Ser
1               5

<210> SEQ ID NO 289
<211> LENGTH: 32
<212> TYPE: PRT
<213> ORGANISM: Artificial
<220> FEATURE:
<223> OTHER INFORMATION: Domain of single chain antibody

<400> SEQUENCE: 289

Gly Ile Pro Asp Arg Phe Ser Gly Ser Ser Ser Gly Asn Thr Ala Ser
1               5                   10                  15

Leu Thr Ile Thr Gly Ala Gln Ala Glu Asp Glu Ala Asp Tyr Tyr Cys
            20                  25                  30

<210> SEQ ID NO 290
<211> LENGTH: 12
<212> TYPE: PRT
<213> ORGANISM: Artificial
<220> FEATURE:
<223> OTHER INFORMATION: Domain of single chain antibody

<400> SEQUENCE: 290

His Ser Arg Asp Ser Ser Gly Thr His Leu Arg Val
1               5                   10

<210> SEQ ID NO 291
<211> LENGTH: 10
<212> TYPE: PRT
<213> ORGANISM: Artificial
<220> FEATURE:
<223> OTHER INFORMATION: Domain of single chain antibody

<400> SEQUENCE: 291

Phe Gly Gly Gly Thr Lys Leu Thr Val Leu
1               5                   10

<210> SEQ ID NO 292
<211> LENGTH: 22
<212> TYPE: PRT
<213> ORGANISM: Artificial
<220> FEATURE:
<223> OTHER INFORMATION: Domain of single chain antibody

<400> SEQUENCE: 292

```
Gln Ser Val Leu Thr Gln Pro Pro Ser Ala Ser Gly Thr Pro Gly Gln
1               5                   10                  15

Arg Val Thr Ile Ser Cys
            20
```

<210> SEQ ID NO 293
<211> LENGTH: 13
<212> TYPE: PRT
<213> ORGANISM: Artificial
<220> FEATURE:
<223> OTHER INFORMATION: Domain of single chain antibody

<400> SEQUENCE: 293

```
Ser Gly Ser Ser Ser Asn Ile Gly Asn Asn Thr Val Asn
1               5                   10
```

<210> SEQ ID NO 294
<211> LENGTH: 14
<212> TYPE: PRT
<213> ORGANISM: Artificial
<220> FEATURE:
<223> OTHER INFORMATION: Domain of single chain antibody

<400> SEQUENCE: 294

```
Trp Ser Arg Gln Leu Pro Gly Thr Ala Pro Lys Leu Leu Ile
1               5                   10
```

<210> SEQ ID NO 295
<211> LENGTH: 8
<212> TYPE: PRT
<213> ORGANISM: Artificial
<220> FEATURE:
<223> OTHER INFORMATION: Domain of single chain antibody

<400> SEQUENCE: 295

```
Tyr Ser Asn Asp Gln Arg Pro Ser
1               5
```

<210> SEQ ID NO 296
<211> LENGTH: 32
<212> TYPE: PRT
<213> ORGANISM: Artificial
<220> FEATURE:
<223> OTHER INFORMATION: Domain of single chain antibody

<400> SEQUENCE: 296

```
Gly Val Pro Asp Arg Phe Ser Gly Ser Lys Ser Gly Thr Ser Ala Ser
1               5                   10                  15

Leu Ala Ile Thr Gly Leu Gln Pro Glu Asp Glu Ala Asp Tyr Tyr Cys
            20                  25                  30
```

<210> SEQ ID NO 297
<211> LENGTH: 11
<212> TYPE: PRT
<213> ORGANISM: Artificial
<220> FEATURE:
<223> OTHER INFORMATION: Domain of single chain antibody

<400> SEQUENCE: 297

```
Gly Thr Trp Asp Ser Ser Leu Ser Ala Tyr Val
1               5                   10
```

<210> SEQ ID NO 298
<211> LENGTH: 10
<212> TYPE: PRT
<213> ORGANISM: Artificial

```
<220> FEATURE:
<223> OTHER INFORMATION: Domain of single chain antibody

<400> SEQUENCE: 298

Phe Gly Thr Gly Thr Lys Leu Thr Val Leu
1               5                   10

<210> SEQ ID NO 299
<211> LENGTH: 22
<212> TYPE: PRT
<213> ORGANISM: Artificial
<220> FEATURE:
<223> OTHER INFORMATION: Domain of single chain antibody

<400> SEQUENCE: 299

Ser Ser Glu Leu Thr Gln Asp Pro Ala Val Ser Val Ala Leu Gly Gln
1               5                   10                  15

Thr Val Arg Ile Thr Cys
            20

<210> SEQ ID NO 300
<211> LENGTH: 11
<212> TYPE: PRT
<213> ORGANISM: Artificial
<220> FEATURE:
<223> OTHER INFORMATION: Domain of single chain antibody

<400> SEQUENCE: 300

Gln Gly Asp Ser Leu Arg Ser Tyr Tyr Ala Ser
1               5                   10

<210> SEQ ID NO 301
<211> LENGTH: 14
<212> TYPE: PRT
<213> ORGANISM: Artificial
<220> FEATURE:
<223> OTHER INFORMATION: Domain of single chain antibody

<400> SEQUENCE: 301

Trp Tyr Gln Gln Lys Pro Gly Gln Ala Pro Ser Leu Val Ile
1               5                   10

<210> SEQ ID NO 302
<211> LENGTH: 8
<212> TYPE: PRT
<213> ORGANISM: Artificial
<220> FEATURE:
<223> OTHER INFORMATION: Domain of single chain antibody

<400> SEQUENCE: 302

Tyr Gly Glu Asn Ser Arg Pro Ser
1               5

<210> SEQ ID NO 303
<211> LENGTH: 32
<212> TYPE: PRT
<213> ORGANISM: Artificial
<220> FEATURE:
<223> OTHER INFORMATION: Domain of single chain antibody

<400> SEQUENCE: 303

Gly Ile Pro Asp Arg Phe Ser Gly Ser Ser Ser Gly Asn Thr Ala Ser
1               5                   10                  15

Leu Thr Ile Thr Gly Ala Gln Ala Glu Asn Glu Ala Asp Tyr Tyr Cys
            20                  25                  30
```

<210> SEQ ID NO 304
<211> LENGTH: 10
<212> TYPE: PRT
<213> ORGANISM: Artificial
<220> FEATURE:
<223> OTHER INFORMATION: Domain of single chain antibody

<400> SEQUENCE: 304

Gln Ala Trp Asp Ser Ser Thr Ala Val Val
1               5                   10

<210> SEQ ID NO 305
<211> LENGTH: 10
<212> TYPE: PRT
<213> ORGANISM: Artificial
<220> FEATURE:
<223> OTHER INFORMATION: Domain of single chain antibody

<400> SEQUENCE: 305

Phe Gly Gly Gly Thr Lys Leu Thr Val Leu
1               5                   10

<210> SEQ ID NO 306
<211> LENGTH: 22
<212> TYPE: PRT
<213> ORGANISM: Artificial
<220> FEATURE:
<223> OTHER INFORMATION: Domain of single chain antibody

<400> SEQUENCE: 306

Ser Ser Glu Leu Thr Gln Asp Pro Ala Val Ser Val Ala Leu Gly Gln
1               5                   10                  15

Thr Val Arg Ile Thr Cys
            20

<210> SEQ ID NO 307
<211> LENGTH: 11
<212> TYPE: PRT
<213> ORGANISM: Artificial
<220> FEATURE:
<223> OTHER INFORMATION: Domain of single chain antibody

<400> SEQUENCE: 307

Gln Gly Asp Ser Leu Arg Ser Tyr Tyr Ala Ser
1               5                   10

<210> SEQ ID NO 308
<211> LENGTH: 14
<212> TYPE: PRT
<213> ORGANISM: Artificial
<220> FEATURE:
<223> OTHER INFORMATION: Domain of single chain antibody

<400> SEQUENCE: 308

Trp Tyr Gln Gln Lys Pro Gly Gln Ala Pro Ser Leu Val Ile
1               5                   10

<210> SEQ ID NO 309
<211> LENGTH: 8
<212> TYPE: PRT
<213> ORGANISM: Artificial
<220> FEATURE:
<223> OTHER INFORMATION: Domain of single chain antibody

<400> SEQUENCE: 309

Tyr Gly Glu Asn Ser Arg Pro Ser

```
1               5

<210> SEQ ID NO 310
<211> LENGTH: 32
<212> TYPE: PRT
<213> ORGANISM: Artificial
<220> FEATURE:
<223> OTHER INFORMATION: Domain of single chain antibody

<400> SEQUENCE: 310

Gly Ile Pro Asp Arg Phe Ser Gly Ser Ser Ser Gly Asn Thr Ala Ser
1               5                   10                  15

Leu Thr Ile Thr Gly Ala Gln Ala Glu Asn Glu Ala Asp Tyr Tyr Cys
            20                  25                  30

<210> SEQ ID NO 311
<211> LENGTH: 10
<212> TYPE: PRT
<213> ORGANISM: Artificial
<220> FEATURE:
<223> OTHER INFORMATION: Domain of single chain antibody

<400> SEQUENCE: 311

Gln Ala Trp Asp Ser Ser Thr Ala Val Val
1               5                   10

<210> SEQ ID NO 312
<211> LENGTH: 10
<212> TYPE: PRT
<213> ORGANISM: Artificial
<220> FEATURE:
<223> OTHER INFORMATION: Domain of single chain antibody

<400> SEQUENCE: 312

Phe Gly Gly Gly Thr Lys Leu Thr Val Leu
1               5                   10

<210> SEQ ID NO 313
<211> LENGTH: 23
<212> TYPE: PRT
<213> ORGANISM: Artificial
<220> FEATURE:
<223> OTHER INFORMATION: Domain of single chain antibody

<400> SEQUENCE: 313

Asp Ile Val Met Thr Gln Ser Pro Ser Thr Leu Ser Ala Ser Ile Gly
1               5                   10                  15

Asp Arg Val Thr Ile Thr Cys
            20

<210> SEQ ID NO 314
<211> LENGTH: 11
<212> TYPE: PRT
<213> ORGANISM: Artificial
<220> FEATURE:
<223> OTHER INFORMATION: Domain of single chain antibody

<400> SEQUENCE: 314

Arg Ala Ser Glu Gly Ile Tyr His Trp Leu Ala
1               5                   10

<210> SEQ ID NO 315
<211> LENGTH: 14
<212> TYPE: PRT
<213> ORGANISM: Artificial
<220> FEATURE:
```

<223> OTHER INFORMATION: Domain of single chain antibody

<400> SEQUENCE: 315

Trp Tyr Gln Gln Lys Pro Gly Lys Ala Pro Lys Leu Leu Ile
1               5                   10

<210> SEQ ID NO 316
<211> LENGTH: 8
<212> TYPE: PRT
<213> ORGANISM: Artificial
<220> FEATURE:
<223> OTHER INFORMATION: Domain of single chain antibody

<400> SEQUENCE: 316

Tyr Lys Ala Ser Ser Leu Ala Ser
1               5

<210> SEQ ID NO 317
<211> LENGTH: 32
<212> TYPE: PRT
<213> ORGANISM: Artificial
<220> FEATURE:
<223> OTHER INFORMATION: Domain of single chain antibody

<400> SEQUENCE: 317

Gly Ala Pro Ser Arg Phe Ser Gly Ser Gly Ser Gly Thr Asp Phe Thr
1               5                   10                  15

Leu Thr Ile Ser Ser Leu Gln Pro Asp Asp Phe Ala Thr Tyr Tyr Cys
            20                  25                  30

<210> SEQ ID NO 318
<211> LENGTH: 9
<212> TYPE: PRT
<213> ORGANISM: Artificial
<220> FEATURE:
<223> OTHER INFORMATION: Domain of single chain antibody

<400> SEQUENCE: 318

Gln Gln Tyr His Thr Ile Ser Arg Thr
1               5

<210> SEQ ID NO 319
<211> LENGTH: 10
<212> TYPE: PRT
<213> ORGANISM: Artificial
<220> FEATURE:
<223> OTHER INFORMATION: Domain of single chain antibody

<400> SEQUENCE: 319

Phe Gly Pro Gly Thr Lys Val Asp Ile Lys
1               5                   10

<210> SEQ ID NO 320
<211> LENGTH: 22
<212> TYPE: PRT
<213> ORGANISM: Artificial
<220> FEATURE:
<223> OTHER INFORMATION: Domain of single chain antibody

<400> SEQUENCE: 320

Gln Ser Val Leu Thr Gln Pro Pro Ser Ala Ser Gly Thr Pro Gly Gln
1               5                   10                  15

Arg Val Thr Ile Ser Cys
            20

```
<210> SEQ ID NO 321
<211> LENGTH: 13
<212> TYPE: PRT
<213> ORGANISM: Artificial
<220> FEATURE:
<223> OTHER INFORMATION: Domain of single chain antibody

<400> SEQUENCE: 321

Ser Gly Ser Ser Ser Asn Ile Gly Asn Asn Thr Val Asn
1               5                   10

<210> SEQ ID NO 322
<211> LENGTH: 14
<212> TYPE: PRT
<213> ORGANISM: Artificial
<220> FEATURE:
<223> OTHER INFORMATION: Domain of single chain antibody

<400> SEQUENCE: 322

Trp Ser Arg Gln Leu Pro Gly Thr Ala Pro Lys Leu Leu Ile
1               5                   10

<210> SEQ ID NO 323
<211> LENGTH: 8
<212> TYPE: PRT
<213> ORGANISM: Artificial
<220> FEATURE:
<223> OTHER INFORMATION: Domain of single chain antibody

<400> SEQUENCE: 323

Tyr Ser Asn Asp Gln Arg Pro Ser
1               5

<210> SEQ ID NO 324
<211> LENGTH: 32
<212> TYPE: PRT
<213> ORGANISM: Artificial
<220> FEATURE:
<223> OTHER INFORMATION: Domain of single chain antibody

<400> SEQUENCE: 324

Gly Val Pro Asp Arg Phe Ser Gly Ser Lys Ser Gly Thr Ser Ala Ser
1               5                   10                  15

Leu Ala Ile Thr Gly Leu Gln Pro Glu Asp Glu Ala Asp Tyr Tyr Cys
                20                  25                  30

<210> SEQ ID NO 325
<211> LENGTH: 11
<212> TYPE: PRT
<213> ORGANISM: Artificial
<220> FEATURE:
<223> OTHER INFORMATION: Domain of single chain antibody

<400> SEQUENCE: 325

Gly Thr Trp Asp Ser Ser Leu Ser Ala Tyr Val
1               5                   10

<210> SEQ ID NO 326
<211> LENGTH: 10
<212> TYPE: PRT
<213> ORGANISM: Artificial
<220> FEATURE:
<223> OTHER INFORMATION: Domain of single chain antibody

<400> SEQUENCE: 326

Phe Gly Thr Gly Thr Lys Leu Thr Val Leu
1               5                   10
```

<210> SEQ ID NO 327
<211> LENGTH: 22
<212> TYPE: PRT
<213> ORGANISM: Artificial
<220> FEATURE:
<223> OTHER INFORMATION: Domain of single chain antibody

<400> SEQUENCE: 327

Ser Ser Glu Leu Thr Gln Asp Pro Ala Val Ser Val Ala Ser Gly Gln
1               5                   10                  15

Thr Val Arg Ile Thr Cys
            20

<210> SEQ ID NO 328
<211> LENGTH: 11
<212> TYPE: PRT
<213> ORGANISM: Artificial
<220> FEATURE:
<223> OTHER INFORMATION: Domain of single chain antibody

<400> SEQUENCE: 328

Gln Gly Asp Ser Leu Arg Ser Tyr Tyr Ala Ser
1               5                   10

<210> SEQ ID NO 329
<211> LENGTH: 14
<212> TYPE: PRT
<213> ORGANISM: Artificial
<220> FEATURE:
<223> OTHER INFORMATION: Domain of single chain antibody

<400> SEQUENCE: 329

Trp Tyr Gln Gln Lys Pro Gly Gln Ala Pro Leu Leu Val Ile
1               5                   10

<210> SEQ ID NO 330
<211> LENGTH: 8
<212> TYPE: PRT
<213> ORGANISM: Artificial
<220> FEATURE:
<223> OTHER INFORMATION: Domain of single chain antibody

<400> SEQUENCE: 330

Tyr Gly Lys Asn Ile Arg Pro Ser
1               5

<210> SEQ ID NO 331
<211> LENGTH: 32
<212> TYPE: PRT
<213> ORGANISM: Artificial
<220> FEATURE:
<223> OTHER INFORMATION: Domain of single chain antibody

<400> SEQUENCE: 331

Gly Ile Pro Asp Arg Phe Ser Gly Ser Thr Ser Gly Asn Ser Ala Ser
1               5                   10                  15

Leu Thr Ile Thr Gly Ala Gln Ala Glu Asp Glu Ala Asp Tyr Tyr Cys
            20                  25                  30

<210> SEQ ID NO 332
<211> LENGTH: 12
<212> TYPE: PRT
<213> ORGANISM: Artificial
<220> FEATURE:
<223> OTHER INFORMATION: Domain of single chain antibody

```
<400> SEQUENCE: 332

Asn Ser Arg Asp Ser Ser Gly Asn Arg Asn Trp Val
1               5                   10

<210> SEQ ID NO 333
<211> LENGTH: 10
<212> TYPE: PRT
<213> ORGANISM: Artificial
<220> FEATURE:
<223> OTHER INFORMATION: Domain of single chain antibody

<400> SEQUENCE: 333

Phe Gly Gly Gly Thr Lys Leu Thr Val Leu
1               5                   10

<210> SEQ ID NO 334
<211> LENGTH: 22
<212> TYPE: PRT
<213> ORGANISM: Artificial
<220> FEATURE:
<223> OTHER INFORMATION: Domain of single chain antibody

<400> SEQUENCE: 334

Ser Ser Glu Leu Thr Gln Asp Pro Ala Val Ser Val Ala Leu Gly Gln
1               5                   10                  15

Thr Val Arg Ile Thr Cys
            20

<210> SEQ ID NO 335
<211> LENGTH: 11
<212> TYPE: PRT
<213> ORGANISM: Artificial
<220> FEATURE:
<223> OTHER INFORMATION: Domain of single chain antibody

<400> SEQUENCE: 335

Gln Gly Asp Ser Leu Arg Ser Tyr Tyr Ala Ser
1               5                   10

<210> SEQ ID NO 336
<211> LENGTH: 14
<212> TYPE: PRT
<213> ORGANISM: Artificial
<220> FEATURE:
<223> OTHER INFORMATION: Domain of single chain antibody

<400> SEQUENCE: 336

Trp Tyr Gln Gln Lys Pro Gly Gln Ala Pro Ser Leu Val Ile
1               5                   10

<210> SEQ ID NO 337
<211> LENGTH: 8
<212> TYPE: PRT
<213> ORGANISM: Artificial
<220> FEATURE:
<223> OTHER INFORMATION: Domain of single chain antibody

<400> SEQUENCE: 337

Tyr Gly Glu Asn Ser Arg Pro Ser
1               5

<210> SEQ ID NO 338
<211> LENGTH: 32
<212> TYPE: PRT
<213> ORGANISM: Artificial
```

```
<220> FEATURE:
<223> OTHER INFORMATION: Domain of single chain antibody

<400> SEQUENCE: 338

Gly Ile Pro Asp Arg Phe Ser Gly Ser Ser Gly Asn Thr Ala Ser
1               5                   10                  15

Leu Thr Ile Thr Gly Ala Gln Ala Glu Asn Glu Ala Asp Tyr Tyr Cys
            20                  25                  30

<210> SEQ ID NO 339
<211> LENGTH: 10
<212> TYPE: PRT
<213> ORGANISM: Artificial
<220> FEATURE:
<223> OTHER INFORMATION: Domain of single chain antibody

<400> SEQUENCE: 339

Gln Ala Trp Asp Ser Ser Thr Ala Val Val
1               5                   10

<210> SEQ ID NO 340
<211> LENGTH: 10
<212> TYPE: PRT
<213> ORGANISM: Artificial
<220> FEATURE:
<223> OTHER INFORMATION: Domain of single chain antibody

<400> SEQUENCE: 340

Phe Gly Gly Gly Thr Lys Leu Thr Val Leu
1               5                   10

<210> SEQ ID NO 341
<211> LENGTH: 22
<212> TYPE: PRT
<213> ORGANISM: Artificial
<220> FEATURE:
<223> OTHER INFORMATION: Domain of single chain antibody

<400> SEQUENCE: 341

Asn Phe Met Leu Thr Gln Pro Pro Ser Val Ser Val Ala Pro Gly Lys
1               5                   10                  15

Thr Ala Arg Ile Thr Cys
            20

<210> SEQ ID NO 342
<211> LENGTH: 11
<212> TYPE: PRT
<213> ORGANISM: Artificial
<220> FEATURE:
<223> OTHER INFORMATION: Domain of single chain antibody

<400> SEQUENCE: 342

Gly Gly Asn Asn Ile Gly Ser Lys Ser Val Tyr
1               5                   10

<210> SEQ ID NO 343
<211> LENGTH: 14
<212> TYPE: PRT
<213> ORGANISM: Artificial
<220> FEATURE:
<223> OTHER INFORMATION: Domain of single chain antibody

<400> SEQUENCE: 343

Trp Tyr Gln Gln Lys Pro Gly Gln Ala Pro Val Leu Val Val
1               5                   10
```

```
<210> SEQ ID NO 344
<211> LENGTH: 8
<212> TYPE: PRT
<213> ORGANISM: Artificial
<220> FEATURE:
<223> OTHER INFORMATION: Domain of single chain antibody

<400> SEQUENCE: 344

Tyr Asp Asp Ser Asp Arg Pro Ser
1               5

<210> SEQ ID NO 345
<211> LENGTH: 32
<212> TYPE: PRT
<213> ORGANISM: Artificial
<220> FEATURE:
<223> OTHER INFORMATION: Domain of single chain antibody

<400> SEQUENCE: 345

Gly Ile Pro Glu Arg Phe Ser Gly Ser Asn Ser Gly Asn Thr Ala Thr
1               5                   10                  15

Leu Thr Ile Ser Arg Val Glu Ala Gly Asp Glu Ala Asp Tyr Tyr Cys
            20                  25                  30

<210> SEQ ID NO 346
<211> LENGTH: 11
<212> TYPE: PRT
<213> ORGANISM: Artificial
<220> FEATURE:
<223> OTHER INFORMATION: Domain of single chain antibody

<400> SEQUENCE: 346

Gln Val Trp Asp Ser Ser Ser Asp His Val Val
1               5                   10

<210> SEQ ID NO 347
<211> LENGTH: 10
<212> TYPE: PRT
<213> ORGANISM: Artificial
<220> FEATURE:
<223> OTHER INFORMATION: Domain of single chain antibody

<400> SEQUENCE: 347

Phe Gly Gly Gly Thr Lys Val Thr Val Leu
1               5                   10

<210> SEQ ID NO 348
<211> LENGTH: 18
<212> TYPE: DNA
<213> ORGANISM: Artificial
<220> FEATURE:
<223> OTHER INFORMATION: PCR primer

<400> SEQUENCE: 348
tttttggaga ttttcaac                                                 18

<210> SEQ ID NO 349
<211> LENGTH: 17
<212> TYPE: DNA
<213> ORGANISM: Artificial
<220> FEATURE:
<223> OTHER INFORMATION: PCR primer

<400> SEQUENCE: 349
gaattttctg tatgagg                                                  17
```

```
<210> SEQ ID NO 350
<211> LENGTH: 15
<212> TYPE: PRT
<213> ORGANISM: Artificial
<220> FEATURE:
<223> OTHER INFORMATION: Peptide linker

<400> SEQUENCE: 350

Gly Gly Gly Gly Ser Gly Gly Gly Gly Ser Gly Gly Gly Gly Ser
1               5                  10                  15
```

INTERNALIZING HUMAN MONOCLONAL ANTIBODIES TARGETING PROSTATE CANCER CELLS IN SITU

CROSS-REFERENCE TO RELATED APPLICATIONS

This application is a continuation-in-part of PCT/US2008/076704 (WO/2009/039192), filed on Sep. 17, 2008, which claims benefit of and priority to U.S. Ser. No. 60/973,005, filed on Sep. 17, 2007, both of which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made in part with Government Support by Grant Nos: R01CA118919, R21DK066428-01, and P50 CA8952 from the National Institutes of Health. The Government of the United States of America has certain rights in this invention.

FIELD OF THE INVENTION

This invention pertains to the field of antibodies, immunodiagnostics, and immunotherapeutics. In particular, this invention pertains to novel methods for in vivo screening of antibodies and the discovery of prostate cancer specific internalizing antibodies using such methods.

BACKGROUND OF THE INVENTION

Due to ease of accessibility, tumor cell surface antigens are invaluable targets for therapeutic development. The epitope space at the cell surface is highly complex. Relevant antigens may include glycosylated proteins and other post-translationally modified products that may not be readily predicted from studies of genomic copy number or mRNA expression levels (Liu et al. (2004) *Cancer Res.* 64: 704-710; Kobata and Amano (2005) *Immunol. Cell Biol.* 83: 429-439; Birkle et al. (2003) *Biochimie (Paris)* 85: 455-463; Hakomori (2001) *Adv. Exp. Med. Biol.* 491: 369-402; Hanisch, F. G. (2001) O-Glycosylation of the mucin type. *Biol. Chem.* 382, 143-1 49; Ugorski and Laskowska (2002) *Acta Biochim. Pol.* 49: 303-311).

Because monoclonal antibodies (mAbs) recognize a wide range of antigenic determinants with high affinity and specificity and are able to discern subtle differences in antigen structure and conformation, they can be used to efficiently map the tumor cell surface epitope space (Liu et al. (2004) *Cancer Res.* 64, 704-710). Isolating these epitopes enables the antibodies to achieve specific binding to neoplastic cells, an ability that could be utilized in applications such as induction of antibody-dependent cell cytotoxicity (Clynes et al. (2000) *Nat. Med.* 6: 443-446) or inhibition of signaling pathways involved in tumor cell migration, growth, and survival (McWhirter et al. (2006) *Proc. Natl. Acad. Sci., USA,* 103: 1041-1 046; Fuh et al. (2006) *J. Biol. Chem.* 281: 6625-6631). In addition, antibodies targeting internalizing tumor epitopes could be exploited to achieve efficient and specific intracellular delivery of chemotherapeutic drugs and/or other tumor-modulating agents (Liu et al. (2004) *Cancer Res.* 64: 704-710; Nielsen et al. (2002) *Biochim. Biophys. Acta* 1591: 109-118; Pirollo et al. (2006) *Hum. Gene Ther.* 17: 117-124; Song et al. (2005) *Nat. Biotechnol.* 23:709-717; Liu et al. (2002) *J. Mol. Biol.* 315: 1063-1073).

Phage antibody display has been widely used to develop cancer-specific antibodies (Liu et al. (2004) *Cancer Res.* 64: 704-710; Liu and Marks (2000) *Anal. Biochem.* 286: 119-128; 15. Marks et al. (1992) *Biotechnology* (N.Y.) 10: 779-783; Marks et al. (1991) *J. Mol. Biol.* 222: 581-597; Marks et al. (1992) *J. Biol. Chem.* 267: 16007-16010; Sharon et al. (2005) *J. Cell. Biochem.* 96: 305-313; Silacci et al. (2005) *Proteomics* 5: 2340-2350; Gao et al. (2003) *J. Immunol. Methods* 274: 185-197; Lekkerkerker and Logtenberg (1999) *J. Immunol. Meth.,* 231: 53-63; de Kruif et al. (1995) *Proc. Natl. Acad. Sci., USA,* 92: 3938-3942; Pini et al. (1998) *J. Biol. Chem.* 273: 21 769-21 776). A combinatorial phage antibody library serves as a source of random shape repertoire that can be used to probe neoplastic variations on the surface of cancer cells (Liu et al. (2004) *Cancer Res.* 64: 704-710; Geuijen et al. (2005) *Eur. J. Cancer* 41: 178-187; Poul et al. (2000) *J. Mol. Biol.* 301: 1149-1161; Cai and Garen (1995) *Proc. Natl. Acad. Sci., USA,* 92: 6537-6541). Selecting phage antibody libraries directly on cancer cell lines enables the identification of tumor-targeting antibodies without prior knowledge of target antigens (Liu et al. (2004) *Cancer Res.* 64: 704-710; Gao et al. (2003) *J. Immunol. Methods* 274: 185-197; Geuijen et al. (2005) *Eur. J. Cancer* 41: 178-187; Poul et al. (2000) *J. Mol. Biol.* 301: 1149-1161). Although numerous antibodies have been found by this approach, the screening process against cell lines does not provide an ideal picture as to how specific these antibodies will be to actual cancer cells in patient populations. After several generations in culture, cancer cell lines may express cell surface epitopes that differ from those present in the original cancerous tissue. Tissue sections from cancer patients would be an ideal selection target in the development of cancer-specific antibodies; however, most tissues taken during surgeries, biopsies, or autopsies are composed of heterogeneous cell populations. This seemingly poses a serious obstacle to selection methods that would specifically target cancer cells in tissue.

SUMMARY OF THE INVENTION

In certain embodiments this invention pertains to the development of a method that allows selection of antibodies against tumor cells in situ using laser capture microdissection. By restricting antibody selection to binders of internalizing epitopes, a panel of phage antibodies that target clinically represented prostate cancer antigens was generated.

Accordingly, in certain embodiments this invention provides an isolated antibody that specifically binds and, optionally, is internalized into a prostate cancer cell. In various embodiments the antibody is an antibody that specifically binds to an epitope that is specifically bound by bound an antibody selected from the group consisting of e.g., 3051.1, G12FC3, M6c42b, 4F3YW, M40pr146, UA20, UA8, 585I141, 585I141.1, 585I156, 3076, 3051, M49R, RCI-14, II79_4, II79_3, T5II-4B.1, T5II-4B.2, RCI-11, RCI-20, CI-11A, CI-14A, and/or S95-2. In various embodiments the antibody comprises one, two, or three complementarity determining regions (CDRs of the variable light (VL domain of an antibody selected from the group consisting of e.g., 3051.1, G12FC3, M6c42b, 4F3YW, M40pr146, UA20, UA8, 585I141, 585I141.1, 585I156, 3076, 3051, M49R, RCI-14, II79_4, II79_3, T5II-4B.1, T5II-4B.2, RCI-11, RCI-20, CI-11A, CI-14A, and/or S95-2; and/or one, two, or three complementarity determining regions (CDRs of the variable heavy (VH domain of an antibody selected from the group consisting of e.g., 3051.1, G12FC3, M6c42b, 4F3YW, M40pr146, UA20, UA8, 585I141, 585I141.1, 585I156, 3076, 3051, M49R, RCI-14, II79_4, II79_3, T5II-4B.1, T5II- 4B.2, RCI-11, RCI-20, CI-11A, CI-14A, and/or S95-2. In certain embodiments the antibody comprises the three VH CDRs and/or the three VL CDRs of an antibody selected from the group consisting of e.g., 3051.1, G12FC3, M6c42b, 4F3YW, M40pr146, UA20, UA8, 585I141, 585II41.1, 585II56, 3076, 3051, M49R, RCI-14, II79_4, II79_3, T5II-4B.1, T5II-4B.2, RCI-11, RCI-20, CI-11A, CI-14A, and/or S95-2. In certain embodiments the antibody comprises the VH domain and/or the VL domain of an antibody selected from the group consisting of e.g., 3051.1, G12FC3, M6c42b, 4F3YW, M40pr146, UA20, UA8, 585I141, 585II41.1, 585II56, 3076, 3051, M49R, RCI-14, II79_4, II79_3, T5II-4B.1, T5II-4B.2, RCI-11, RCI-20, CI-11A, CI-14A, and/or S95-2. In various embodiments the antibody is a single chain antibody. In certain embodiments the VL region is attached to the VH region by a (Gly$_4$Ser$_3$ SEQ ID NO:(SEQ ID NO:1) linker. In certain embodiments the antibody is an intact full antibody, a Fab, an (Fab')$_2$, an scFv, and an (ScFv'0$_2$, a unibody, or an affibody. In certain embodiments the antibody comprises a diabody. In certain embodiments the antibody is a single chain antibody selected from the group consisting of 3051.1, G12FC3, M6c42b, 4F3YW, M40pr146, UA20, UA8, 585I141, 585II41.1, 585II56, 3076, 3051, M49R, RCI-14, II79_4, II79_3, T5II-4B.1, T5II-4B.2, RCI-11, RCI-20, CI-11A, CI-14A, and S95-2.

In various embodiments chimeric moieties are provided comprising an effector attached to any one or more of the antibodies described herein. In certain embodiments the effector is selected from the group consisting of an epitope tag, a second antibody, a label, a cytotoxin, a liposome, a radionuclide, a drug, a prodrug, a viral particle, a cytokine, and a chelate. In certain embodiments the effector comprises an epitope tag selected from the group consisting of an avidin, and a biotin. In certain embodiments the effector comprises a cytotoxin selected from the group consisting of a Diphtheria toxin, a *Pseudomonas* exotoxin, a ricin, an abrin, and a thymidine kinase. In certain embodiments the effector comprises a chelate comprising a metal isotope selected from the group consisting of $^{99}$Tc, $^{203}$Pb, $^{67}$Ga, $^{68}$Ga, $^{72}$As, $^{111}$In, $^{113}$In, $^{97}$Ru, $^{62}$Cu, $^{641}$Cu, $^{52}$Fe, $^{52}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag. In certain embodiments the effector comprises an alpha emitter (e.g., bismuth 213). In certain embodiments the effector is a chelate comprising DOTA. In certain embodiments the effector comprises a lipid or a liposome.

Also provided are pharmaceutical formulations comprising a pharmaceutically acceptable excipient and an antibody or a chimeric moiety as described herein. In certain embodiments the pharmaceutical formulation of claim is a unit dosage formulation. In certain embodiments the pharmaceutical formulation is formulated for administration by a route such as intraperitoneal administration, intravenous injection, intramuscular injection, subcutaneous administration, direct administration to a tumor and/or surgical site, transcutaneous administration, subcutaneous depot formulation, oral administration, inhalation administration, rectal administration and the like.

In various embodiments methods are provided for delivering an effector to a prostate cancer cell. The methods typically involve administering to a cell, tissue, or organism, a composition comprising an antibody as described herein attached to an effector; whereby the antibody preferentially interacts with a prostate cancer cell thereby delivering the effector to the prostate cancer cell. In certain embodiments the preferentially interacting comprises being internalized by said cancer cell. In certain embodiments the effector comprises an anti-cancer agent and/or a detectable label. In certain embodiments the administering comprises administering to a human or to a non-human mammal. In certain embodiments the administering comprises administering parenterally. In certain embodiments the administering comprises administering into a tumor or a surgical site.

In various embodiments methods are provided for inhibiting the growth or proliferation of a prostate cancer cell. The methods typically involve contacting the cancer cell with an antibody as described herein and/or with a chimeric moiety comprising one or more antibodies as described herein attached to an anti-cancer drug (e.g., a lipid complexed with an anti-cancer drug, a liposome containing an anti-cancer drug, etc.), or a radionuclide. In certain embodiments the cancer cell is a metastatic cell. In certain embodiments the cancer cell is a solid tumor cell.

In certain embodiments methods are also provided for detecting a prostate cancer cell. The methods typically involve contacting the prostate cancer cell with a chimeric molecule comprising an antibody as described herein attached to a detectable label; and detecting the presence and/or location of said detectable label where the presence and/or location is an indicator of the location and/or presence of a prostate cancer cell. In certain embodiments the detectable label is selected from the group consisting of a gamma-emitter, a positron-emitter, an x-ray emitter, an alpha emitter, and a fluorescence-emitter. In certain embodiments the methods typically involve contacting a prostate cancer cell with a chimeric molecule comprising an antibody as described herein attached to an epitope tag; contacting the chimeric molecule with a chelate comprising a detectable moiety whereby the chelate binds to the epitope tag thereby associating said detectable moiety with the chelate; and detecting the detectable moiety where the presence and/or location of the detectable moiety is an indicator of the location and/or presence of a prostate cancer cell. In certain embodiments the detectable moiety or detectable label is a radionuclide. In certain embodiments the detectable moiety or detectable label is selected from the group consisting of a gamma-emitter, a positron-emitter, an alpha emitter, an x-ray emitter, and a fluorescence-emitter. In certain embodiments the detecting comprises external imaging. In certain embodiments the detecting comprises internal imaging. In certain embodiments the detectable moiety or detectable label comprises a metal isotope selected from the group consisting of to $^{99}$Tc, $^{203}$Pb, $^{67}$Ga, $^{68}$Ga, $^{72}$As, $^{111}$In, $^{113m}$In, $^{97}$Ru, $^{62}$Cu, $^{641}$Cu, $^{52}$Fe, $^{52m}$Mn, $^{51}$Cr, $^{186}$, Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{99m}$Tc, $^{105}$Rh, and $^{111}$Ag. In certain embodiments the chelate comprises DOTA. In certain embodiments the epitope tag is an avidin or a biotin.

Also provided are nucleic acids encoding an antibody as described herein. In various embodiments the nucleic acids comprise a vector and can be present in a cell whereby the cell expresses the antibody.

In various embodiments, this invention provides methods of identifying an antibody that preferentially binds to and/or is internalized by a target cell type that expresses a marker in vivo. The methods typically involve providing a display library (e.g., a yeast- or phage-display library); contacting a tissue compromising the cell type with members of the library; isolating groups of cells from the tissue using laser capture microdissection; and recovering members of the library that bind to cells in the isolated groups. In certain embodiments, the recovering comprises identifying members of the library that are internalized into cells in the isolated groups. In various embodiments, the target cell type is a pathological cell or a healthy cell characteristic of a particular tissue. In certain embodiments, the target cell type is a cancer cell (e.g., a cell of a cancer selected from the group consisting of a lung cancer, a bronchus cancer, a colorectal cancer, a prostate cancer, a breast cancer, a pancreas cancer, a stomach cancer, an ovarian cancer, a urinary bladder cancer, a brain or central nervous system cancer, a peripheral nervous system cancer, an esophageal cancer, a cervical cancer, a melanoma, a uterine or endometrial cancer, a cancer of the oral cavity or pharynx, a liver cancer, a kidney cancer, a biliary tract cancer, a small bowel or appendix cancer, a salivary gland cancer, a thyroid gland cancer, an adrenal gland cancer, an osteosarcoma, a chondrosarcoma, a liposarcoma, a testicular cancer, and a malignant fibrous histiocytoma). In certain embodiments the method involves counter-selecting the library on a normal cell population to reduce or eliminate members of the library that bind to normal cells. In certain embodiments, the providing comprises preselecting the library on a panel of tumor cell lines to create a library enriched for binders to functional cell surface epitopes on tumor cells. In certain embodiments, the preselecting is under internalizing conditions. In various embodiments, the recovering comprises amplifying a nucleic acid sequence encoding all or part of a displayed VH and/or VL domain from the bound or internalized members of the library.

DEFINITIONS

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644, 048), phosphorodithioate (Briu et al. (1989) *J. Am. Chem. Soc.* 111:2321, O-methylphosphoroamidite linkages (see Eckstein, Oligonucleotides and Analogues: A Practical Approach, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature*, 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469, 863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235, 033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "biotin" refers to biotin and modified biotins or biotin analogues that are capable of binding avidin or various avidin analogues. "Biotin", can be, inter alia, modified by the addition of one or more addends, usually through its free carboxyl residue. Useful biotin derivatives include, but are not limited to, active esters, amines, hydrazides and thiol groups that are coupled with a complimentary reactive group such as an amine, an acyl or alkyl group, a carbonyl group, an alkyl halide or a Michael-type acceptor on the appended compound or polymer.

Avidin, typically found in egg whites, has a very high binding affinity for biotin, which is a B-complex vitamin (Wilcheck et al. (1988) *Anal. Biochem,* 171:1). Streptavidin, derived from *Streptomyces avidinii*, is similar to avidin, but has lower non-specific tissue binding, and therefore often is used in place of avidin. As used herein "avidin" includes all of its biological forms either in their natural states or in their modified forms. Modified forms of avidin which have been treated to remove the protein's carbohydrate residues ("deglycosylated avidin"), and/or its highly basic charge ("neutral avidin"), for example, also are useful in the invention. Both avidin and streptavidin have a tetravalency for biotin, thus permitting amplification when the former bind to biotin. In certain embodiments, four detection or therapeutic agents, such as nuclides, can be attached to each targeting protein.

The term "residue" as used herein refers to natural, synthetic, or modified amino acids.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'₂, a dimer of Fab which itself is a light chain joined to $V_H$—$C_H1$ by a disulfide bond. The F(ab)'₂ may be reduced under mild conditions to break the disulfide linkage in the hinge region thereby converting the (Fab')₂ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$—$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies should include all that have been displayed on phage (e.g., scFv, Fv, Fab and disulfide linked Fv (Reiter et al. (1995) *Protein Eng.* 8: 1323-1331).

The term "specifically binds", as used herein, when referring to a biomolecule (e.g., protein, nucleic acid, antibody, etc.), refers to a binding reaction that is determinative of the presence biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

An "effector" refers to any molecule or combination of molecules whose activity it is desired to deliver/into and/or localize at cell. Effectors include, but are not limited to labels, cytotoxins, enzymes, growth factors, transcription factors, drugs, etc.

A "reporter" is an effector that provides a detectable signal (e.g. is a detectable label). In certain embodiments, the reporter need not provide the detectable signal itself, but can simply provide a moiety that subsequently can bind to a detectable label.

The term "conservative substitution" is used in reference to proteins or peptides to reflect amino acid substitutions that do not substantially alter the activity (specificity or binding affinity) of the molecule. Typically, conservative amino acid substitutions involve substitution of one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The terms "epitope tag" or "affinity tag" are used interchangeably herein, and used refers to a molecule or domain of a molecule that is specifically recognized by an antibody or other binding partner. The term also refers to the binding partner complex as well. Thus, for example, biotin or a biotin/avidin complex are both regarded as an affinity tag. In addition to epitopes recognized in epitope/antibody interactions, affinity tags also comprise "epitopes" recognized by other binding molecules (e.g. ligands bound by receptors), ligands bound by other ligands to form heterodimers or homodimers, $His_6$ bound by Ni-NTA, biotin bound by avidin, streptavidin, or anti-biotin antibodies, and the like.

Epitope tags are well known to those of skill in the art. Moreover, antibodies specific to a wide variety of epitope tags are commercially available. These include but are not limited to antibodies against the DYKDDDDK (SEQ ID NO:2) epitope, c-myc antibodies (available from Sigma, St. Louis), the HNK-1 carbohydrate epitope, the HA epitope, the HSV epitope, the $His_4$, $His_5$, and $His_6$ epitopes that are recognized by the H is epitope specific antibodies (see, e.g., Qiagen), and the like. In addition, vectors for epitope tagging proteins are commercially available. Thus, for example, the pCMV-Tag1 vector is an epitope tagging vector designed for gene expression in mammalian cells. A target gene inserted into the pCMV-Tag1 vector can be tagged with the FLAG® epitope (N-terminal, C-terminal or internal tagging), the c-myc epitope (C-terminal) or both the FLAG (N-terminal) and c-myc (C-terminal) epitopes.

BRIEF DESCRIPTION OF THE DRAWINGS

FIG. 5A: microscopic examination of uptake of UA20-ILs by PC3 and Du-145 cells. There was no uptake by BPH-1 cells. 5B: FACS analysis of uptake of UA20-DiIC18(3)-DS-ILs by Du-145 cells. MFI, mean fluorescence intensity. FIG. 5C: quantification of UA20 scFv-IL uptake by prostate cancer and control cells. MFI values were obtained from FACS. NT-LPs, non-targeted liposomes.

FIG. 6A shows that binding of the 585II41 scFv to prostate cancer cells was specifically competed by a previously identified anti-ALCAM scFv, H3, and its corresponding IgG1 but not by a control scFv, OA12, and its corresponding IgG1. FIG. 6B illustrates analysis of IP products by Western blot. Lysates from biotin surface-labeled Du-145 cells were incubated with 585II41 scFv and OA12 scFv (control) to generate IP products that were analyzed by Western blot using an ALCAM-specific commercial monoclonal antibody. Only the 585II41 scFv IP product reacted with the anti-ALCAM mAb. The band (indicated by an arrow) is located between 100 and 110 kDa. ALCAM is predicted to be a 65-kDa protein, but glycosylation causes it to appear as a band of ~105 kDa on SDS-PAGE, consistent with previous reports (Saifullah et al. (2004) *J. Immunol.* 173: 6125-6133). MFI, mean fluorescence intensity FIG. 7 shows the amino acid sequences of internalizing prostate cancer specific antibodies: 3051.1 (SEQ ID NO:3), G12FC3 (SEQ ID NO:4), M6c42b (SEQ ID NO:5), 4F3YW (SEQ ID NO:6), M40pr146 (SEQ ID NO:7), UA20 (SEQ ID NO:8), UA8 (SEQ ID NO:9), 585II41 (SEQ ID NO:10), 585II41.1 (SEQ ID NO:11), 585II56 (SEQ ID NO:12), 3076 (SEQ ID NO:13), and 3051 (SEQ ID NO:14).

FIG. 8 shows the amino acid sequences of internalizing prostate cancer specific antibodies: M49R (SEQ ID NO:15), RCI-14 (SEQ ID NO:16), II79_4 (SEQ ID NO:17), II79_3 (SEQ ID NO:18), T5II-4B.1 (SEQ ID NO:19), T5II-4B.2 (SEQ ID NO:20), RCI-11 (SEQ ID NO:21), RCI-20 (SEQ ID NO:22), CI-11A (SEQ ID NO:23), CI-14A (SEQ ID NO:24), and S95-2 (SEQ ID NO:25).

FIG. 10B: Biodistribution study. The values of % ID/g tissue for both the UA20 scFv and the control N3M2 scFv were plotted for tumor, blood and other organs/tissues. Standard errors are indicated. Sm.Int., small intestine. Lg.Int., large intestine. FIG. 10C: The ratio of % ID/g tissue (UA20 scFv over control N3M2 scFv) was plotted.

DETAILED DESCRIPTION

Much work has been done to develop tumor-targeting antibodies by selecting a phage antibody library on cancer cell lines. When tumor cells are removed from their natural environment, however, they may undergo genetic and epigenetic changes yielding different surface antigens than those seen in actual cases of cancer. In one embodiment, this invention pertains to a method that allows selection of phage antibodies against tumor cells in situ on fresh, fresh frozen, and paraffin-embedded tissues using laser capture microdissection. Laser capture microdissection (LCM) allows small clusters of homogenous cells to be isolated and removed from tissue sections under direct microscopic visualization. It was a surprising discovery that it is possible to exploit this technology for the selection of phage binding specifically to certain target (e.g., tumor) cells while ignoring adulterating entities such as non-neoplastic cells and stromal elements and that the resulting methods can be used to isolate, e.g., cancer cell specific antibodies that are internalized by the target cell(s).

Using the methods described herein, a number of antibodies were identified that target clinically represented prostate cancer antigens. We identified AL-CAM/MEMD/CD 166, a newly discovered prostate cancer marker, as the target for one of the selected antibodies, demonstrating the effectiveness of the approach. We further conjugated two single chain Fv fragments to liposomes and demonstrated that these nanotargeting devices were efficiently delivered to the interior of prostate cancer cells. The ability to deliver payload intracellularly and to recognize tumor cells in situ makes these antibodies attractive candidates for the development of targeted cancer therapeutics.

I. Selecting Phage Antibody Library on Cells In Situ Using Laser Capture Microdissection (LCM).

Much work has been done to develop tumor-targeting antibodies by selecting a phage antibody library on cancer cell lines. However, when tumor cells are removed from their natural environment, they may undergo genetic and epigenetic changes yielding different surface antigens than those seen in actual cases of cancer.

Figure 1:
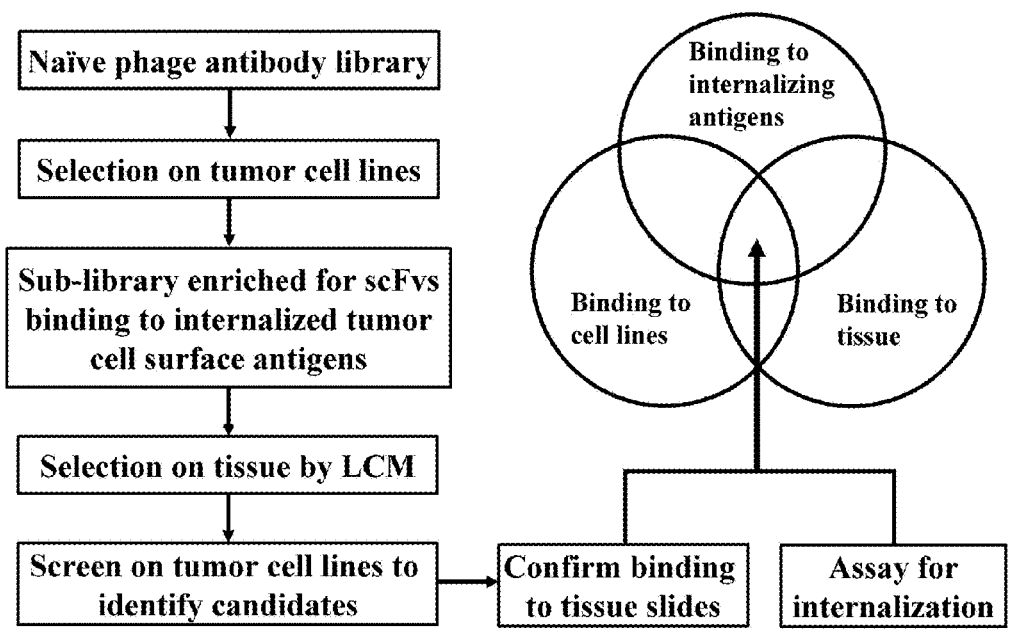
FIG. 1 schematically illustrates one embodiment, of a method of selecting antibodies according to the present invention. The naïve phage antibody library was first counterselected on a panel of non-tumorigenic cell lines to remove binders to common cell surface antigens (not shown) and then selected on live tumor cells under internalizing conditions to generate a sublibrary that is enriched for binders to internalizing cell surface epitopes. Further selection of this sublibrary on tissue slides by LCM enriched scFv fragments that bind to tumor cells in situ. Monoclonal phage antibodies were identified by screening selection output on tumor cell lines followed by rescreening positive clones on tissue slides. This selection scheme effectively restricts selection outcomes to phage antibodies that bind to epitopes present on both tumor cell lines and tumor cells in situ from actual cases. Moreover these antibodies are expected to possess internalizing functions that can be exploited for targeted payload delivery.
Figure 2:
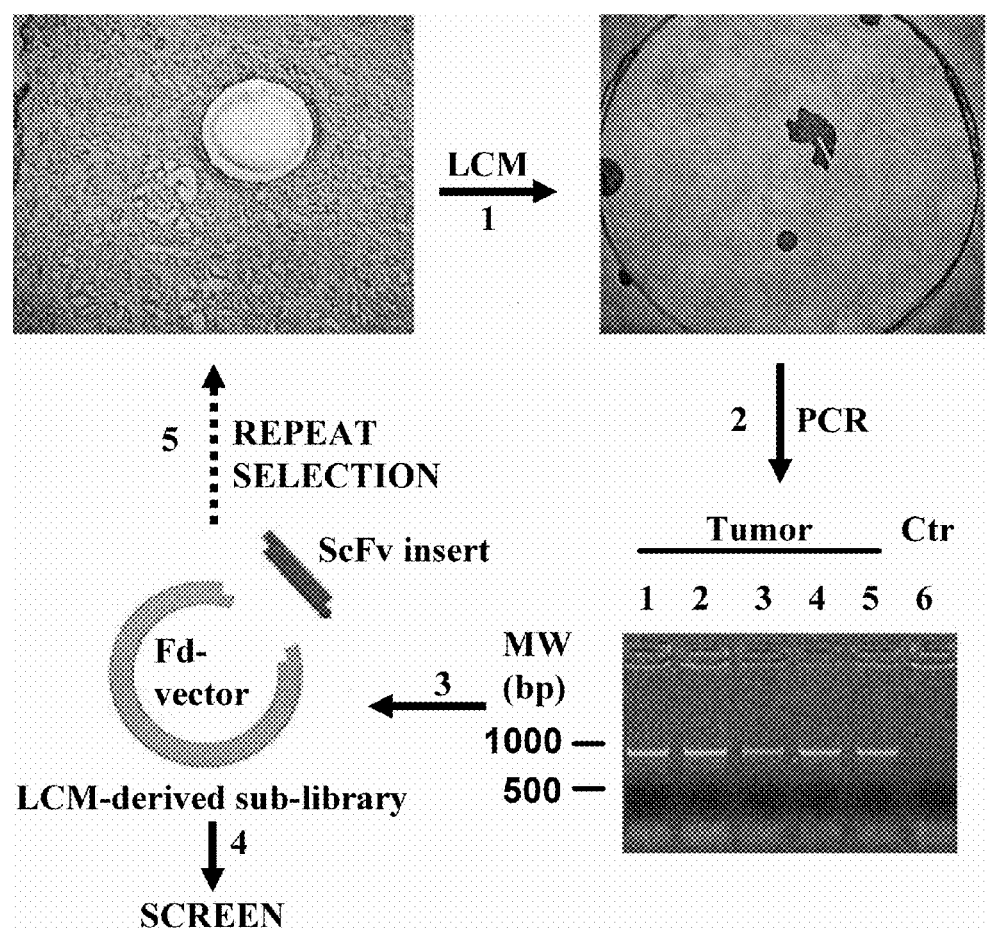
FIG. 2 illustrates selection of phage antibody library on tissue slides by LCM. Tissue pieces containing tumor cells and tumor-bound phage were procured by Leica AS LMD and collected on the cap of a PCR tube (step 1). scFv-coding regions were amplified by PCR (step 2) and spliced into a phage display vector to create LCM secondary libraries (step 3) that were used for screening (step 4) or additional rounds of selection (step 5). Ctr, control; MW, molecular weight.

We developed a strategy that allows selection of phage antibodies against tumor cells in situ, for example, of fresh samples, on frozen and paraffin-embedded tissues, and the like using laser capture microdissection (see, e.g., FIGS. 1 and 2). In various embodiments the methods involve providing a display library (e.g., a yeast- or phage-display library), contacting a tissue compromising the target type with members of the library; isolating groups of cells from the tissue using laser capture microdissection; and recovering members of the library that bind to cells in the isolated groups.

While the selection methods are described with respect to tumor cells/tissues, it will be recognized that using the LCM methods described herein, libraries can be used to screen for markers expressed in situ on essentially any desired cell type. Thus, for example, binders (e.g., antibodies) specific for any pathological cell type, where the pathological cell displays different markers, than other cells, can be identified.

Methods of providing display libraries (e.g., phage display, yeast-display, and the like) are well known to those of skill in the art (see, e.g., Boder et al. (1997) *Nat. Biotechnol.* 15: 553-557; Liu et al. (2004) *Cancer Res.* 64: 704-710; Poul et al. (2000) *J. Mol. Biol.* 301: 1149-1161; U.S. Pat. Nos. 6,699,658, and 6,696,251, and the like).

The display library can optionally be counter selected on cells for which binding is not desired (e.g., normal healthy cells) and/or pre-selected, e.g., on a panel of target cells to enhance the representation of binders and/or internalizing members in the library. In one illustrative embodiment, the library is created by selecting, e.g., a naïve phage antibody display library on a panel of target cells (e.g., tumor cell lines), and where internalization is desired, under internalizing conditions. Methods of preparation and selection of a phage antibody display library have been described, for example by Liu et al. (2004) *Cancer Res.* 64: 704-710, and Poul et al. (2000) *J. Mol. Biol.* 301: 1149-1161). In one illustrative example, (see, e.g., Example 1) the phage library is preincubated with a panel of non-tumorigenic cells including, for example BPH-1, human mammary epithelial cells, MCF10A, and human fibroblasts to remove binders to common cell surface antigens. The predepleted library can then, optionally be incubated with a panel of target cells (e.g., prostate cancer cell lines (PC3 and Du-145)) at 37° C. for 2 h; washed twice with 100 mM glycine, pH 2.8, in the presence of 150 mM NaCl; and washed once with PBS, pH 7.0. Internalized phage can be recovered by lysing the cells with 100 mM triethylamine, propagated in TG1, and purified by precipitation with polyethylene glycol 8000 as described previously (1), thereby creating a sublibrary that is enriched for binders to internalizing cell surface molecules.

The library can then be incubated (selected against) one or more tissues containing the target cells. Thus, for example, selections can be performed, on fresh, frozen, and/or paraffin embedded tissues. For selection on slides, for example, sections of the target tissue can be placed on microscope slides, and incubated with the library, for ½ to several hours, for example, at room temperature (e.g., 1 hour at room temperature). The tissue is then washed to remove unbound library members and prepared for laser capture microdissection according to standard methods.

Methods of performing laser capture microdissetion (LCM) are well known to those of skill in the art. The LCM technique is generally described by Emmert-Buck et al., (1996) *Science* 274: 998. In a typically LCM method, a transfer surface is placed onto the tissue section and then focally bonded to the targeted tissue, allowing it to be selectively removed for later analysis. In the microscope, the operator views the tissue and selects microscopic clusters of cells for analysis, then activates a laser within the microscope optics. The pulsed laser beam is absorbed within a precise spot on the transfer film immediately above the targeted cells. At this precise location, the film melts and fuses with the underlying cells of choice. When the film is removed, the chosen cells remain bound to the film, while the rest of the tissue is left behind. Manual, automated, as well as non-contact methods of LCM are well known and described, for example in U.S. Pat. Nos. 7,027,133, 6,897,038, 6,870,625, 6,690,470, and 6,469,779 (see, also, Murray and Curran (eds) (2005) *Laser Capture Microdissection: Methods and Protocols*, Humana Press, Inc. N.J.).

Typically 5-500, more typically 100 or 200, still more typically 20-100 or 20-50 cells are procured at a time, e.g., by generating a closed laser path around the group of cells of interest. The cells can then be collected (e.g., dropped into collection tubes by electrostatic force and gravity), and the bound and/or internalized library members recovered.

It was noted that phage bound to LCM-procured tissue pieces appear to lose the ability to infect bacteria, thereby posing a challenge to library selection. Little bacterial growth was observed under various culture conditions. This phenomenon was seen even in manually dissected tissue pieces that were not exposed to the UV laser used in the Leica LMD system. Exposure to ethanol during slide preparation for LCM seems to be a factor contributing to the observed reduction in phage viability.

Accordingly in certain embodiments the problem is circumvented by using the genomes of phages (or yeast) bound to the procured cancer cell pieces as templates for amplification of scFv genes, e.g., by PCR. The amplified scFv genes can easily be identified and/or sequenced.

The foregoing methods are intended to be illustrative an not limiting. Using the teaching provided herein other methods utilizing LCM in the screening and selection of binding libraries in situ will be available to one of skill in the art.

II. Internalizing Prostate Specific Antibodies.

In certain embodiments this invention provides a number of antibodies that specifically bind and are internalized into human prostate cancer cells. The antibodies were identified by selecting human antibody gene diversity libraries directly on the surface of prostate cancer cells in vivo using laser microdissection methods as described above and in the examples. Antibodies were identified that specifically bind and enter prostate cancer cells, with little or no binding to control cells.

For the selection process, the antibodies in the library were expressed as single chain Fv (scFv) antibodies comprising a variable heavy ($V_H$) region linked to a variable light ($V_L$) region by a peptide linker, although it will be recognized that using the antibody sequence presented herein other forms of the antibodies can be provided.

Representative antibodies (e.g. $V_H$ and $V_L$ domains) are illustrated in Tables 1 and 2, respectively as well as in FIGS. 7 and 8.

TABLE 1

Amino acid sequences of variable heavy (VH) chain of prostate cancer specific internalizing antibodies.

Heavy chain

| Clone | Frame 1 | CDR1 | Frame 2 | CDR2 | Frame 3 | CDR3 | Frame 4 |
|---|---|---|---|---|---|---|---|
| 3051.1 | QVQLQESGGGLVKPGGPLRLSCAASGFTFS (SEQ ID NO: 26) | SYGMY (SEQ ID NO: 27) | WVRQAPGKGLEWVS (SEQ ID NO: 28) | TLSRSGSGTYYADSVKG (SEQ ID NO: 29) | RFTISRDNSKNTLYLQMNSLRAEDTAVYYCAS (SEQ ID NO: 30) | IAVAGNYFDY (SEQ ID NO: 31) | WGQGTLVTVSS (SEQ ID NO: 32) |
| G12FC3 | QVQLVQSGGGVVQPGRSLRLSCAATGIPFS (SEQ ID NO: 33) | GSGMH (SEQ ID NO: 34) | WVRQAPGKGLEWVT (SEQ ID NO: 35) | MIWYDGSNKFYADSVKG (SEQ ID NO: 36) | RFTISRDNSKNTLYLQMDSLRAEDTAVYFCAR (SEQ ID NO: 37) | DKGVRSMDV (SEQ ID NO: 38) | WGLGTTVTVSS (SEQ ID NO: 39) |
| M6c42b | QVQLQESGGGLVQPGSLRLSCSASGFTFG (SEQ ID NO: 40) | TYAMR (SEQ ID NO: 41) | WVRQTSGKGLEWVS (SEQ ID NO: 42) | GIGVSGDAYYTDSVRG (SEQ ID NO: 43) | RFTISRDNSKNTLYLQMNTLRAEDTATYYCTR (SEQ ID NO: 44) | KSSTTSNDY (SEQ ID NO: 45) | WGRGTLVTVSS (SEQ ID NO: 46) |
| 4F3YW | QVQLQESGGGLVQPGGSLRLSCAASGFTFS (SEQ ID NO: 47) | SYAMH (SEQ ID NO: 48) | WVRQAPGKGLEWVA (SEQ ID NO: 49) | VISYDGSNKYYADSVKG (SEQ ID NO: 50) | RFTISRDNSKNTLYLQMNSLRAEDTAVYYCAR (SEQ ID NO: 51) | FSSGWYYFDY (SEQ ID NO: 52) | WGQGTLVTVSS (SEQ ID NO: 53) |
| M40pr164 | QVQLLQSGGGLVQPGGSLRLSCAASGFTFS (SEQ ID NO: 54) | SYAMS (SEQ ID NO: 55) | WVRQAPGKGLEWVS (SEQ ID NO: 56) | AISGSGGSTYYTDSVKG (SEQ ID NO: 57) | RFTISRDNSKNTLYLQMNSLRAEDTAVYYCAK (SEQ ID NO: 58) | SHDYGDYAGFDY (SEQ ID NO: 59) | WGQGTLVTVSS (SEQ ID NO: 60) |
| UA20 | QVQLQESGGGLVKPGGSLRLSCAASGFTFS (SEQ ID NO: 61) | NAWMN (SEQ ID NO: 62) | WVRQAPGKGLEWVG (SEQ ID NO: 63) | RIKSKTDEGTTDYAAPVKG (SEQ ID NO: 64) | RFSISRDDSKNTLYLQMNSLKTEDTGVYYCTA (SEQ ID NO: 65) | TKGLGGSK (SEQ ID NO: 66) | LGQGTLVTVSS (SEQ ID NO: 67) |
| UA8 | QVQLVESGGGVVQPGRSLRLSCAASGFTFS (SEQ ID NO: 68) | SFGMH (SEQ ID NO: 69) | WVRRAPGKGLEWVA (SEQ ID NO: 70) | VISYDGSNQYYADSVKG (SEQ ID NO: 71) | RFTISRDNSKNTLYLQMNSLRAEDTAVYYCGS (SEQ ID NO: 72) | RPGGGYASGSTVAY (SEQ ID NO: 73) | WGQGTPVTVSS (SEQ ID NO: 74) |
| 585II41 | QVQLVESGGGLVQPGGSLRLSCAASGF | SYAMG (SEQ ID NO: | WVRQAPGKGLEWVS | AISGSGGSTYYADSVKG | RFTISRDNSKDTLYLQMN | RSLLDY (SEQ ID NO: | WGQGTLVTV |

TABLE 1-continued

Amino acid sequences of variable heavy (VH) chain of prostate cancer specific internalizing antibodies.

Heavy chain

| Clone | Frame 1 | CDR1 | Frame 2 | CDR2 | Frame 3 | CDR3 | Frame 4 |
|---|---|---|---|---|---|---|---|
| | TFS (SEQ ID NO: 75) | ID (SEQ ID NO: 76) | (SEQ ID NO: 77) | (SEQ ID NO: 78) | SLRAED TAVYYC AS (SEQ ID NO: 79) | ID NO: 80) | SS (SEQ ID NO: 81) |
| 585II41.1 | QVQLVESGG GLVQPGGSL RLSCAASGF TFS (SEQ ID NO: 82) | SYAM S (SEQ ID NO: 83) | WVRQAP GKGLEW VS (SEQ ID NO: 84) | AISGSG GSTYYA DSVKG (SEQ ID NO: 85) | RFTISR DNSKDT LYLQMN SLRAED TAVYYC AS (SEQ ID NO: 86) | RSLL DY (SEQ ID NO: 87) | WGQ GTL VTV SS (SEQ ID NO: 88) |
| 585II56 | QVQLQESGG GLVQLGGSL RLSCAASGF TFS (SEQ ID NO: 89) | SYAM S (SEQ ID NO: 90) | WVRQAP GKGLEW VS (SEQ ID NO: 91) | AISGSG GSTYYA DSVKG (SEQ ID NO: 92) | RFTISR DNSKNT LYLQMS SLRAED TAFYYC AN (SEQ ID NO: 93) | SAYT GGWY DY (SEQ ID NO: 94) | WGH GTL VTV SS (SEQ ID NO: 95) |
| 3076 | QVNLRESGG GLVQPGGFL RLSCAAFGF TFS (SEQ ID NO: 96) | GYWM S (SEQ ID NO: 97) | WVHPAP GKGLEW VA (SEQ ID NO: 98) | NIKQDG SEKFYV DSVKG (SEQ ID NO: 99) | RFTISR DNAKNS LFLQMN SLRAED TAVYFC AR (SEQ ID NO: 100) | GLLS DY (SEQ ID NO: 101) | WGQ GTL VPV SS (SEQ ID NO: 102) |
| 3051 | QVQLQESGG GLVKPGGPL RLSCAASGF TFS (SEQ ID NO: 103) | SYGM Y (SEQ ID NO: 104) | WVRQAP GKGLEW VS (SEQ ID NO: 105) | TLSRSG SGTYYA ESVKG (SEQ ID NO: 106) | RFTISR DNSKNT LYFQMN SLRAED TAVYYC AS (SEQ ID NO: 107) | IAVA GNYF EY (SEQ ID NO: 108) | WGQ GTL VTV SS (SEQ ID NO: 109) |
| M49R | QVQLQESGG GLVKPGESL RLSCAASGF TFS (SEQ ID NO: 110) | DHYM D (SEQ ID NO: 111) | WVRQAP GKGLEW VA (SEQ ID NO: 112) | YIRYDG STKYYA DSVKG (SEQ ID NO: 113) | RFTISR DNSKNT LYLQMN SLRPED TAFYYC AR (SEQ ID NO: 114) | LIAE AEGW FDP (SEQ ID NO: 115) | WGQ GTL VTV SS (SEQ ID NO: 116) |
| RCI-14 | QVQLLQSAG GLVQPGGSL RLSCAASGF TFS (SEQ ID NO: 117) | TYAM N (SEQ ID NO: 118) | WVRQAP GKGLEW VS (SEQ ID NO: 119) | GISGSG GSTNYA DSVKG (SEQ ID NO: 120) | RFTISR DSSKNT LFLQMN SLRAED TAVYYC AK (SEQ ID NO: 121) | DYGS GWYD Y (SEQ ID NO: 122) | WGQ GTL VTV SS (SEQ ID NO: 123) |
| II79_4 | QVQLVESGG GLVQPGGSL RLSCAASGF TFS (SEQ ID NO: 124) | SYAM S (SEQ ID NO: 125) | WVHQAP GKGLEW VS (SEQ ID NO: 126) | AISGSG GSTYYA DSVKG (SEQ ID NO: 127) | RFTISR DNSKNT LYLQMN SLRAED TAVYYC AK | TYYG FWSG YYDY (SEQ ID NO: | LGQ GTL VTV SS (SEQ ID |

TABLE 1-continued

Amino acid sequences of variable heavy (VH) chain of prostate cancer specific internalizing antibodies.

Heavy chain

| Clone | Frame 1 | CDR1 | Frame 2 | CDR2 | Frame 3 | CDR3 | Frame 4 |
|---|---|---|---|---|---|---|---|
| | | | | | (SEQ ID NO: 128) | 129) | NO: 130) |
| II79_3 | QVQLLESGG GVVQPGTSL RLSCAASGF TFS (SEQ ID NO: 131) | NYAI N (SEQ ID NO: 132) | WVRQAA GKGLEW VS (SEQ ID NO: 133) | GISGSG VSTSYA DSVKG (SEQ ID NO: 134) | RFTVSR DNSKNT LYLQMN SLRVED TALYYC AK (SEQ ID NO: 135) | NGGG PEYL QH (SEQ ID NO: 136) | WGQ GTL VTV SS (SEQ ID NO: 137) |
| T5II-4B.1 | QVQLQESGG TLVQPGGSL RLSCAASGF TFS (SEQ ID NO: 138) | SYAM S (SEQ ID NO: 139) | WVRQAP GRGLEW VS (SEQ ID NO: 140) | TISGSG GSTYYA DSVKG (SEQ ID NO: 141) | RFTISR DNSKNT LYLQMN SLRAED TAVYYC AK (SEQ ID NO: 142) | GAYS GSY (SEQ ID NO: 143) | WGQ GTL VTV SS (SEQ ID NO: 144) |
| T5II-4B.2 | QVQLQESGG TLVQPGGSL RLSCAASGF TFS (SEQ ID NO: 145) | SYAM S (SEQ ID NO: 146) | WVRQAP GRGLEW VS (SEQ ID NO: 147) | TISGSG GSTYYA DSVKG (SEQ ID NO: 148) | RFTISR DNSKNT LYLQMN SLRAED TAVYYC AK (SEQ ID NO: 149) | GAYS GSH (SEQ ID NO: 150) | WGQ GTL VTV SS (SEQ ID NO: 151) |
| RCI-11 | QVQLVESGA EVKKPGASV KVSCKASGY TFT (SEQ ID NO: 152) | SYGI S (SEQ ID NO: 153) | WVRQAP GQGLEW MG (SEQ ID NO: 154) | WISAYN GNTNYA QKLQG (SEQ ID NO: 155) | RVTMTT DTSTST AYMELR SLRSDD TAVYYC AR (SEQ ID NO: 156) | PIYD SSGY DAFD I (SEQ ID NO: 157) | WGQ GTM VTV SS (SEQ ID NO: 158) |
| RCI-20 | QVQLVESGG GLVKPGGSL RLSCAASGF TFS (SEQ ID NO: 159) | SYAM H (SEQ ID NO: 160) | WVRQAP GKGLEW VA (SEQ ID NO: 161) | VISYDG SNKYYA DSVKG (SEQ ID NO: 162) | RFTISR DNSKNT LYLQMN SLRAED TAVYFC VR (SEQ ID NO: 163) | PSDS GWSF EH (SEQ ID NO: 164) | WGQ GTL VPV SS (SEQ ID NO: 165) |
| CI-11A | <u>QVQLQESGG GLVQPGGSL RLSCAASGF TFS</u> (SEQ ID NO: 166) | <u>SYAM S</u> (SEQ ID NO: 167) | <u>WVRQAP GKGLEW VA</u> (SEQ ID NO: 168) | <u>VISYDG SNKYYA DSVKG</u> (SEQ ID NO: 169) | <u>RFTISR DNSKNT LYLQMN SLRAED TAVYYC VR</u> (SEQ ID NO: 170) | <u>GDRS YGAE YFQH</u> (SEQ ID NO: 171) | <u>WGQ GTL VTV SS</u> (SEQ ID NO: 172) |
| CI-14A | <u>QVQLQESGG GLVKPGGSL RLSCAASGF TSS</u> (SEQ ID NO: 173) | <u>SYAM H</u> (SEQ ID NO: 174) | <u>WVRQAP GKGLEY VS</u> (SEQ ID NO: 175) | <u>AIGGNG GTYYAD SVKG</u> (SEQ ID NO: 176) | <u>RFTISR DNSKNT LYLQMN SLRAED TAVYYC AK</u> (SEQ ID NO: 177) | <u>EGEQ WLEY RYYY GMDV</u> (SEQ ID NO: 178) | <u>WGQ GTT VTV SS</u> (SEQ ID NO: 179) |

TABLE 1-continued

Amino acid sequences of variable heavy (VH) chain of prostate cancer specific internalizing antibodies.

Heavy chain

| Clone | Frame 1 | CDR1 | Frame 2 | CDR2 | Frame 3 | CDR3 | Frame 4 |
|---|---|---|---|---|---|---|---|
| S95-2 | QVQLVESGG GVVQPGRSL RLSCTASGF TFS (SEQ ID NO: 180) | SYGM H (SEQ ID NO: 181) | WVRQAP GKGLEW VA (SEQ ID NO: 182) | VISYDG SNKYYA DSVKG (SEQ ID NO: 183) | RFTISR DNSKNT LYLQMN SLRAED TAVYYC AR (SEQ ID NO: 184) | GGRY SSNW FSYY YYGM DV (SEQ ID NO: 185) | WGQ GTT VTV SS (SEQ ID NO: 186) |

TABLE 2

Amino acid sequences of variable light (VL) chain of prostate cancer specific internalizing antibodies.

| Light Chain Clone | Frame 1 | CDR1 | Frame 2 | CDR2 | Frame 3 | CDR3 | Frame 4 |
|---|---|---|---|---|---|---|---|
| 3051.1 | SYVLTQDPA VSVALGQTV RITC (SEQ ID NO: 187) | QGDS LRSY YAS (SEQ ID NO: 188) | WYQERP GQAPLL VI (SEQ ID NO: 189) | YGKN NRPS (SEQ ID NO: 190) | GIPDRFS GSNSGST ATLTISR VEAGDEG DYYC (SEQ ID NO: 191) | QVWD SINE QVV (SEQ ID NO: 192) | FGGG TKVT VL (SEQ ID NO: 193) |
| G12FC3 | NFMLTQPPS VSVAPGQTA KITC (SEQ ID NO: 194) | DGYS IRTK SVH (SEQ ID NO: 195) | WYQQKP GQAPVV VV (SEQ ID NO: 196) | HDDS DRPS (SEQ ID NO: 197) | GIPERFS GSNSGTT ATLTISR VEAGDEA DYYC (SEQ ID NO: 198) | QAWD SISE EVV (SEQ ID NO: 199) | FGGG TKLT VL (SEQ ID NO: 200) |
| M6c42b | SYVLTQDPA VSVALGQTV RITC (SEQ ID NO: 201) | QGDN IGSK SVH (SEQ ID NO: 202) | WYQQKP GQAPVL VV (SEQ ID NO: 203) | YDDS DRPS (SEQ ID NO: 204) | GIPERFS GSNSGTT ATLTISS VEAGDEA DYYC (SEQ ID NO: 205) | QAWD SISE HVI (SEQ ID NO: 206) | FGGG TKVT VL (SEQ ID NO: 207) |
| 4F3YW | DIQMTQSPS FLSASVGDR ITITC (SEQ ID NO: 208) | RASH DISS YFA (SEQ ID NO: 209) | WYQQKP GKAPKP LI (SEQ ID NO: 210) | YAAS TLQS (SEQ ID NO: 211) | GVPSRFS GSGSGTE FTLTISS LQPEDFA TYYC (SEQ ID NO: 212) | QQLG SYPL T (SEQ ID NO: 213) | FGGG TKLE IK (SEQ ID NO: 214) |
| M40pr146 | HVILTQDPA VSVALGQTV RITC (SEQ ID NO: 215) | QGDS LKSY YAS (SEQ ID NO: 216) | WYQQKP GQAPVL VI (SEQ ID NO: 217) | YGKN NRPS (SEQ ID NO: 218) | GIPDRFS GSSSGTT ASLTITG AQAEDEA DYYC (SEQ ID NO: 219) | HSRD SSGT HLRV (SEQ ID NO: 220) | FGGG TKLT VL (SEQ ID NO: 221) |
| UA20 | QSVLTQPPS ASGTPGQRV TISC (SEQ ID NO: 222) | SGSS SNIG NNTV N (SEQ ID NO: 223) | WSRQLP GTAPKL LI (SEQ ID NO: 224) | YSND QRPS (SEQ ID NO: 225) | GVPDRFS GSKSGTS ASLAITG LQPEDEA DYYC (SEQ ID NO: 226) | GTWD SSLS AYV (SEQ ID NO: 227) | FGTG TKLT VL (SEQ ID NO: 228) |

TABLE 2-continued

Amino acid sequences of variable light (VL) chain of prostate cancer specific internalizing antibodies.

| Light Chain Clone | Frame 1 | CDR1 | Frame 2 | CDR2 | Frame 3 | CDR3 | Frame 4 |
|---|---|---|---|---|---|---|---|
| UA8 | SSELTQDPA VSVALGQTV RITC (SEQ ID NO: 229) | QGDS LRSY YAS (SEQ ID NO: 230) | WYQQKP GQAPLL VI (SEQ ID NO: 231) | YGQN IRPS (SEQ ID NO: 232) | GIPDRFS GSSSGNS ASLTITG AQAEDEA DYYC (SEQ ID NO: 233) | HSRD SSGK YV (SEQ ID NO: 234) | FGVG TKVT VL (SEQ ID NO: 235) |
| 585II41 | NFMLTQDPA VSVALGQTV RITC (SEQ ID NO: 236) | QGDS LRSY YAS (SEQ ID NO: 237) | WYQQKP GQAPLL VI (SEQ ID NO: 238) | YGKN NRPS (SEQ ID NO: 239) | GIPDRFS GSSSGNT ASLTITG AQAEDEA DYYC (SEQ ID NO: 240) | NSRD SSGN PV (SEQ ID NO: 241) | FGGG TKVT VL (SEQ ID NO: 242) |
| 585II41.1 | NFMLTQDPA VSVALGQTV RITC (SEQ ID NO: 243) | QGDS LRSY YAS (SEQ ID NO: 244) | WYQQKP GQAPLL VI (SEQ ID NO: 245) | YGKN NRPS (SEQ ID NO: 246) | GIPDRFS GSSSGNT ASLTITG AQAEDEA DYYC (SEQ ID NO: 247) | NSRD SSGN PV (SEQ ID NO: 248) | FGGG TKVT VL (SEQ ID NO: 249) |
| 585II56 | SSELTQDPA VSVALGQTV KITC (SEQ ID NO: 250) | QGDS LRTY YAS (SEQ ID NO: 251) | WYQQRP GQAPVL VI (SEQ ID NO: 252) | YGEN SRPS (SEQ ID NO: 253) | GIPDRFS GSSSGNT ASLTITG AQAEDEA DYYC (SEQ ID NO: 254) | NSRD SSGN HLRV (SEQ ID NO: 255) | FGGG TKLT VL (SEQ ID NO: 256) |
| 3076 | NFMLTQPPS VSVAPGKTA SLTC (SEQ ID NO: 257) | GGYN IGTK SVH (SEQ ID NO: 258) | WYQQKP GQAPVV VV (SEQ ID NO: 259) | HDDS DRPS (SEQ ID NO: 260) | GIPERFS GSNSGTT ATLTIIR VEAGDEA DYYC (SEQ ID NO: 261) | QAWD SISE EVV (SEQ ID NO: 262) | FGGG TKLT VL (SEQ ID NO: 263) |
| 3051 | SYVLTQDPA VSVALGQTV RITC (SEQ ID NO: 264) | QGDS LRSY YAS (SEQ ID NO: 265) | WYQERP GQAPLL VI (SEQ ID NO: 266) | YGKN NRPS (SEQ ID NO: 267) | GIPDRFS GSNSGST ATLTISR VEAGDEG DYYC (SEQ ID NO: 268) | QVWD SINE QVV (SEQ ID NO: 269) | FGGG TKVT VL (SEQ ID NO: 270) |
| M49R | NFMLTQPPS VSVAPGKTA RITC (SEQ ID NO: 271) | GGNN IGSK SVY (SEQ ID NO: 272) | WYQQKP GQAPVL VV (SEQ ID NO: 273) | YDDS DRPS (SEQ ID NO: 274) | GIPERFS GSNSGNT ATLTISR VEAGDEA DYYC (SEQ ID NO: 275) | QVWD SSSD HVV (SEQ ID NO: 276) | FGGG TKVT VL (SEQ ID NO: 277) |
| RCI-14 | SSELTQDPA VSVALGQTV RITC (SEQ ID NO: 278) | QGDS LRSY YAS (SEQ ID NO: 279) | WYQERP GQAPLL VI (SEQ ID NO: 280) | YGRN ERPS (SEQ ID NO: 281) | GIPDRFS ASSSGNT ASLTITG AQAEDEA DYYC (SEQ ID NO: 282) | QVWD SFNE QVV (SEQ ID NO: 283) | FGGG TKLT VL (SEQ ID NO: 284) |
| II79_4 | SSELTQDPA VSVALGQTV TITC (SEQ ID NO: 285) | QGDS LRSY YAN (SEQ ID NO: 286) | WYQQKP GQAPIL VI (SEQ ID NO: 287) | YGEN NRPS (SEQ ID NO: 288) | GIPDRFS GSSSGNT ASLTITG AQAEDEA DYYC (SEQ ID NO: 289) | HSRD SSGT HLRV (SEQ ID NO: 290) | FGGG TKLT VL (SEQ ID NO: 291) |

TABLE 2-continued

Amino acid sequences of variable light (VL) chain of prostate cancer specific internalizing antibodies.

| Light Chain Clone | Frame 1 | CDR1 | Frame 2 | CDR2 | Frame 3 | CDR3 | Frame 4 |
|---|---|---|---|---|---|---|---|
| II79_3 | QSVLTQPPS ASGTPGQRV TISC (SEQ ID NO: 292) | SGSS SNIG NNTV N (SEQ ID NO: 293) | WSRQLP GTAPKL LI (SEQ ID NO: 294) | YSND QRPS (SEQ ID NO: 295) | GVPDRFS GSKSGTS ASLAITG LQPEDEA DYYC (SEQ ID NO: 296) | GTWD SSLS AYV (SEQ ID NO: 297) | FGTG TKLT VL (SEQ ID NO: 298) |
| T5II-4B.1 | SSELTQDPA VSVALGQTV RITC (SEQ ID NO: 299) | QGDS LRSY YAS (SEQ ID NO: 300) | WYQQKP GQAPSL VI (SEQ ID NO: 301) | YGEN SRPS (SEQ ID NO: 302) | GIPDRFS GSSSGNT ASLTITG AQAENEA DYYC (SEQ ID NO: 303) | QAWD SSTA VV (SEQ ID NO: 304) | FGGG TKLT VL (SEQ ID NO: 305) |
| T5II-4B.2 | SSELTQDPA VSVALGQTV RITC (SEQ ID NO: 306) | QGDS LRSY YAS (SEQ ID NO: 307) | WYQQKP GQAPSL VI (SEQ ID NO: 308) | YGEN SRPS (SEQ ID NO: 309) | GIPDRFS GSSSGNT ASLTITG AQAENEA DYYC (SEQ ID NO: 310) | QAWD SSTA VV (SEQ ID NO: 311) | FGGG TKLT VL (SEQ ID NO: 312) |
| RCI-11 | DIVMTQSPS TLSASIGDR VTITC (SEQ ID NO: 313) | RASE GIYH WLA (SEQ ID NO: 314) | WYQQKP GKAPKL LI (SEQ ID NO: 315) | YKAS SLAS (SEQ ID NO: 316) | GAPSRFS GSGSGTD FTLTISS LQPDDFA TYYC (SEQ ID NO: 317) | QQYH TISR T (SEQ ID NO: 318) | FGPG TKVD IK (SEQ ID NO: 319) |
| RCI-20 | QSVLTQPPS ASGTPGQRV TISC (SEQ ID NO: 320) | SGSS SNIG NNTV N (SEQ ID NO: 321) | WSRQLP GTAPKL LI (SEQ ID NO: 322) | YSND QRPS (SEQ ID NO: 323) | GVPDRFS GSKSGTS ASLAITG LQPEDEA DYYC (SEQ ID NO: 324) | GTWD SSLS AYV (SEQ ID NO: 325) | FGTG TKLT VL (SEQ ID NO: 326) |
| CI-11A | SSELTQDPA VSVASGQTV RITC (SEQ ID NO: 327) | QGDS LRSY YAS (SEQ ID NO: 328) | WYQQKP GQAPLL VI (SEQ ID NO: 329) | YGKN IRPS (SEQ ID NO: 330) | GIPDRFS GSTSGNS ASLTITG AQAEDEA DYYC (SEQ ID NO: 331) | NSRD SSGN RNWV (SEQ ID NO: 332) | FGGG TKLT VL (SEQ ID NO: 333) |
| CI-14A | SSELTQDPA VSVALGQTV RITC (SEQ ID NO: 334) | QGDS LRSY YAS (SEQ ID NO: 335) | WYQQKP GQAPSL VI (SEQ ID NO: 336) | YGEN SRPS (SEQ ID NO: 337) | GIPDRFS GSSSGNT ASLTITG AQAENEA DYYC (SEQ ID NO: 338) | QAWD SSTA VV (SEQ ID NO: 339) | FGGG TKLT VL (SEQ ID NO: 340) |
| S95-2 | NFMLTQPPS VSVAPGKTA RITC (SEQ ID NO: 341) | GGNN IGSK SVY (SEQ ID NO: 342) | WYQQKP GQAPVL VV (SEQ ID NO: 343) | YDDS DRPS (SEQ ID NO: 344) | GIPERFS GSNSGNT ATLTISR VEAGDEA DYYC (SEQ ID NO: 345) | QVWD SSSD HVV (SEQ ID NO: 346) | FGGG TKVT VL (SEQ ID NO: 347) |

In certain embodiments, for single chain Fv antibodies the variable heavy (VH) region is coupled to the variable light (V$_L$) either directly, or more preferably by a peptide linker (e.g., (Gly$_4$Ser)$_3$, SEQ ID NO:350). Illustrative scFv antibodies are shown in Table 3.

Using the sequence information provided in Tables 1, 2, and/or 3, and/or in FIGS. 7 and 8 the antibodies 3051.1, G12FC3, M6c42b, 4F3YW, M40pr146, UA20, UA8, 585II41, 585II41.1, 585II56, 3076, 3051, M49R, RCI-14, II79_4, II79_3, T5II-4B.1, T5II-4B.2, RCI-11, RCI-20, CI-11A, CI-14A, and S95-2, or antibodies comprising one or more of the CDRs comprising these antibodies, or antibodies comprising the VH and/or VL domain(s) of these antibodies can readily be prepared using standard methods (e.g. chemical synthesis methods and/or recombinant expression methods) well known to those of skill in the art.

In addition, other "related" prostate cancer specific antibodies can be identified by screening for antibodies that bind to the same epitope (e.g. that compete with the listed antibodies for binding to a prostate cancer cell) and/or by modification of the antibodies identified herein (e.g., 3051.1, G12FC3, M6c42b, 4F3YW, M40pr146, UA20, UA8, 585II41, 585II41.1, 585II56, 3076, 3051, M49R, RCI-14, II79_4, II79_3, T5II-4B.1, T5II-4B.2, RCI-11, RCI-20, CI-11A, CI-14A, and/or S95-2) to produce libraries of modified antibody and then rescreening antibodies in the library for improved binding to prostate cancer cells, and/or by screening of various libraries on prostate cancer cells, e.g., as illustrated in Example 1.

TABLE 3

Illustrative scFv antibodies. The VL and VH regions are joined by a (Gly4Ser)3 (SEQ ID NO: 1) linker (shown underlined).

| Clone | Amino Acid Sequence | SEQ ID No |
|---|---|---|
| 3051.1 | QVQLQESGGGLVKPGGPLRLSCAASGFTFSSYGMYW VRQAPGKGLEWVSTLSRSGSGTYYADSVKGRFTISR DNSKNTLYLQMNSLRAEDTAVYYCASIAVAGNYFDY WGQGTLVTVSSGGGGSGGGGSGGGGSSYVLTQDPAV SVALGQTVRITCQGDSLRSYYASWYQERPGQAPLLV IYGKNNRPSGIPDRFSGSNSGSTATLTISRVEAGDE GDYYCQVWDSINEQVVFGGGTKVTVL | 3 |
| G12FC3 | QVQLVQSGGGVVQPGRSLRLSCAATGIPFSGSGMHW VRQAPGKGLEWVTMIWYDGSNKFYADSVKGRFTISR DNSKNTLYLQMDSLRAEDTAVYFCARDKGVRSMDVW GLGTTVTVSSGGGGSGGGGSGGGGSNFMLTQPPSVS VAPGQTAKITCDGYSIRTKSVHWYQQKPGQAPVVVV HDDSDRPSGIPERFSGSNSGTTATLTISRVEAGDEA DYYCQAWDSISEEVVFGGGTKLTVL | 4 |
| M6c42b | QVQLQESGGGLVQPGGSLRLSCSASGFTFGTYAMRW VRQTSGKGLEWVSGIGVSGDAYYTDSVRGRFTISRD NSKNTLYLQMNTLRAEDTATYYCTRKSSTTSNDYWG RGTLVTVSSGGGGSGGGGSGGGGSSYVLTQDPAVSV ALGQTVRITCQGDNIGSKSVHWYQQKPGQAPVLVVY DDSDRPSGIPERFSGSNSGTTATLTISSVEAGDEAD YYCQAWDSISEHVIFGGGTKVTVL | 5 |
| 4F3YW | QVQLQESGGGLVQPGGSLRLSCAASGFTFS<u>SYAMHW</u> VRQAPGKGLEWVAVISYDGSNKYYADSVKGRFTISR DNSKNTLYLQMNSLRAEDTAVYYCARFSSGWYYFDY WGQGTLVTVSSGGGGSGGGGSGGGGSDIQMTQSPSF LSASVGDRITITCRASHDISSYFAWYQQKPGKAPKP LIYAASTLQSGVPSRFSGSGSGTEFTLTISSLQPED FATYYCQQLGSYPLTFGGGTKLEIK | 6 |
| M40pr146 | QVQLLQSGGGLVQPGGSLRLSCAASGFTFSSYAMSW VRQAPGKGLEWVSAISGSGGSTYYTDSVKGRFTISR DNSKNTLYLQMNSLRAEDTAVYYCAKSHDYGDYAGF DYWGQGTLVTVSSGGGGSGGGGSGGGGSHVILTQDP AVSVALGQTVRITCQGDSLKSYYASWYQQKPGQAPV LVIYGKNNRPSGIPDRFSGSSSGTTASLTITGAQAE DEADYYCHSRDSSGTHLRVFGGGTKLTVL | 7 |
| UA20 | QVQLQESGGGLVKPGGSLRLSCAASGFTFSNAWMNW VRQAPGKGLEWVGRIKSKTDEGTTDYAAPVKGRFSI SRDDSKNTLYLQMNSLKTEDTGVYYCTATKGLGGSK LGQGTLVTVSSGGGGSGGGGSGGGGSQSVLTQPPSA SGTPGQRVTISCSGSSSNIGNNTVNWSRQLPGTAPK LLIYSNDQRPSGVPDRFSGSKSGTSASLAITGLQPE DEADYYCGTWDSSLSAYVFGTGTKVTVL | 8 |

TABLE 3-continued

Illustrative scFv antibodies. The VL and VH regions are joined by a (Gly4Ser)3 (SEQ ID NO: 1) linker (shown underlined).

| Clone | Amino Acid Sequence | SEQ ID No |
|---|---|---|
| UA8 | QVQLVESGGGVVQPGRSLRLSCAASGFTFSSFGMHW VRRAPGKGLEWVAVISYDGSNQYYADSVKGRFTISR DNSKNTLYLQMNSLRAEDTAVYYCGSRPGGGYASGS TVAYWGQGTPVTVSSGGGGSGGGGSGGGGSSSELTQ DPAVSVALGQTVRITCQGDSLRSYYASWYQQKPGQA PLLVIYGQNIRPSGIPDRFSGSSSGNSASLTITGAQ AEDEADYYCHSRDSSGKYVFGVGTKVTVL | 9 |
| 585II41 | QVQLVESGGGLVQPGGSLRLSCAASGFTFSSYAMGW VRQAPGKGLEWVSAISGSGGSTYYADSVKGRFTISR DNSKDTLYLQMNSLRAEDTAVYYCASRSLLDYWGQG TLVTVSSGGGGSGGGGSGGGGSNFMLTQDPAVSVAL GQTVRITCQGDSLRSYYASWYQQKPGQAPLLVIYGK NNRPSGIPDRFSGSSSGNTASLTITGAQAEDEADYY CNSRDSSGNPVFGGGTKVTVL | 10 |
| 585II41.1 | QVQLVESGGGLVQPGGSLRLSCAASGFTFSSYAMSW VRQAPGKGLEWVSAISGSGGSTYYADSVKGRFTISR DNSKDTLYLQMNSLRAEDTAVYYCASRSLLDYWGQG TLVTVSSGGGGSGGGGSGGGGSNFMLTQDPAVSVAL GQTVRITCQGDSLRSYYASWYQQKPGQAPLLVIYGK NNRPSGIPDRFSGSSSGNTASLTITGAQAEDEADYY CNSRDSSGNPVFGGGTKVTVL | 11 |
| 585II56 | QVQLQESGGGLVQLGGSLRLSCAASGFTFSSYAMSW VRQAPGKGLEWVSAISGSGGSTYYADSVKGRFTISR DNSKNTLYLQMSSLRAEDTAFYYCANSAYTGGWYDY WGHGTLVTVSSGGGGSGGGGSGGGGSSSELTQDPAV SVALGQTVKITCQGDSLRTYYASWYQQRPGQAPVLV IYGENSRPSGIPDRFSGSSSGNTASLTITGAQAEDE ADYYCNSRDSSGNHLRVFGGGTKLTVL | 12 |
| 3076 | QVNLRESGGGLVQPGGFLRLSCAAFGFTFSGYWMSW VHPAPGKGLEWVANIKQDGSEKFYVDSVKGRFTISR DNAKNSLFLQMNSLRAEDTAVYFCARGLLSDYWGQG TLVPVSSGGGGSGGGGSGGGGSNFMLTQPPSVSVAP GKTASLTCGGYNIGTKSVHWYQQKPGQAPVVVVHDD SDRPSGIPERFSGSNSGTTATLTIIRVEAGDEADYY CQAWDSISEEVVFGGGTKLTVL | :13 |
| 3051 | QVQLQESGGGLVKPGGPLRLSCAASGFTFSSYGMYW VRQAPGKGLEWVSTLSRSGSGTYYAESVKGRFTISR DNSKNTLYFQMNSLRAEDTAVYYCASIAVAGNYFEY WGQGTLVTVSSGGGGSGGGGSGGGGSSYVLTQDPAV SVALGQTVRITCQGDSLRSYYASWYQERPGQAPLLV IYGKNNRPSGIPDRFSGSNSGSTATLTISRVEAGDE GDYYCQVWDSINEQVVFGGGTKVTVL | 14 |
| M49R | QVQLQESGGGLVKPGESLRLSCAASGFTFSDHYMDW VRQAPGKGLEWVAYIRYDGSTKYYADSVKGRFTISR DNSKNTLYLQMNSLRPEDTAFYYCARLIAEAEGWFD PWGQGTLVTVSSGGGGSGGGGSGGGGSNFMLTQPPS VSVAPGKTARITCGGNNIGSKSVYWYQQKPGQAPVL VVYDDSDRPSGIPERFSGSNSGNTATLTISRVEAGD EADYYCQVWDSSSDHVVFGGGTKVTVL | 15 |
| RCI-14 | QVQLLQSAGGLVQPGGSLRLSCAASGFTFSTYAMNW VRQAPGKGLEWVSGISGSGGSTNYADSVKGRFTISR DSSKNTLFLQMNSLRAEDTAVYYCAKDYGSGWYDYW GQGTLVTVSSGGGGSGGGGSGGGGSSSELTQDPAVS VALGQTVRITCQGDSLRSYYASWYQERPGQAPLLVI YGRNERPSGIPDRFSASSSGNTASLTITGAQAEDEA DYYCQVWDSFNEQVVFGGGTKLTVL | 16 |
| II79_4 | QVQLVESGGGLVQPGGSLRLSCAASGFTFSSYAMSW VHQAPGKGLEWVSAISGSGGSTYYADSVKGRFTISR DNSKNTLYLQMNSLRAEDTAVYYCAKTYYGFWSGYY DYLGQGTLVTVSSGGGGSGGGGSGGGGSSSELTQDP AVSVGLGQTVTITCQGDSLRSYYANWYQQKPGQAPI LVIYGENNRPSGIPDRFSGSSSGNTASLTITGAQAE DEADYYCHSRDSSGTHLRVFGGGTKLTVL | 17 |

TABLE 3-continued

Illustrative scFv antibodies. The VL and VH regions are joined by a (Gly4Ser)3 (SEQ ID NO: 1) linker (shown underlined).

| Clone | Amino Acid Sequence | SEQ ID No |
|---|---|---|
| II79_3 | QVQLLESGGGVVQPGTSLRLSCAASGFTFSNYAINW VRQAAGKGLEWVSGISGSGVSTSYADSVKGRFTVSR DNSKNTLYLQMNSLRVEDTALYYCAKNGGGPEYLQH WGQGTLVTVSS<u>GGGGSGGGGSGGGGS</u>QSVLTQPPSA SGTPGQRVTISCSGSSSNIGNNTVNWSRQLPGTAPK LLIYSNDQRPSGVPDRFSGSKSGTSASLAITGLQPE DEADYYCGTWDSSLSAYVFGTGTKLTVL | 18 |
| T5II-4B.1 | QVQLQESGGTLVQPGGSLRLSCAASGFTFSSYAMSW VRQAPGRGLEWVSTISGSGGSTYYADSVKGRFTISR DNSKNTLYLQMNSLRAEDTAVYYCAKGAYSGSYWGQ GTLVTVSS<u>GGGGSGGGGSGGGGS</u>SSELTQDPAVSVA LGQTVRITCQGDSLRSYYASWYQQKPGQAPSLVIYG ENSRPSGIPDRFSGSSSGNTASLTITGAQAENEADY YCQAWDSSTAVVFGGGTKLTVL | 19 |
| T5II-4B.2 | QVQLQESGGTLVQPGGSLRLSCAASGFTFSSYAMSW VRQAPGRGLEWVSTISGSGGSTYYADSVKGRFTISR DNSKNTLYLQMNSLRAEDTAVYYCAKGAYSGSHWGQ GTLVTVSS<u>GGGGSGGGGSGGGGS</u>SSELTQDPAVSVA LGQTVRITCQGDSLRSYYASWYQQKPGQAPSLVIYG ENSRPSGIPDRFSGSSSGNTASLTITGAQAENEADY YCQAWDSSTAVVFGGGTKLTVL | 20 |
| RCI-11 | QVQLVESGAEVKKPGASVKVSCKASGYTFTSYGISW VRQAPGQGLEWMGWISAYNGNTNYAQKLQGRVTMTT DTSTSTAYMELRSLRSDDTAVYYCARPIYDSSGYDA FDIWGQGTMVTVSS<u>GGGGSGGGGSGGGGS</u>DIVMTQS PSTLSASIGDRVTITCRASEGIYHWLAWYQQKPGKA PKLLIYKASSLASGAPSRFSGSGSGTDFTLTISSLQ PDDFATYYCQQYHTISRTFGPGTKVDIK | 21 |
| RCI-20 | QVQLVESGGGLVKPGGSLRLSCAASGFTFSSYAMHW VRQAPGKGLEWVAVISYDGSNKYYADSVKGRFTISR DNSKNTLYLQMNSLRAEDTAVYFCVRPSDSGWSFEH WGQGTLVPVSS<u>GGGGSGGGGSGGGGS</u>QSVLTQPPSA SGTPGQRVTISCSGSSSNIGNNTVNWSRQLPGTAPK LLIYSNDQRPSGVPDRFSGSKSGTSASLAITGLQPE DEADYYCGTWDSSLSAYVFGTGTKLTVL | 22 |
| CI-11A | <u>QVQLQESGGGLVQPGGSLRLSCAASGFTFSSYAMSW VRQAPGKGLEWVAVISYDGSNKYYADSVKGRFTISR DNSKNTLYLQMNSLRAEDTAVYYCVRGDRSYGAEYF QHWGQGTLVTVSSGGGGSGGGGSGGGGS</u>SSELTQDP AVSVASGQTVRITCQGDSLRSYYASWYQQKPGQAPL LVIYGKNIRPSGIPDRFSGSTSGNSASLTITGAQAE DEADYYCNSRDSSGNRNWVFGGGTKLTVL | 23 |
| CI-14A | <u>QVQLQESGGGLVKPGGSLRLSCAASGFTSSSYAMHW VRQAPGKGLEYVSAIGGNGGTYYADSVKGRFTISRD NSKNTLYLQMNSLRAEDTAVYYCAKEGEQWLEYRYY YGMDVWGQGTTVTVSSGGGGSGGGGSGGGGS</u>SSELT QDPAVSVALGQTVRITCQGDSLRSYYASWYQQKPGQ APSLVIYGENSRPSGIPDRFSGSSSGNTASLTITGA QAENEADYYCQAWDSSTAVVFGGGTKLTVL | 24 |
| S95-2 | QVQLVESGGGVVQPGRSLRLSCTASGFTFSSYGMHW VRQAPGKGLEWVAVISYDGSNKYYADSVKGRFTISR DNSKNTLYLQMNSLRAEDTAVYYCARGGRYSSNWFS YYYYGMDVWGQGTTVTVSS<u>GGGGSGGGGSGGGGS</u>NF MLTQPPSVSVAPGKTARITCGGNNIGSKSVYWYQQK PGQAPVLVVYDDSDRPSGIPERFSGSNSGNTATLTI SRVEAGDEADYYCQVWDSSSDHVVFGGGTKVTVL | 25 |

A) Chemical Synthesis.

Using the sequence information provided herein, the prostate cancer specific antibodies of this invention (e.g., 3051.1, G12FC3, M6c42b, 4F3YW, M40pr146, UA20, UA8, 585II41, 585II41.1, 585II56, 3076, 3051, M49R, RCI-14, II79_4, II79_3, T5II-4B.1, T5II-4B.2, RCI-11, RCI-20, CI-11A, CI-14A, S95-2, etc.), or variants thereof, can be chemically synthesized using well known methods of peptide synthesis. Solid phase synthesis in which the C-terminal amino acid of the sequence is attached to an insoluble support followed by sequential addition of the remaining amino acids in the sequence is one preferred method for the chemical synthesis of single chain antibodies. Techniques for solid phase synthesis are described by Barany and Merrifield, *Solid Phase Peptide Synthesis*; pp. 3-284 in *The Peptides: Analysis, Synthesis, Biology*. Vol. 2: *Special Methods in Peptide Synthesis*, Part A., Merrifield et al. (1963) *J. Am. Chem. Soc.,* 85: 2149-2156, and Stewart et al. (1984) *Solid Phase Peptide Synthesis*, 2nd ed. Pierce Chem. Co., Rockford, Ill.

B) Recombinant Expression of Prostate Cancer-Specific Antibodies.

In certain preferred embodiments, the prostate cancer specific antibodies of this invention (e.g., 3051.1, G12FC3, M6c42b, 4F3YW, M40pr146, UA20, UA8, 585II41, 585II41.1, 585II56, 3076, 3051, M49R, RCI-14, II79_4, II79_3, T5II-4B.1, T5II-4B.2, RCI-11, RCI-20, CI-11A, CI-14A, S95-2, etc.), or variants thereof, are prepared using standard techniques well known to those of skill in the art. Using the sequence information provided herein, nucleic acids encoding the desired antibody can be chemically synthesized according to a number of standard methods known to those of skill in the art. Oligonucleotide synthesis, is preferably carried out on commercially available solid phase oligonucleotide synthesis machines (Needham-VanDevanter et al. (1984) *Nucleic Acids Res.* 12: 6159-6168) or manually synthesized using the solid phase phosphoramidite triester method described by Beaucage et. al. (Beaucage et. al. (1981) *Tetrahedron Letts.* 22(20): 1859-1862). Alternatively, nucleic acids encoding the antibody can be amplified and/or cloned according to standard methods.

Molecular cloning techniques to achieve these ends are known in the art. A wide variety of cloning and in vitro amplification methods are suitable for the construction of recombinant nucleic acids. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Methods of producing recombinant immunoglobulins are also known in the art. See, Cabilly, U.S. Pat. No. 4,816,567; and Queen et al. (1989) *Proc. Natl. Acad. Sci. USA* 86: 10029-10033. In addition, detailed protocols for the expression of antibodies are also provided by Liu et al. (2004) *Cancer Res.* 64: 704-710, Poul et al. (2000) *J. Mol. Biol.* 301: 1149-1161, and the like.

C) Identification of Other Antibodies Binding the Same Epitope(s) as Antibodies 3051.1, G12FC3, M6c42b, 4F3YW, M40pr146, UA20, UA8, 585II41, 585II41.1, 585II56, 3076, 3051, M49R, RCI-14, II79_4, II79_3, T5II-4B.1, T5II-4B.2, RCI-11, RCI-20, CI-11A, CI-14A, and/or S95-2.

Having identified useful prostate cancer specific internalizing antibodies (e.g., 3051.1, G12FC3, M6c42b, 4F3YW, M40pr146, UA20, UA8, 585II41, 585II41.1, 585II56, 3076, 3051, M49R, RCI-14, II79_4, II79_3, T5II-4B.1, T5II-4B.2, RCI-11, RCI-20, CI-11A, CI-14A, S95-2), other "related" internalizing prostate cancer specific antibodies can be identified by screening for antibodies that cross-react with the identified antibodies, either at the epitope bound by the antibodies, and/or for antibodies that cross-react with the identified antibodies for binding to a prostate cancer cell (e.g., CaP cells, PC3 cells, etc.), and/or with an idiotypic antibody raised against 3051.1, G12FC3, M6c42b, 4F3YW, M40pr146, UA20, UA8, 585II41, 585II41.1, 585II56, 3076, 3051, M49R, RCI-14, II79_4, II79_3, T5II-4B.1, T5II-4B.2, RCI-11, RCI-20, CI-11A, CI-14A, and/or S95-2 antibodies of this invention.

1) Cross-Reactivity with Anti-Idiotypic Antibodies.

The idiotype represents the highly variable antigen-binding site of an antibody and is itself immunogenic. During the generation of an antibody-mediated immune response, an individual will develop antibodies to the antigen as well as anti-idiotype antibodies, whose immunogenic binding site (idiotype) mimics the antigen.

Anti-idiotypic antibodies can be raised against the variable regions of the antibodies identified herein using standard methods well known to those of skill in the art. Briefly, anti-idiotype antibodies can be made by injecting the antibodies of this invention, or fragments thereof (e.g., CDRs) into an animal thereby eliciting antisera against various antigenic determinants on the antibody, including determinants in the idiotypic region.

Methods for the production of anti-analyte antibodies are well known in the art. Large molecular weight antigens (greater than approx. 5000 Daltons) can be injected directly into animals, whereas small molecular weight compounds (less than approx. 5000 Daltons) are preferably coupled to a high molecular weight immunogenic carrier, usually a protein, to render them immunogenic. The antibodies produced in response to immunization can be utilized as serum, ascites fluid, an immunoglobulin (Ig) fraction, an IgG fraction, or as affinity-purified monospecific material.

Polyclonal anti-idiotype antibodies can be prepared by immunizing an animal with the antibodies of this invention prepared as described above. In general, it is desirable to immunize an animal which is species and allotype-matched with the animal from which the antibody (e.g. phage-display library) was derived. This minimizes the production of antibodies directed against non-idiotypic determinants. The antiserum so obtained is then usually absorbed extensively against normal serum from the same species from which the phage-display library was derived, thereby eliminating antibodies directed against non-idiotypic determinants. Absorption can be accomplished by passing antiserum over a gel formed by crosslinking normal (nonimmune) serum proteins with glutaraldehyde. Antibodies with anti-idiotypic specificity will pass directly through the gel, while those having specificity for non-idiotypic determinants will bind to the gel. Immobilizing nonimmune serum proteins on an insoluble polysaccharide support (e.g., sepharose) also provides a suitable matrix for absorption.

Monoclonal anti-idiotype antibodies can be produced using the method of Kohler et al. (1975) *Nature* 256: 495. In particular, monoclonal anti-idiotype antibodies can be prepared using hybridoma technology which comprises fusing (1) spleen cells from a mouse immunized with the antigen or hapten-carrier conjugate of interest (i.e., the antibodies or this invention or subsequences thereof) to (2) a mouse myeloma cell line which has been selected for resistance to a drug (e.g., 8-azaguanine). In general, it is desirable to use a myeloma cell line which does not secrete an immunoglobulin. Several such lines are known in the art. One generally preferred cell line is P3X63Ag8.653. This cell line is on deposit at the American Type Culture Collection as CRL-1580.

Fusion can be carried out in the presence of polyethylene glycol according to established methods (see, e.g., *Monoclonal Antibodies*, R. Kennett, J. McKearn & K. Bechtol, eds. N.Y., Plenum Press, 1980, and *Current Topics in Microbiology & Immunology*, Vol. 81, F. Melchers, M. Potter & N. L. Warner, eds., N.Y., Springer-Verlag, 1978). The resultant mixture of fused and unfused cells is plated out in hypoxanthine-aminopterin-thymidine (HAT) selective medium. Under these conditions, only hybrid cells will grow.

When sufficient cell growth has occurred, (typically 10-14 days post-fusion), the culture medium is harvested and screened for the presence of monoclonal idiotypic, anti-analyte antibody by any one of a number of methods which include solid phase RIA and enzyme-linked immunosorbent assay. Cells from culture wells containing antibody of the desired specificity are then expanded and recloned. Cells from those cultures that remain positive for the antibody of interest are then usually passed as ascites tumors in susceptible, histocompatible, pristane-primed mice.

Ascites fluid is harvested by tapping the peritoneal cavity, retested for antibody, and purified as described above. If a nonsecreting myeloma line is used in the fusion, affinity purification of the monoclonal antibody is not usually necessary since the antibody is already homogeneous with respect to its antigen-binding characteristics. All that is necessary is to isolate it from contaminating proteins in ascites, i.e., to produce an immunoglobulin fraction.

Alternatively, the hybrid cell lines of interest can be grown in serum-free tissue culture and the antibody harvested from the culture medium. In general, this is a less desirable method of obtaining large quantities of antibody because the yield is low. It is also possible to pass the cells intravenously in mice and to harvest the antibody from serum. This method is generally not preferred because of the small quantity of serum which can be obtained per bleed and because of the need for extensive purification from other serum components. However, some hybridomas will not grow as ascites tumors and therefore one of these alternative methods of obtaining antibody must be used.

2) Cross-Reactivity with the 3051.1, G12FC3, M6c42b, 4F3YW, M40pr146, UA20, UA8, 585II41, 585II41.1, 585II56, 3076, 3051, M49R, RCI-14, II79_4, II79_3, T5II-4B.1, T5II-4B.2, RCI-11, RCI-20, CI-11A, CI-14A, and/or S95-2 Antibodies of this Invention.

In another approach, other prostate cancer specific antibodies of this invention can be identified by the fact that they bind the same epitope as the "prototypic" antibodies of this invention (e.g 3051.1, G12FC3, M6c42b, 4F3YW, M40pr146, UA20, UA8, 585II41, 585II41.1, 585II56, 3076, 3051, M49R, RCI-14, II79_4, II79_3, T5II-4B.1, T5II-4B.2, RCI-11, RCI-20, CI-11A, CI-14A, S95-2, etc.). To identify such antibodies, its not necessary to isolate the subject epitope. In certain embodiments, one can screen, e.g. antibody libraries for antibodies that compete with the prototypic antibodies of this invention for binding and/or internalization by a prostate cancer cell (e.g. a CaP cell, a PC3 cell, etc.).

Methods of screening libraries for cell binding and/or internalization are described in detail in the examples. Such screening methods, done, for example in the presence of labeled prototypic antibodies of this invention allows rapid identification of library members that compete with and exclude the prototypic antibodies of this invention from binding and/or internalization into the target prostate cancer cell.

In addition, it is noted that methods of determining antibody cross-reactivity are well known to those of skill in the art. Generally the epitope bound by the prototypic antibodies of this invention is determined e.g. by epitope mapping techniques. Methods of epitope mapping are well known to those of skill in the art (see, e.g., Reyes et al. (1992) *Hepatitis E Virus (HEV): Epitope Mapping and Detection of Strain Variation*, Elsevier Science Publisher Shikata et al. eds., Chapter 43:237-245; Li et al. (1993) *Nature* 363: 85-88). Epitope mapping can be performed using Novatope system, a kit for which is commercially available from Novagen, Inc.

In certain embodiments, cross-reactive prostate cancer specific antibodies show at least 60%, preferably 80%, more preferably 90%, and most preferably at least 95% or at least 99% cross-reactivity with one or more of the prototypic antibodies of this invention.

D) Phage Display Methods to Select Other "Related" Prostate Cancer Specific Antibodies.

1) Chain Shuffling Methods.

One approach to creating modified single-chain antibody (scFv) gene repertoires has been to replace the original $V_H$ or $V_L$ gene with a repertoire of V-genes to create new partners (chain shuffling) (Clackson et al. (1991) *Nature.* 352: 624-628). Using chain shuffling and phage display, the affinity of a human scFv antibody fragment that bound the hapten phenyloxazolone (phOx) was increased from 300 nM to 1 nM (300 fold) (Marks et al. (1992) *Bio/Technology* 10: 779-783).

Thus, for example, to alter the affinity of a prostate cancer specific antibodies, a mutant scFv gene repertoire can be created containing a $V_H$ gene of the prototypic antibodies (e.g. as shown in Tables 1-3, and/or FIGS. 7 and 8) antibody and a human $V_L$ gene repertoire (light chain shuffling). The scFv gene repertoire can be cloned into a phage display vector, e.g., pHEN-1 (Hoogenboom et al. (1991) *Nucleic Acids Res.,* 19: 4133-4137) or other vectors, e.g. as described herein in the examples, and after transformation a library of transformants is obtained.

Similarly, for heavy chain shuffling, the prostate cancer specific antibody (e.g., 3051.1, G12FC3, M6c42b, 4F3YW, M40pr146, UA20, UA8, 585II41, 585II41.1, 585II56, 3076, 3051, M49R, RCI-14, II79_4, II79_3, T5II-4B.1, T5II-4B.2, RCI-11, RCI-20, CI-11A, CI-14A, S95-2, etc.) $V_H$ CDR1 and/or CDR2, and/or CDR3 and light chain (see, e.g., Table 2) are cloned into a vector containing a human $V_H$ gene repertoire to create a phage antibody library transformants. For detailed descriptions of chain shuffling to increase antibody affinity see Schier et al. (1996) *J. Mol. Biol.,* 255: 28-43, and the like.

2) Site-Directed Mutagenesis to Improve Binding Affinity.

The majority of antigen contacting amino acid side chains are typically located in the complementarity determining regions (CDRs), three in the $V_H$ (CDR1, CDR2, and CDR3) and three in the $V_L$ (CDR1, CDR2, and CDR3) (Chothia et al. (1987) *J. Mol. Biol.,* 196: 901-917; Chothia et al. (1986) *Science,* 233: 755-8; Nhan et al. (1991) *J. Mol. Biol.,* 217: 133-151). These residues contribute the majority of binding energetics responsible for antibody affinity for antigen. In other molecules, mutating amino acids which contact ligand has been shown to be an effective means of increasing the affinity of one protein molecule for its binding partner (Lowman et al. (1993) *J. Mol. Biol.,* 234: 564-578; Wells (1990) *Biochemistry,* 29: 8509-8516). Site-directed mutagenesis of CDRs and screening against the prostate cancer cells, e.g. as described herein in the examples, can produce antibodies having improved binding affinity.

3) CDR Randomization to Produce Higher Affinity Human scFv.

In an extension of simple site-directed mutagenesis, mutant antibody libraries can be created where partial or entire CDRs are randomized ($V_L$ CDR1CDR2 and/or CDR3 and/or $V_H$ CDR1, CDR2 and/or CDR3). In one embodiment, each CDR is randomized in a separate library, using a known antibody (e.g., 3051.1, G12FC3, M6c42b, 4F3YW, M40pr146, UA20, UA8, 585II41, 585II41.1, 585II56, 3076, 3051, M49R, RCI-14, II79_4, II79_3, T5II-4B.1, T5II-4B.2, RCI-11, RCI-20, CI-11A, CI-14A, and/or S95-2) as a template. The CDR sequences of the highest affinity mutants from each CDR library are combined to obtain an additive increase in affinity. A similar approach has been used to increase the affinity of human growth hormone (hGH) for the growth hormone receptor over 1500 fold from $3.4 \times 10^{-10}$ to $9.0 \times 10^{-13}$ M (Lowman et al. (1993) *J. Mol. Biol.,* 234: 564-578).

$V_H$ CDR3 often occupies the center of the binding pocket, and thus mutations in this region are likely to result in an increase in affinity (Clackson et al. (1995) *Science,* 267: 383-386). In one embodiment, four $V_H$ CDR3 residues are randomized at a time using the nucleotides NNS (see, e.g., Schier et al. (1996) *Gene,* 169: 147-155; Schier and Marks (1996) *Human Antibodies and Hybridomas.* 7: 97-105, 1996; and Schier et al. (1996) *J. Mol. Biol.* 263: 551-567).

E) Creation of Other Antibody Forms.

Using the known and/or identified sequences (e.g. $V_H$ and/or $V_L$ sequences) of the single chain antibodies provided herein other antibody forms can readily be created. Such forms include, but are not limited to multivalent antibodies, full antibodies, scFv, (scFv')$_2$, Fab, (Fab')$_2$, chimeric antibodies, and the like.

1) Creation of Homodimers.

For example, to create (scFv')$_2$ antibodies, two prostate cancer specific scFvs are joined, either through a linker (e.g., a carbon linker, a peptide, etc.) or through a disulfide bond between, for example, two cysteines. Thus, for example, to create disulfide linked scFv, a cysteine residue can be introduced by site directed mutagenesis at the carboxy-terminus of the antibodies described herein.

An scFv can be expressed from this construct, purified by IMAC, and analyzed by gel filtration. To produce (scFv')$_2$ dimers, the cysteine is reduced by incubation with 1 mM 3-mercaptoethanol, and half of the scFv blocked by the addition of DTNB. Blocked and unblocked scFvs are incubated together to form (scFv')$_2$ and the resulting material can be analyzed by gel filtration. The affinity of the resulting dimmer can be determined using standard methods, e.g. by BIAcore.

In one particularly preferred embodiment, the (scFv')$_2$ dimer is created by joining the scFv' fragments through a linker, more preferably through a peptide linker. This can be accomplished by a wide variety of means well known to those of skill in the art. For example, one preferred approach is described by Holliger et al. (1993) *Proc. Natl. Acad. Sci. USA,* 90: 6444-6448 (see also WO 94/13804).

It is noted that using the $V_H$ and/or $V_L$ sequences provided herein Fabs and (Fab')$_2$ dimers can also readily be prepared. Fab is a light chain joined to $V_H$—$C_H$1 by a disulfide bond and can readily be created using standard methods known to those of skill in the art. The F(ab)'$_2$ can be produced by dimerizing the Fab, e.g. as described above for the (scFv')$_2$ dimer.

2) Chimeric Antibodies.

The antibodies of this invention also include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; Morrison et al. (1984) *Proc. Natl. Acad. Sci.* 81: 6851-6855, etc.).

While the prototypic antibodies provided herein are fully human antibodies, chimeric antibodies are contemplated, particularly when such antibodies are to be used in species other than humans (e.g., in veterinary applications). Chimeric antibodies are antibodies comprising a portions from two different species (e.g. a human and non-human portion). Typically, the antigen combining region (or variable region) of a chimeric antibody is derived from a one species source and the constant region of the chimeric antibody (which confers biological effector function to the immunoglobulin) is derived from another source. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369, and PCT application WO 91/0996).

In general, the procedures used to produce chimeric antibodies consist of the following steps (the order of some steps may be interchanged): (a) identifying and cloning the correct gene segment encoding the antigen binding portion of the antibody molecule; this gene segment (known as the VDJ, variable, diversity and joining regions for heavy chains or VJ, variable, joining regions for light chains, or simply as the V or variable region or $V_H$ and $V_L$ regions) may be in either the cDNA or genomic form; (b) cloning the gene segments encoding the human constant region or desired part thereof; (c) ligating the variable region to the constant region so that the complete chimeric antibody is encoded in a transcribable and translatable form; (d) ligating this construct into a vector containing a selectable marker and gene control regions such as promoters, enhancers and poly(A) addition signals; (e) amplifying this construct in a host cell (e.g., bacteria); (f) introducing the DNA into eukaryotic cells (transfection) most often mammalian lymphocytes; and culturing the host cell under conditions suitable for expression of the chimeric antibody.

Antibodies of several distinct antigen binding specificities have been manipulated by these protocols to produce chimeric proteins (e.g., anti-TNP: Boulianne et al. (1984) *Nature*, 312: 643; and anti-tumor antigens: Sahagan et al. (1986) *J. Immunol.*, 137: 1066). Likewise several different effector functions have been achieved by linking new sequences to those encoding the antigen binding region. Some of these include enzymes (Neuberger et al. (1984) *Nature* 312: 604), immunoglobulin constant regions from another species and constant regions of another immunoglobulin chain (Sharon et al. (1984) *Nature* 309: 364; Tan et al., (1985) *J. Immunol.* 135: 3565-3567).

In certain embodiments, a recombinant DNA vector is used to transfect a cell line that produces a prostate cancer specific antibody of this invention. The novel recombinant DNA vector contains a "replacement gene" to replace all or a portion of the gene encoding the immunoglobulin constant region in the cell line (e.g., a replacement gene may encode all or a portion of a constant region of a human immunoglobulin, a specific immunoglobulin class, or an enzyme, a toxin, a biologically active peptide, a growth factor, inhibitor, or a linker peptide to facilitate conjugation to a drug, toxin, or other molecule, etc.), and a "target sequence" that allows for targeted homologous recombination with immunoglobulin sequences within the antibody producing cell.

In another embodiment, a recombinant DNA vector is used to transfect a cell line that produces an antibody having a desired effector function, (e.g., a constant region of a human immunoglobulin) in which case, the replacement gene contained in the recombinant vector may encode all or a portion of a region of a prostate cancer specific antibody of this invention and the target sequence contained in the recombinant vector allows for homologous recombination and targeted gene modification within the antibody producing cell. In either embodiment, when only a portion of the variable or constant region is replaced, the resulting chimeric antibody can define the same antigen and/or have the same effector function yet be altered or improved so that the chimeric antibody may demonstrate a greater antigen specificity, greater affinity binding constant, increased effector function, or increased secretion and production by the transfected antibody producing cell line, etc.

Regardless of the embodiment practiced, the processes of selection for integrated DNA (via a selectable marker), screening for chimeric antibody production, and cell cloning, can be used to obtain a clone of cells producing the chimeric antibody.

Thus, a piece of DNA that encodes a modification for a monoclonal antibody can be targeted directly to the site of the expressed immunoglobulin gene within a B-cell or hybridoma cell line. DNA constructs for any particular modification can be made to alter the protein product of any monoclonal cell line or hybridoma. The level of expression of chimeric antibody should be higher when the gene is at its natural chromosomal location rather than at a random position. Detailed methods for preparation of chimeric (humanized) antibodies can be found in U.S. Pat. No. 5,482,856.

3) Intact Human Antibodies.

In another embodiment, this invention provides for intact, fully human prostate cancer specific antibodies. Such antibodies can readily be produced in a manner analogous to making chimeric human antibodies. In this instance, instead of using a recognition function derived, e.g. from a murine, the fully human recognition function (e.g., VH and $V_L$) of the antibodies described herein is utilized.

4) Diabodies.

In certain embodiments, this invention contemplates diabodies comprising one or more of the $V_H$ and $V_L$ domains described herein. The term "diabodies" refers to antibody fragments typically having two antigen-binding sites. The fragments typically comprise a heavy chain variable domain ($V_H$) connected to a light chain variable domain ($V_L$) in the same polypeptide chain ($V_H$—$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Holliger et al. (1993) *Proc. Natl. Acad. Sci. USA* 90: 6444-6448.

5) Unibodies.

In certain embodiments using the sequence information provided herein, the antibodies of this invention can be constructed as unibodies. UniBody are antibody technology that produces a stable, smaller antibody format with an anticipated longer therapeutic window than certain small antibody formats. In certain embodiments unibodies are produced from IgG4 antibodies by eliminating the hinge region of the antibody. Unlike the full size IgG4 antibody, the half molecule fragment is very stable and is termed a uniBody. Halving the IgG4 molecule leaves only one area on the UniBody that can bind to a target. Methods of producing unibodies are described in detail in PCT Publication WO2007/059782, which is incorporated herein by reference in its entirety (see, also, Kolfschoten et al. (2007) *Science* 317: 1554-1557).

6) Affibodies.

In certain embodiments the sequence information provided herein is used to construct affibody molecules that bind prostate cancer cells. Affibody molecules are class of affinity proteins based on a 58-amino acid residue protein domain, derived from one of the IgG-binding domains of staphylococcal protein A. This three helix bundle domain has been used as a scaffold for the construction of combinatorial phagemid libraries, from which affibody variants that target the desired molecules can be selected using phage display technology (see, e.g., Nord et al. (1997) *Nat. Biotechnol.* 15: 772-777; Ronmark et al. (2002) *Eur. J. Biochem.,* 269: 2647-2655). Details of Affibodies and methods of production are known to those of skill (see, e.g., U.S. Pat. No. 5,831,012 which is incorporated herein by reference in its entirety).

It will be recognized that the antibodies described above can be provided as whole intact antibodies (e.g., IgG), antibody fragments, or single chain antibodies, using methods well known to those of skill in the art. In addition, while the antibody can be from essentially any mammalian species, to reduce immunogenicity, it is desirable to use an antibody that is of the species in which the antibody and/or chimeric moiety is to be used. In other words, for use in a human, it is desirable to use a human, humanized, or chimeric human antibody.

7) Measurement of Antibody/Polypeptide Binding Affinity.

As explained above, selection for increased avidity can involves measuring the affinity of the antibody for the target antigen (e.g., a prostate cancer cell). Methods of making such measurements are well known to those of skill in the art. Briefly, for example, the $K_d$ of the antibody is determined from the kinetics of binding to, e.g. the target cell in a BIAcore, a biosensor based on surface plasmon resonance. For this technique, the antigen or cell is coupled to a derivatized sensor chip capable of detecting changes in mass. When antibody is passed over the sensor chip, antibody binds to the antigen resulting in an increase in mass that is quantifiable. Measurement of the rate of association as a function of antibody concentration can be used to calculate the association rate constant ($k_{on}$). After the association phase, buffer is passed over the chip and the rate of dissociation of antibody ($k_{off}$) determined. $K_{on}$ is typically measured in the range $1.0 \times 10^2$ to $5.0 \times 10^6$ and $k_{off}$ in the range $1.0 \times 10^{-1}$ to $1.0 \times 10^{-6}$. The equilibrium constant $K_d$ is often calculated as $k_{off}/k_{on}$ and thus is typically measured in the range $10^{-5}$ to $10^{-12}$. Affinities measured in this manner correlate well with affinities measured in solution by fluorescence quench titration.

III. Chimeric Moieties Comprising Anti-Prostate Cancer Antibodies.

The prototypical prostate cancer-specific antibodies of this invention (e.g., 3051.1, G12FC3, M6c42b, 4F3YW, M40pr146, UA20, UA8, 58SII41, 58SII41.1, 58SII56, 3076, 3051, M49R, RCI-14, II79_4, II79_3, T5II-4B.1, T5II-4B.2, RCI-11, RCI-20, CI-11A, CI-14A, S95-2, etc.) specifically bind to and are internalized by prostate cancer cells. The antibodies can be used alone as therapeutics (e.g. to inhibit growth and/or proliferation of a prostate cancer cell) or they can be coupled to an effector to provide efficient and specific delivery of the effector (e.g. an effector molecule such as a cytotoxin, a radiolabel, a cancer drug, etc.) to various prostate cancer cells (e.g. isolated cells, metastatic cells, solid tumor cells, etc.).

In certain preferred embodiments, the antibodies of this invention are utilized in a "pretargeting" strategy (resulting in formation of a chimeric moiety at the target site after administration of the effector moiety) or in a "targeting" strategy where the antibody is coupled to an effector molecule prior to use to provide a chimeric molecule.

A chimeric molecule or chimeric composition or chimeric moiety refers to a molecule or composition wherein two or more molecules that exist separately in their native state are joined together to form a single molecule having the desired functionality of its constituent molecules. Typically, one of the constituent molecules of a chimeric molecule is a "targeting molecule. The targeting molecule is a molecule such as a ligand or an antibody that specifically binds (and, in certain embodiments, is internalized) by its corresponding target, e.g., a prostate cancer cell.

Another constituent of the chimeric moiety is an "effector". The effector refers to a molecule or group of molecules that is to be specifically/preferentially transported toor into the target cell (e.g., a prostate cancer cell). It is noted that in this context, such specific transport need not be exclusively to or into a cancer cell, but merely need to provide preferential delivery of the effector to or into the cancer cell as compared to normal healthy cells.

The effector molecule typically has a characteristic activity that is to be delivered to or into the target cell. Effector molecules include, but are not limited to cytotoxins, labels, radionuclides, ligands, antibodies, drugs, liposomes, nanoparticles, viral particles, cytokines, and the like.

In certain embodiments, the effector comprises a detectable label. Suitable detectable labels include, but are not limited to radio-opaque labels, nanoparticles, PET labels, MRI labels, radioactive labels, and the like. Among the radionuclides and useful in various embodiments of the present invention, gamma-emitters, positron-emitters, x-ray emitters and fluorescence-emitters are suitable for localization, diagnosis and/or staging, and/or therapy, while beta and alpha-emitters and electron and neutron-capturing agents, such as boron and uranium, also can be used for therapy.

The detectable labels can be used in conjunction with an external detector and/or an internal detector and provide a means of effectively localizing and/or visualizing prostate cancer cells. Such detection/visualization can be useful in various contexts including, but not limited to pre-operative and intraoperative settings. Thus, in certain embodiment this invention relates to a method of intraoperatively detecting and prostate cancers in the body of a mammal. These methods typically involve administering to the mammal a composition comprising, in a quantity sufficient for detection by a detector (e.g. a gamma detecting probe), an prostate cancer specific antibody labeled with a detectable label (e.g. antibodies of this invention labeled with a radioisotope, e.g. $^{161}$Tb, $^{123}$I, $^{125}$I, and the like), and, after allowing the active substance to be taken up by the target tissue, and preferably after blood clearance of the label, subjecting the mammal to a radioimmunodetection technique in the relevant area of the body, e.g. by using a gamma detecting probe.

In certain embodiments the label-bound antibody can be used in the technique of radioguided surgery, wherein relevant tissues in the body of a subject can be detected and located intraoperatively by means of a detector, e.g. a gamma detecting probe. The surgeon can, intraoperatively, use this probe to find the tissues in which uptake of the compound labeled with a radioisotope, that is, e.g. a low-energy gamma photon emitter, has taken place. In certain embodiments such methods are particularly useful in localizing and removing secondary cancers produced by metastatic cells from a primary tumor.

In addition to detectable labels, certain preferred effectors include, but are not limited to cytotoxins (e.g. *Pseudomonas* exotoxin, ricin, abrin, Diphtheria toxin, and the like), or cytotoxic drugs or prodrugs, in which case the chimeric molecule may act as a potent cell-killing agent specifically targeting the cytotoxin to prostate cancer cells.

In still other embodiments, the effector can include a liposome encapsulating a drug (e.g. an anti-cancer drug such as abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, zoledronic acid, vinblastine, etc.), an antigen that stimulates recognition of the bound cell by components of the immune system, an antibody that specifically binds immune system components and directs them to the prostate cancer, and the like.

A) Illustrative Effectors.

1) Imaging Compositions.

In certain embodiments, the chimeric moieties of this invention can be used to direct detectable labels to a tumor site. This can facilitate tumor detection and/or localization. It can be effective for detecting primary tumors, or, in certain embodiments, secondary tumors produced by, e.g., prostate metastatic cells. In certain embodiments, the effector component of the chimeric moiety comprises a "radio-opaque" label, e.g. a label that can be easily visualized using x-rays. Radio-opaque materials are well known to those of skill in the art. The most common radio-opaque materials include iodide, bromide or barium salts. Other radiopaque materials are also known and include, but are not limited to, organic bismuth derivatives (see, e.g., U.S. Pat. No. 5,939,045), radio-opaque polyurethanes (see, e.g., U.S. Pat. No. 5,346,981), organobismuth composites (see, e.g., U.S. Pat. No. 5,256,334), radio-opaque barium polymer complexes (see, e.g., U.S. Pat. No. 4,866,132), and the like.

The antibodies of this invention can be coupled directly to the radio-opaque moiety or they can be attached to a "package" (e.g., a chelate, a liposome, a polymer microbead, a nanoparticle, etc.) carrying, containing, or comprising the radio-opaque material, e.g., as described below.

In addition to radio-opaque labels, other labels are also suitable for use in this invention. Detectable labels suitable for use as the effector molecule component of the chimeric moietys of this invention include any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, texas red, rhodamine, green fluorescent protein, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads, nanoparticles, quantum dots, and the like.

In certain embodiments, suitable radiolabels include, but are not limited to, $^{99}Tc$, $^{203}Pb$, $^{67}Ga$, $^{68}Ga$, $^{72}As$, $^{111}In$, $^{113m}In$, $^{97}Ru$, $^{62}Cu$, $^{64}1Cu$, $^{52}Fe$, $^{52m}Mn$, $^{51}Cr$, $^{186}Re$, $^{188}Re$, $^{77}As$, $^{90}Y$, $^{67}Cu$, $^{169}Er$, $^{121}Sn$, $^{127}Te$, $^{142}Pr$, $^{143}Pr$, $^{198}Au$, $^{199}Au$, $^{161}Tb$, $^{109}Pd$, $^{165}Dy$, $^{149}Pm$, $^{151}Pm$, $^{153}Sm$, $^{157}Gd$, $^{159}Gd$, $^{166}Ho$, $^{172}Tm$, $^{169}Yb$, $^{175}Yb$, $^{177}Lu$, $^{105}Rh$, and $^{111}Ag$.

Means of detecting such labels are well known to those of skill in the art. Thus, for example, certain radiolabels may be detected using photographic film, scintillation detectors, PET imaging, MRI, and the like. Fluorescent markers can be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

2) Radiosensitizers.

In another embodiment, the effector can comprise a radiosensitizer that enhances the cytotoxic effect of ionizing radiation (e.g., such as might be produced by $^{60}Co$ or an x-ray source) on a cell. Numerous radiosensitizing agents are known and include, but are not limited to benzoporphyrin derivative compounds (see, e.g., U.S. Pat. No. 5,945,439), 1,2,4-benzotriazine oxides (see, e.g., U.S. Pat. No. 5,849, 738), compounds containing certain diamines (see, e.g., U.S. Pat. No. 5,700,825), BCNT (see, e.g., U.S. Pat. No. 5,872, 107), radiosensitizing nitrobenzoic acid amide derivatives (see, e.g., U.S. Pat. No. 4,474,814), various heterocyclic derivatives (see, e.g., U.S. Pat. No. 5,064,849), platinum complexes (see, e.g., U.S. Pat. No. 4,921,963), and the like.

3) Alpha Emitters.

In certain embodiments, the effector can include an alpha emitter, i.e. a radioactive isotope that emits alpha particles. Alpha-emitters have recently been shown to be effective in the treatment of cancer (see, e.g., McDevitt et al. (2001) Science 294:1537-1540; Ballangrud et al. (2001) Cancer Res. 61: 2008-2014; Borchardt et al. (2003) Cancer Res. 63: 5084-50). Suitable alpha emitters include, but are not limited to Bi, $^{213}Bi$, $^{211}At$, and the like.

4) Ligands.

The effector molecule can also comprise a ligand, an epitope tag, or an antibody. In certain embodiments preferred ligands and antibodies include those that bind to surface markers on immune cells. Chimeric moietys utilizing such antibodies as effector molecules act as bifunctional linkers establishing an association between the immune cells bearing binding partner for the ligand or antibody and the prostate cancer cell(s).

5) Chelates

Many of the pharmaceuticals and/or radiolabels described herein can be provided as a chelate, particularly where a pre-targeting strategy is utilized. The chelating molecule is typically coupled to a molecule (e.g. biotin, avidin, streptavidin, etc.) that specifically binds an epitope tag attached to a prostate cancer specific antibody of this invention.

Chelating groups are well known to those of skill in the art. In certain embodiments, chelating groups are derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N'-,N'',N'''-tetra-acetic acid (DOTA), hydroxyethyldiamine triacetic acid (HEDTA), 1,4,8,11-tetraazacyclotetradecane-N,N',N'',N'''-tetra-acetic acid (TETA), substituted DTPA, substituted EDTA, and the like.

Examples of certain preferred chelators include unsubstituted or, substituted 2-iminothiolanes and 2-iminothiacyclohexanes, in particular 2-imino-4-mercaptomethylthiolane.

One chelating agent, 1,4,7,10-tetraazacyclododecane-N, N,N'',N'''-tetraacetic acid (DOTA), is of particular interest because of its ability to chelate a number of diagnostically and therapeutically important metals, such as radionuclides and radiolabels.

Conjugates of DOTA and proteins such as antibodies have been described. For example, U.S. Pat. No. 5,428,156 teaches a method for conjugating DOTA to antibodies and antibody fragments. To make these conjugates, one carboxylic acid group of DOTA is converted to an active ester which can react with an amine or sulfhydryl group on the antibody or antibody fragment. Lewis et al. (1994) *Bioconjugate Chem.* 5: 565-576, describes a similar method wherein one carboxyl group of DOTA is converted to an active ester, and the activated DOTA is mixed with an antibody, linking the antibody to DOTA via the epsilon-amino group of a lysine residue of the antibody, thereby converting one carboxyl group of DOTA to an amide moiety.

In certain embodiments the chelating agent can be coupled, directly or through a linker, to an epitope tag or to a moiety that binds an epitope tag. Conjugates of DOTA and biotin have been described (see, e.g., Su (1995) *J. Nucl. Med.,* 36 (5 Suppl):154P, which discloses the linkage of DOTA to biotin via available amino side chain biotin derivatives such as DOTA-LC-biotin or DOTA-benzyl-4-(6-amino-caproamide)-biotin). Yau et al., WO 95/15335, disclose a method of producing nitro-benzyl-DOTA compounds that can be conjugated to biotin. The method comprises a cyclization reaction via transient projection of a hydroxy group; tosylation of an amine; deprotection of the transiently protected hydroxy group; tosylation of the deprotected hydroxy group; and intramolecular tosylate cyclization. Wu et al. (1992) *Nucl. Med. Biol.,* 19(2): 239-244 discloses a synthesis of macrocyclic chelating agents for radiolabeling proteins with $^{111}$IN and $^{90}$Y. Wu et al. makes a labeled DOTA-biotin conjugate to study the stability and biodistribution of conjugates with avidin, a model protein for studies. This conjugate was made using a biotin hydrazide which contained a free amino group to react with an in situ generated activated DOTA derivative.

6) Cytotoxins.

The antibodies of this invention can be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy α-emitters as described above.

Enzymatically active toxins and fragments, thereof are exemplified by diphtheria toxin A fragment, nonbinding active fragments of diphtheria toxin, exotoxin A (from *Pseudomonas aeruginosa*), ricin A chain, abrin A chain, modeccin A chain, .alpha.-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin, for example.

In certain embodiments the cytotoxins can include, but are not limited to *Pseudomonas* exotoxins, Diphtheria toxins, ricin, abrin and derivatives thereof. *Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2, which inactivates the protein and causes cell death. The function of domain Ib (amino acids 365-399) remains undefined, although a large part of it, amino acids 365-380, can be deleted without loss of cytotoxicity. See Siegall et al. (1989) *J. Biol. Chem.* 264: 14256-14261.

In certain embodiments the antibody is attached to a preferred molecule in which domain Ia (amino acids 1 through 252) is deleted and amino acids 365 to 380 have been deleted from domain Ib. In certain embodiments all of domain Ib and a portion of domain II (amino acids 350 to 394) can be deleted, particularly if the deleted sequences are replaced with a linking peptide.

In addition, the PE and other cytotoxic proteins can be further modified using site-directed mutagenesis or other techniques known in the art, to alter the molecule for a particular desired application. For example, means to alter the PE molecule in a manner that does not substantially affect the functional advantages provided by the PE molecules described here can also be used and such resulting molecules are intended to be covered herein.

Methods of cloning genes encoding PE fused to various ligands are well known to those of skill in the art (see, e.g., Siegall et al. (1989) *FASEB J.,* 3: 2647-2652; and Chaudhary et al. (1987) *Proc. Natl. Acad. Sci. USA,* 84: 4538-4542).

Like PE, diphtheria toxin (DT) kills cells by ADP-ribosylating elongation factor 2 thereby inhibiting protein synthesis. Diphtheria toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al. (1972) *Science,* 175: 901-903; Uchida et al. (1973) *J. Biol. Chem.,* 248: 3838-3844).

In certain embodiments, the antibody-Diphtheria toxin chimeric moietys of this invention have the native receptor-binding domain removed by truncation of the Diphtheria toxin B chain. One illustrative modified Diphtheria toxin is DT388, a DT in which the carboxyl terminal sequence beginning at residue 389 is removed (see, e.g., Chaudhary et al. (1991) *Bioch. Biophys. Res. Comm.,* 180: 545-551). Like the PE chimeric cytotoxins, the DT molecules can be chemically conjugated to the prostate cancer specific antibody, but, in certain preferred embodiments, the antibody will be fused to the Diphtheria toxin by recombinant means (see, e.g., Williams et al. (1990) *J. Biol. Chem.* 265: 11885-11889).

7) Viral Particles.

In certain embodiments, the effector comprises a viral particle (e.g., a filamentous phage, an adeno-associated virus (AAV), a lentivirus, and the like). The antibody can be conjugated to the viral particle and/or can be expressed on the surface of the viral particle (e.g. a filamentous phage). The viral particle can additionally include a nucleic acid that is to be delivered to the target (e.g., prostate cancer) cell. The use of viral particles to deliver nucleic acids to cells is described in detail in WO 99/55720, U.S. Pat. No. 6,670,188, U.S. Pat. No. 6,642,051, and U.S. Pat. No. 6,669,936.

8) Other Therapeutic Moieties.

Other suitable effector molecules include pharmacological agents or encapsulation systems containing various pharmacological agents. Thus, the targeting molecule of the chimeric moiety can be attached directly to a drug that is to be delivered directly to the tumor. Such drugs are well known to those of skill in the art and include, but are not limited to, abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, zoledronic acid, vinblastine, etc.), an antisense molecule, an SiRNA, and the like.

Alternatively, the effector molecule can comprise an encapsulation system, such as a viral capsid, a liposome, or micelle that contains a therapeutic composition such as a drug, a nucleic acid (e.g. an antisense nucleic acid or another nucleic acid to be delivered to the cell), or another therapeutic moiety that is preferably shielded from direct exposure to the circulatory system. Means of preparing liposomes attached to antibodies are well known to those of skill in the art. See, for example, U.S. Pat. No. 4,957,735, Connor et al. (1985) *Pharm. Ther.,* 28: 341-365. In addition coupling of liposomes to antibodies of this invention is illustrated herein in the Examples.

B) Attachment of the Antibody to the Effector.

One of skill will appreciate that the antibodies of this invention and the effector molecule(s) can be joined together in any order. Thus, where antibody is a single chain polypeptide, the effector molecule can be joined to either the amino or carboxy termini of the targeting molecule. The targeting molecule can also be joined to an internal region of the effector molecule, or conversely, the effector molecule can be joined to an internal location of the targeting molecule, as long as the attachment does not interfere with the respective activities of the molecules.

The antibody and the effector can be attached by any of a number of means well known to those of skill in the art. Typically the effector is conjugated, either directly or through a linker (spacer), to the targeting molecule. However, In certain embodiments, where both the effector molecule and the antibody are polypeptides it is preferable to recombinantly express the chimeric molecule as a single-chain fusion protein.

1) Conjugation of the Effector Molecule to the Antibody.

In one embodiment, the prostate cancer specific antibody is chemically conjugated to the effector molecule (e.g., a cytotoxin, a label, a ligand, or a drug or liposome, etc.). Means of chemically conjugating molecules are well known to those of skill.

The procedure for attaching an effector to an antibody will vary according to the chemical structure of the effector and/or antibody. Polypeptides typically contain variety of functional groups; e.g., carboxylic acid (COOH) or free amine ($-NH_2$) groups, that are available for reaction with a suitable functional group on an effector molecule to bind the effector thereto.

Alternatively, the antibody and/or the effector can be derivatized to expose or attach additional reactive functional groups. The derivatization can involve attachment of any of a number of linker molecules such as those available from Pierce Chemical Company, Rockford Ill.

A "linker", as used herein, is a molecule that is used to join the targeting molecule to the effector molecule. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. Where the targeting molecule and the effector molecule are polypeptides, the linkers may be joined to the constituent amino acids through their side groups (e.g., through a disulfide linkage to cysteine). However, in a preferred embodiment, the linkers will be joined to the alpha carbon amino or carboxyl groups of the terminal amino acids.

A bifunctional linker having one functional group reactive with a group on a particular agent, and another group reactive with an antibody, may be used to form the desired immunoconjugate. In certain embodiments, derivatization can involve chemical treatment of the targeting molecule, e.g., glycol cleavage of the sugar moiety of a the glycoprotein antibody with periodate to generate free aldehyde groups. The free aldehyde groups on the antibody may be reacted with free amine or hydrazine groups on an agent to bind the agent thereto. (See U.S. Pat. No. 4,671,958). Procedures for generation of free sulfhydryl groups on polypeptide, such as antibodies or antibody fragments, are also known (See U.S. Pat. No. 4,659,839).

Many procedures and linker molecules for attachment of various compounds including radionuclide metal chelates, toxins and drugs to proteins such as antibodies are known (see, e.g., European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075). In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine,* Academic Press, pp. 168-190 (1982), Waldmann (1991) *Science,* 252: 1657, U.S. Pat. Nos. 4,545,985 and 4,894,443.

In some circumstances, it is desirable to free the effector from the targeting molecule when the chimeric molecule has reached its target site. Therefore, chimeric conjugates comprising linkages which are cleavable in the vicinity of the target site may be used when the effector is to be released at the target site. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

2 Conjugation of Chelates.

In certain preferred embodiments, the effector comprises a chelate that is attached to an antibody or to an epitope tag. The prostate cancer specific antibody bears a corresponding epitope tag or antibody so that simple contacting of the antibody to the chelate results in attachment of the antibody with the effector. The combining step can be performed before the moiety is used (targeting strategy) or the target tissue can be bound to the antibody before the chelate is delivered. Methods of producing chelates suitable for coupling to various targeting moieties are well known to those of skill in the art (see, e.g., U.S. Pat. Nos. 6,190,923, 6,187,285, 6,183,721, 6,177,562, 6,159,445, 6,153,775, 6,149,890, 6,143,276, 6,143,274, 6,139,819, 6,132,764, 6,123,923, 6,123,921, 6,120,768, 6,120,751, 6,117,412, 6,106,866, 6,096,290, 6,093,382, 6,090,800, 6,090,408, 6,088,613, 6,077,499, 6,075,010, 6,071,494, 6,071,490, 6,060,040, 6,056,939, 6,051,207, 6,048,979, 6,045,821, 6,045,775, 6,030,840, 6,028,066, 6,022,966, 6,022,523, 6,022,522, 6,017,522, 6,015,897, 6,010,682, 6,010,681, 6,004,533, and 6,001,329).

3) Production of Fusion Proteins.

Where the antibody and/or the effector is relatively short (i.e., less than about 50 amino acids) they can be synthesized using standard chemical peptide synthesis techniques. Where both molecules are relatively short the chimeric molecule may be synthesized as a single contiguous polypeptide. Alternatively the targeting molecule and the effector molecule may be synthesized separately and then fused by condensation of the amino terminus of one molecule with the carboxyl terminus of the other molecule thereby forming a peptide bond. Alternatively, the targeting and effector molecules can each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis*; pp. 3-284 in *The Peptides: Analysis, Synthesis, Biology. Vol. 2: Special Methods in Peptide Synthesis, Part A.*, Merrifield, et al. *J. Am. Chem. Soc.*, 85: 2149-2156 (1963), and Stewart et al., *Solid Phase Peptide Synthesis,* 2nd ed. Pierce Chem. Co., Rockford, Ill. (1984).

In certain embodiments, the chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins of this invention can be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; and the solid support method of U.S. Pat. No. 4,458,066.

Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences can be obtained by the ligation of shorter sequences.

Alternatively, subsequences can be cloned and the appropriate subsequences cleaved using appropriate restriction enzymes. The fragments can then be ligated to produce the desired DNA sequence.

In certain embodiments DNA encoding fusion proteins of the present invention can be cloned using PCR cloning methods.

While the antibody and the effector are, in certain embodiments, essentially joined directly together, one of skill will appreciate that the molecules can be separated by a spacer, e.g., a peptide spacer consisting of one or more amino acids (e.g., (Gly$_4$Ser)$_3$ (SEQ ID NO:1). Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The nucleic acid sequences encoding the fusion proteins can be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) *Protein Purification*, Springer-Verlag, N.Y.; Deutscher (1990) *Methods in Enzymology Vol. 182: Guide to Protein Purification.*, Academic Press, Inc. N.Y.). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (see, e.g., Debinski et al. (1993) *J. Biol. Chem.,* 268: 14065-14070; Kreitman and Pastan (1993) *Bioconjug. Chem.,* 4: 581-585; and Buchner, et al. (1992) *Anal. Biochem.,* 205: 263-270).

One of skill would recognize that modifications can be made to the fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

IV) Pharmaceutical Compositions.

The prostate cancer specific antibodies, and/or chelates, and/or chimeric moieties of this invention are useful for parenteral, topical, oral, or local administration (e.g. injected into a tumor site), aerosol administration, or transdermal administration, for prophylactic, but principally for therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the fusion proteins and pharmaceutical compositions of this invention, when administered orally, are preferably protected from digestion. This can be accomplished by a number of means known to those of skill in the art, e.g., by complexing the protein with a composition to render it resistant to acidic and enzymatic hydrolysis or by packaging the protein in an appropriately resistant carrier such as a liposome. Means of protecting proteins from digestion are well known in the art.

The pharmaceutical compositions of this invention are particularly useful for parenteral administration, such as intravenous administration or administration into a body cavity or lumen of an organ. The compositions for administration will commonly comprise a solution of the chimeric molecule dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of chimeric molecule in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as *Remington's Pharmaceutical Science,* 15th ed., Mack Publishing Company, Easton, Pa. (1980).

The compositions containing the present antibodies and/or chimeric molecules (e.g. fusion proteins) or a cocktail thereof (i.e., with other proteins) can be administered for therapeutic treatments. In therapeutic applications, compositions are administered to a patient suffering from a disease, e.g., a cancer, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient.

It will be appreciated by one of skill in the art that there are some regions that are not heavily vascularized or that are protected by cells joined by tight junctions and/or active transport mechanisms which reduce or prevent the entry of macromolecules present in the blood stream One of skill in the art will appreciate that in these instances, the therapeutic compositions of this invention can be administered directly to the tumor site. Thus, for example, prostate tumors can be treated by administering the therapeutic composition directly to the tumor site (e.g., through a surgically implanted catheter).

Alternatively, the therapeutic composition can be placed at the target site in a slow release formulation. Such formulations can include, for example, a biocompatible sponge or other inert or resorbable matrix material impregnated with the therapeutic composition, slow dissolving time release capsules or microcapsules, and the like.

Typically the catheter or time release formulation will be placed at the tumor site as part of a surgical procedure. Thus, for example, where major tumor mass is surgically removed, the perfusing catheter or time release formulation can be emplaced at the tumor site as an adjunct therapy. Of course, surgical removal of the tumor mass may be undesired, not required, or impossible, in which case, the delivery of the therapeutic compositions of this invention may comprise the primary therapeutic modality.

V. Kits.

Where a radioactive, or other, effector is used as a diagnostic and/or therapeutic agent, it is frequently impossible to put the ready-for-use composition at the disposal of the user, because of the often poor shelf life of the radiolabeled compound and/or the short half-life of the radionuclide used. In such cases the user can carry out the labeling reaction with the radionuclide in the clinical hospital, physician's office, or laboratory. For this purpose, or other purposes, the various reaction ingredients can then be offered to the user in the form of a so-called "kit". The kit is preferably designed so that the manipulations necessary to perform the desired reaction should be as simple as possible to enable the user to prepare from the kit the desired composition by using the facilities that are at his disposal. Therefore the invention also relates to a kit for preparing a composition according to this invention.

In certain embodiments, such a kit according to the present invention comprises one or more prostate cancer specific antibodies of this invention. The antibodies can be provided, if desired, with inert pharmaceutically acceptable carrier and/or formulating agents and/or adjuvants is/are added. In addition, the kit optionally includes a solution of a salt or chelate of a suitable radionuclide (or other active agent), and (iii) instructions for use with a prescription for administering and/or reacting the ingredients present in the kit.

The kit to be supplied to the user may also comprise the ingredient(s) defined above, together with instructions for use, whereas the solution of a salt or chelate of the radionuclide, defined sub (ii) above, which solution has a limited shelf life, may be put to the disposal of the user separately.

The kit can optionally, additionally comprise a reducing agent and/or, if desired, a chelator, and/or instructions for use of the composition and/or a prescription for reacting the ingredients of the kit to form the desired product(s). If desired, the ingredients of the kit may be combined, provided they are compatible.

In certain embodiments, the complex-forming reaction with the prostate cancer specific antibody can simply be produced by combining the components in a neutral medium and causing them to react. For that purpose the effector may be presented to the antibody in the form of a chelate.

When kit constituent(s) are used as component(s) for pharmaceutical administration (e.g. as an injection liquid) they are preferably sterile. When the constituent(s) are provided in a dry state, the user should preferably use a sterile physiological saline solution as a solvent. If desired, the constituent(s) may be stabilized in the conventional manner with suitable stabilizers, for example, ascorbic acid, gentisic acid or salts of these acids, or they may comprise other auxiliary agents, for example, fillers, such as glucose, lactose, mannitol, and the like.

While the instructional materials, when present, typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Identification of Clinically Significant Tumor Antigens by Selecting Phage Antibody Library on Tumor Cells in Situ Using Laser Capture Microdissection

Experimental Procedures

Creating a Sublibrary Enriched for Binders to Functional Tumor Cell Surface Epitopes A sublibrary was created by selecting a naïve phage antibody display library on a panel of tumor cell lines under internalizing conditions. The preparation and selection of a phage antibody display library has been described previously (Liu et al. (2004) Cancer Res. 64: 704-710; Poul et al. (2000) J. Mol. Biol. 301: 1149-1161). Briefly the phage library was preincubated with a panel of non-tumorigenic cells including BPH-1, human mammary epithelial cells, MCF10A, and human fibroblasts to remove binders to common cell surface antigens. The predepleted library was then incubated with a panel of prostate cancer cell lines (PC3 and Du-145) at 37° C. for 2 h; washed twice with 100 mM glycine, pH 2.8, in the presence of 150 mM NaCl; and washed once with PBS, pH 7.0. Internalized phage were recovered by lysing the cells with 100 mM triethylamine, propagated in TG1, and purified by precipitation with polyethylene glycol 8000 as described previously (1), thereby creating a sublibrary that is enriched for binders to internalizing cell surface molecules. The sublibrary contained $1-5 \times 10^5$ copies of about $10^6$ independent clones at the concentration of $1-5 \times 10^{11}$ cfu/ml.

Selection of Antibodies Targeting Tumor Cells In Situ by LCM

Selections were performed on both frozen and paraffin-embedded prostate cancer tissues. For selection on frozen tissue slides, 5 μm sections from prostate cancer specimens were cut onto Leica MembraneSlides (MicroDissect, Mittenaar, Germany), stained with hematoxylin, and incubated with the sublibrary (0.5 ml of $5 \times 10^{11}$ cfu/ml stock) at room temperature for 1 h. The slides were then washed three times in PBS to remove unbound phage and prepared for LCM by dehydration in 70, 95, and 100% ethanol in series. For selection on paraffin-embedded tissue, 5 μm sections were cut onto film-coated Leica slides, xylene-treated to remove paraffin, rehydrated through serial 100, 95, and 75% ethanol, placed in PBS with blocking solution at room temperature for 1 h, washed, and incubated with the sublibrary described above. LCM was performed using the Leica AS LMD (Leica Microsystems GmbH, Wetzlar, Germany) that uses a UV pulse laser to excise selected cells from surrounding tissues. Typically 20-50 tumor cells were procured at a time by generating a closed laser path around the group of cells of interest. The cells were then dropped into collection tubes by electrostatic force and gravity. These tissue pieces were stored at −80° C. until analysis.

Recovery of Phage Antibody from LCM-Procured Tissue Pieces

Genes encoding scFv fragments were amplified by PCR from LCM-procured tumor pieces using the following primer pairs: Fd2 (TTT TTG GAG ATT TTC AAC, SEQ ID NO:348) and Fdseq (GAA TTT TCT GTA TGA GG, SEQ ID NO:349). The amplified fragments were digested by SfiI and NotI, purified, and ligated into Fd-Tet vectors precut with the same restriction enzymes (Liu et al. (2004) Cancer Res. 64: 704-710). The ligation products were used to transform chemically competent TG1. Each LCM library contained $>10^5$ independent clones. The number of unique phage antibodies was determined by patterns of BstNI digestion (Liu et al. (2004) Cancer Res. 64: 704-710; Liu and Marks (2000) Anal. Biochem. 286: 119-128). When restriction digestion patterns showed ambiguity, phage antibody genes were sequenced to determine their uniqueness.

Initial Analysis of Selection Output by FACS

Prostate cancer (PC3 and Du-145) or non-tumorigenic control (BPH-1) cells were incubated with phage antibody ($5 \times 10^{11}$ cfu/ml) for 1 h at 4° C. Bound phages were detected by FACS (LSRII, BD Biosciences) using biotinylated anti-M13 antibody (Sigma, diluted 1:1000) followed by streptavidin-phycoerythrin (BIOSOURCE/Invitrogen, diluted 1:1000) (Liu et al. (2004) Cancer Res. 64: 704-710) (see, e.g., FIG. 3). Phage antibodies that showed positive binding were identified and sequenced.

Further Analysis of Selection Output by Immunohistochemistry

Sections of prostate cancer tissue (frozen and paraffin-embedded) and normal human tissues were provided by the Genitourinary Tissue Core of the University of California, San Francisco Comprehensive Cancer Center. All tissues were collected with consent at the Core using protocols approved by the Committee on Human Research. For immunohistochemical analysis, tissue sections were incubated with biotinylated, monomeric scFv (50 μg/ml) at room temperature for 1 h, washed with PBS, and incubated with horseradish peroxidase-conjugated streptavidin at a dilution of 1:1000 (Sigma) for 30 min. Binding was detected using diaminobenzidine (DAB) as the substrate (Sigma) (Liu et al. (2004) Cancer Res. 64: 704-710) (see, e.g., FIG. 4).

Expression, Purification, and Biotinylation of scFv Fragments

Two forms of soluble antibody fragments, scFv and (scFv')$_2$, were produced (Liu et al. (2004) Cancer Res. 64: 704-710). The scFv gene was subcloned into the secretion vector pUC119mycHis, adding a c-Myc epitope tag and hexahistidine tag at the C terminus of the scFv (Id.). To create the (scFv')$_2$ dimer for immunoliposome studies, the c-Myc epitope tag was removed, and a free cysteine was introduced at the C terminus of the scFv preceding the hexahistidine tag as described previously (Liu et al. (2004) Cancer Res. 64: 704-710). scFv monomer or (scFv')$_2$ dimer proteins were harvested from the bacterial periplasmic space and purified by IMAC as described previously (Id.). To biotinylate scFv for FACS analysis, affinity-captured monomeric scFv fragments were washed in PBS and incubated with NHS-LC-biotin (Pierce) at 0.5 mg/ml for 20 min prior to elution with 250 mM imidazole.

Assay for Internalizing and Intracellular Delivery

Figure 5A:
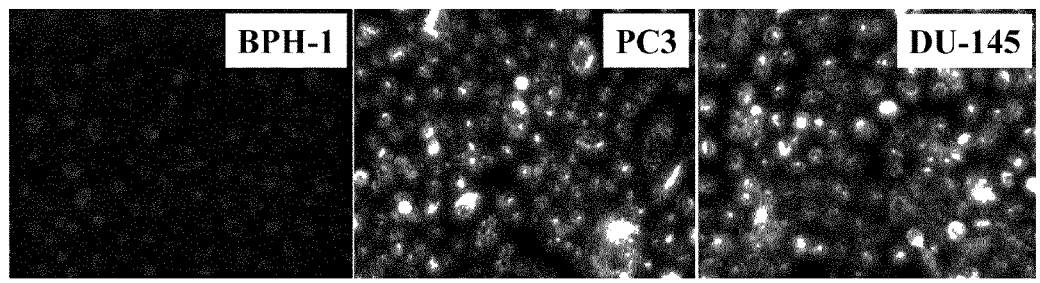
FIGS. 5A, 5B, 5C illustrate the internalization of immunoliposomes. Fluorescent liposomes conjugated with the UA20 scFv were tested for internalization into prostate cancer cells.
Figure 5B:
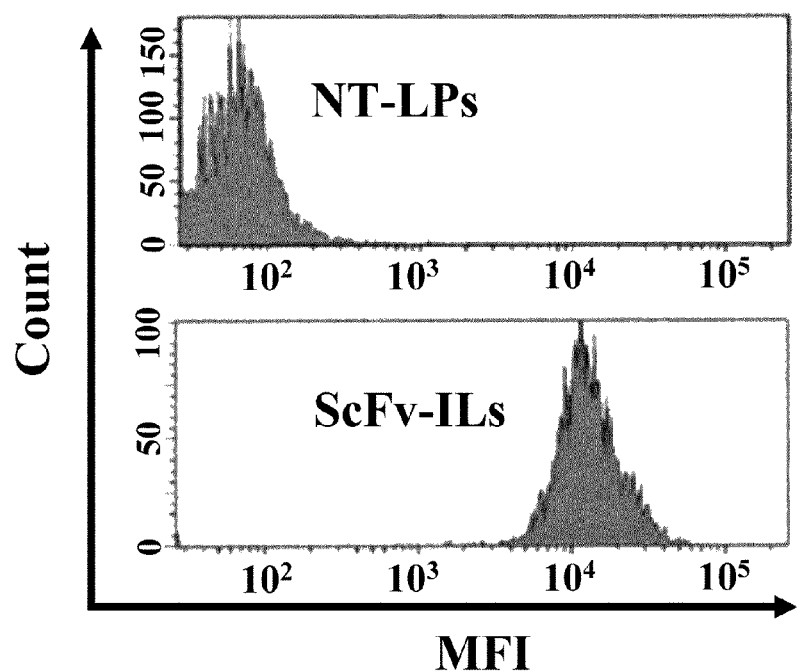
Figure 5C:
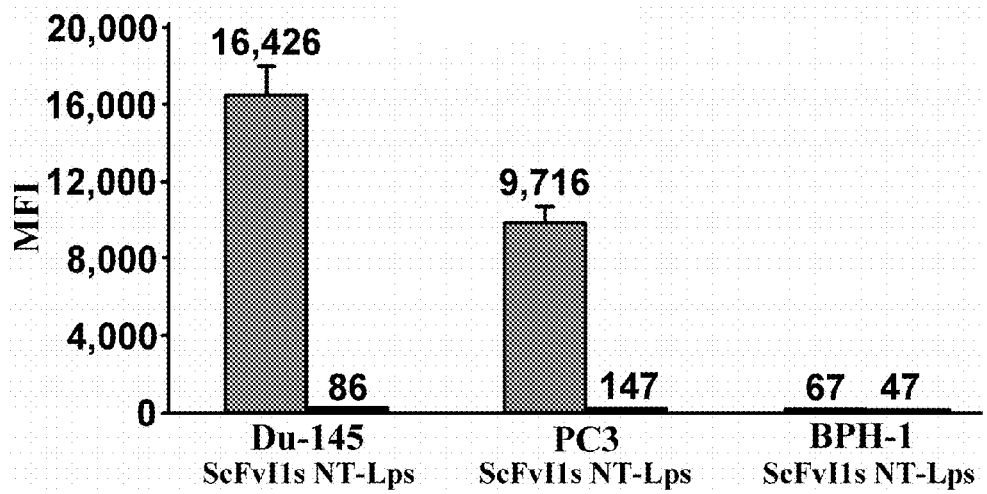

Unilamellar liposomes composed of 1,2-distearoyl-sn-glycero-3-phosphocholine, cholesterol, DiIC18(3)-DS, and β-(N-maleimido)propionyl poly(ethylene glycol)-1,2-distearoyl-3-sn-phosphoethanolamine (molar ratio, 6:6:0.03:0.03) were prepared as described previously (Nielsen et al. (2002) Biochim. Biophys. Acta 1591: 109-118; Saito et al. (2005) Exp. Neurol. 196: 381-389; Saito et al. (2004) Cancer Res. 64: 2572-2579). His6-tagged (scFv')$_2$ were reduced to the monomeric form through incubation with 20 μg/ml β-mercaptoethylamine for 45 min at room temperature (Nielsen et al. (2002) Biochim. Biophys. Acta 1591: 109-118). The reduced monomeric scFv fragments were conjugated with DiI1 8(3)-DS liposomes in 30 μg of protein/μmol of phospholipids at 37° C. for 4 h. To assess intracellular liposome delivery, scFv'-conjugated liposomes were incubated at 37° C. for 2 h with cells, which were then washed three times with saline containing 1 mM EDTA, 250 mM imidazole to remove cell surface-bound liposomes that failed to internalize. Uptake of scFv-DiIC1 8(3)-DS immunoliposomes was determined by FACS and by an inverted fluorescence microscope (Eclipse TE300, Nikon Corp.) (see, e.g., FIG. 5).

Results.

Selection of Phage Antibody Binding to Clinically Relevant Internalizing Epitopes by LCM Selection was performed according to the scheme outlined in FIG. 1. We aimed to identify phage antibodies that bind to tumor epitopes present on actual cases of cancer and to further identify a subset of functional phage antibodies that bind to internalizing epitopes so that they may be exploited to deliver payload to the interior of tumor cells.

We devised a multistep strategy to achieve these aims (FIG. 1). First, a sublibrary was generated that is enriched for binders to cell surface receptors including those that are internalizing. This was accomplished by counterselecting a naïve phage antibody library containing $5 \times 10^8$ unique scFv fragments on a panel of non-tumorigenic epithelial cell lines to remove binders to common cell surface antigens followed by selecting on a panel of live tumor cell lines such as the hormone refractory prostate cancer lines PC3 and Du-145 (Liu et al. (2004) *Cancer Res.* 64: 704-710; Liu and Marks (2000) *Anal. Biochem.* 286: 119-128; O'Connell et al. (2002) *J. Mol. Biol.* 321: 49-56; Huie, et al. (2001) *Proc. Natl. Acad. Sci., USA*, 98: 2682-2687). By manipulating the selection conditions to preferentially recover internalized phage, a sublibrary enriched for internalizing phage antibody was created (Liu et al. (2004) *Cancer Res.* 64: 704-710; Gao et al. (2003) *J. Immunol. Methods* 274: 185-197; Poul et al. (2000) *J. Mol. Biol.* 301: 1149-1161; Becerril et al. (1999) *Biochem. Biophys. Res. Commun.* 255: 386-393). Next the enriched sublibrary was incubated with tumor tissue slides, and tumor cells along with bound phage were procured by LCM (FIG. 2). The scFv genes were amplified by PCR and recloned into a phage display vector to generate a population of phage antibody that were either screened or used as input for the next round of selection (FIG. 2). Following one or two rounds of selection on tissue, the output was screened first on tumor cell lines to identify positive binders. Following sequencing, unique scFv fragments were further studied by IHC on tissue slides according to the scheme outlined in FIG. 1. This selection scheme effectively restricts selection outcomes to phage antibodies that bind to epitopes present on both tumor cell lines and tumor cells in situ from actual cases. Moreover these antibodies possess internalizing functions that can be exploited for targeted payload delivery. Antibodies that meet these criteria will likely have significant therapeutic values.

Initial Analysis of Selection Output: Binding to Tumor Cell Lines

Figure 3:
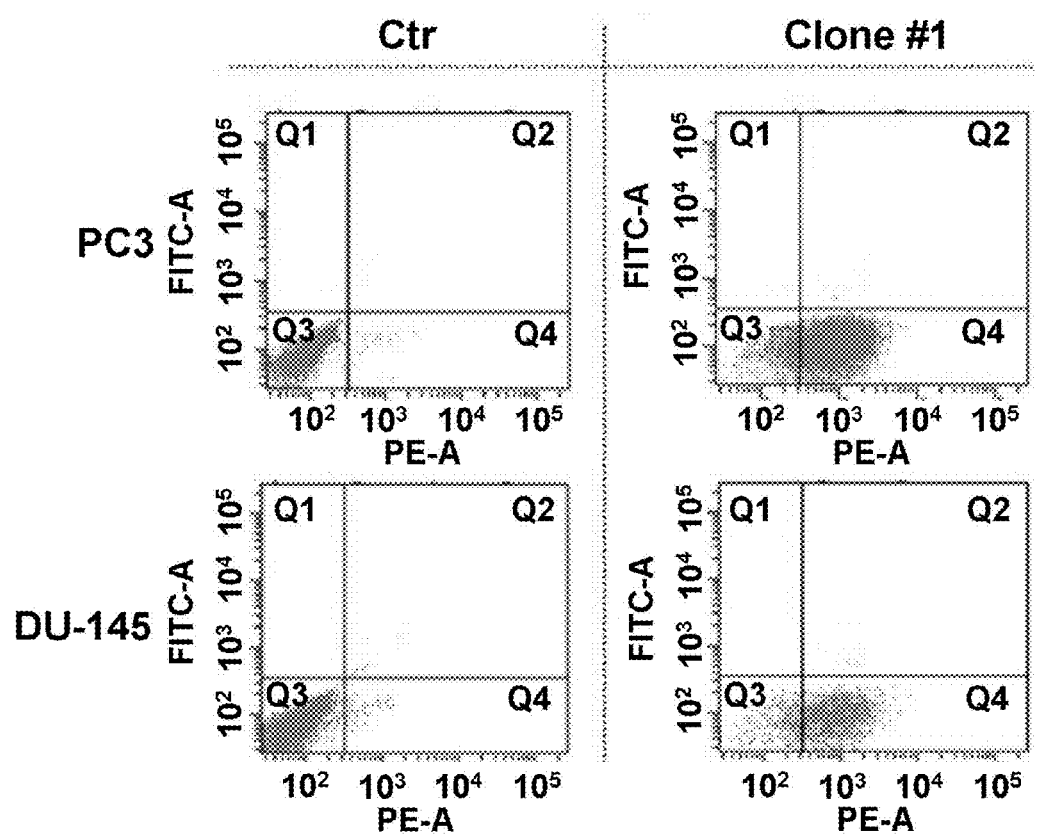
FIG. 3 illustrates initial screening of selection output. FACS analysis was performed on tumor cell lines to identify positive clones, restricting the number of phage antibody that needed to be screened on tissue slides. Ctr, helper phage. Clones 1-4, four positive clones randomly chosen from the output following one round of LCM-based selection. Because these antibodies bound to both PC3 and Du-145 cells, it is likely that they bind to tumor antigens instead of artifacts associated with slide preparation. Tumor specificity and clinical relevance were further studied by IHC. PE-A, phycoerythrin channel; FITC-A, FITC channel.

Random clones from the sublibraries created after LCM-based selections were screened on PC3 and Du-145 cells by FACS (FIG. 3). More than 600 clones from various LCM-derived sublibraries were screened. Only those clones that bound to both PC3 and Du-145 cells were chosen for further analysis because they are more likely to recognize tumor cell surface antigens as opposed to artifacts associated with a particular tissue slide. The fraction of CaP cell line-binding clones ranged from 15 to 88% (Table 4). Unique clones were identified by DNA sequencing. Thirteen unique phage antibodies were found from a total of 85 positive clones sequenced. We focused on two scFv fragments, UA20 and 585II41, for further characterization. The UA20 scFv was obtained from selection on paraffin-embedded prostate cancer tissue. The 585II41 scFv was obtained from selection on fresh frozen prostate cancer tissue.

TABLE 4

Summary of selection results. Four paraffin-embedded and two frozen CaP tissues were used in the selection. The sublibraries constructed from PCR products contained $2\text{-}8 \times 10^5$ unique clones. Binders to both PC3 and Du-145 cell lines were identified from each sublibrary by FACS screening. Between 10 and 20 positive clones from each group were sequenced to identify unique clones. Thirteen unique clones were identified from a total of 85 clones sequenced.

| Cases | Tissue slides | Tumor grades (Gleason scores) | No. clones in sublibrary | Cell line binders |
|---|---|---|---|---|
| CaP 1 | Paraffin | 3 + 4 | $5 \times 10^5$ | 29/188 (15%) |
| CaP 2 | Paraffin | 4 + 5 | $8 \times 10^5$ | 140/188 (75%) |
| CaP 3 | Paraffin | 3 + 4 | $5 \times 10^5$ | 72/288 (25%) |
| CaP 4 | Paraffin | 3 + 4 | $2 \times 10^5$ | 40/96 (42%) |
| CaP 5 | Frozen | 4 + 5 | $7 \times 10^5$ | 85/96 (88%) |
| CaP 6 | Frozen | 3 + 4 | $5 \times 10^5$ | 75/96 (78%) |

Further Analysis of Selection Output: Binding to Tumor Cells In Situ

Figure 4:
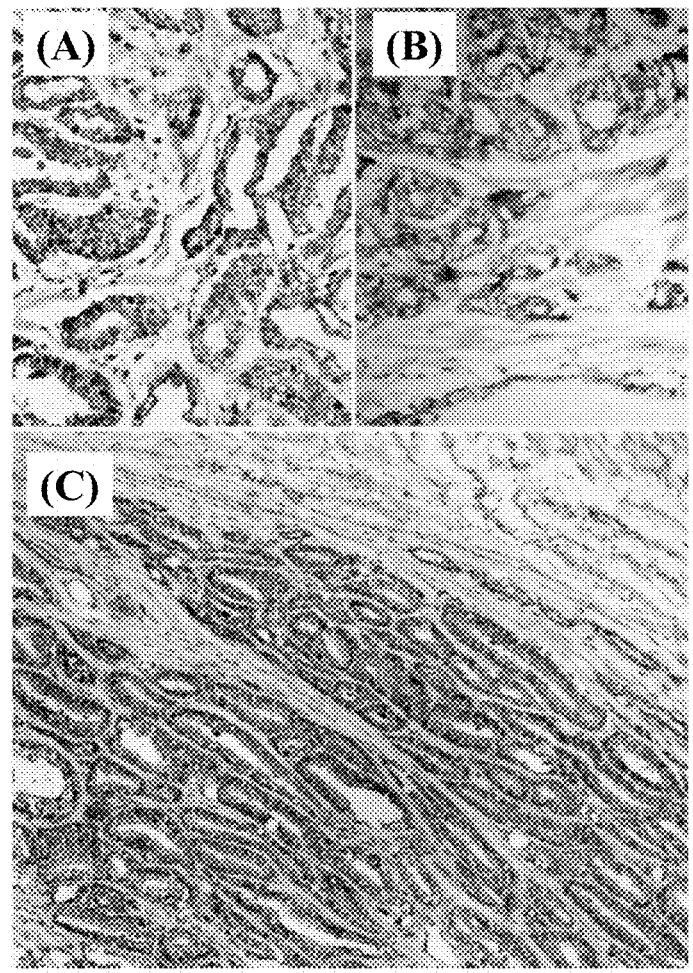
FIG. 4, panels A-C, show the results of immunohistochemistry studies. Biotinylated scFv fragments were used to stain CaP tissues. The UA20 scFv was originally isolated from selection on paraffin-embedded tissues; it stained tumor cells in both frozen and paraffin-embedded tissue slides. The 585II41 scFv was originally isolated from selection on frozen tissues; it stained tumor cells in frozen but not paraffin-embedded tissue slides. Panel A: staining of frozen tissues with UA20 scFv. Panel B: staining of frozen tissues with 585II41 scFv. Panel C: staining of paraffin-embedded CaP tissues with UA20 scFv.

Phage antibodies selected by LCM were expected to bind to clinically relevant antigens on cancer cells in situ. We performed immunohistochemical studies using soluble scFv fragments derived from LCM-selected phage antibody on prostate cancer tissue sections. FIG. 4, panels A-C, shows the staining results of the UA20 and 585II41 scFv fragments on tissue specimens obtained from Gleason 3+4 patients. On both frozen and paraffin-embedded tissue slides, the UA20 scFv showed an intense staining of tumor epithelium with minimal staining of normal adjacent prostate epithelium (FIG. 4, panels A and C). The 585II41 scFv also stained tumor cells intensely on frozen tissue slides (FIG. 4, panel B). Some basal cells in normal epithelium adjacent to tumor were also stained with reduced intensity (Table 5). The 585II41 scFv did not stain paraffin-embedded slides (data not shown), consistent with the fact that it was originally identified from selection on frozen tissue slides. These experiments indicate that antibodies obtained from LCM selection bind to antigens that exist in patient specimens and thus are clinically relevant to human prostate cancer. The corresponding antigens are likely targets for therapeutic intervention.

TABLE 5

Immunohistochemistry (IHC) results of the 585II41 and UA20 scFv fragments on a panel of frozen CaP and normal tissues. The numbers of cases studied are indicated. Biotinylated scFv fragments were first tested on cell lines to ensure binding activity and then used for IHC studies. As a control, a random scFv with no binding activity to cell lines was used to register the background level of staining. No change, no change in staining level was observed when compared with the result of the control scFv

| Tissues | 585II41 | UA20 |
|---|---|---|
| CaP | Strong stain on tumor (8/8); some stain on basal cells (5/8); and weak stain on adjacent normal (3/8) | Strong stain on tumor (8/8); some weak stain on adjacent normal (2/8) |
| Normal: | | |
| Brain | No change (7/7) | No Change (4/4) |
| Heart | No change (1/1) | No Change (4/4) |
| Liver | No change (3/4); Some bile duct stain (1/4) | No Change (4/4) |

TABLE 5-continued

Immunohistochemistry (IHC) results of the 585II41 and UA20 scFv fragments on a panel of frozen CaP and normal tissues. The numbers of cases studied are indicated. Biotinylated scFv fragments were first tested on cell lines to ensure binding activity and then used for IHC studies. As a control, a random scFv with no binding activity to cell lines was used to register the background level of staining. No change, no change in staining level was observed when compared with the result of the control scFv

| Tissues | 585II41 | UA20 |
|---|---|---|
| Kidney | No change (4/4) | No Change (4/4) |
| Lung | No change of alveoli (5/5); stain bronchial epithelial (5/5) | No change of alveoli and bronchial epithelial (5/5) |
| Colon | No change (4/4) | No change (4/4) |
| Bladder | No change (2/3); faint epithelial stain (1/3) | No change (2/3); faint epithelial and smooth muscle stain (1/3) |
| Oral | No change (3/4); some stain of salivary gland (1/4) | No change (4/4) |

In a subsequent study, additional immunohistochemistry was performed for the UA20, 585II41, 585II56 and UA8 scFv fragments on a panel of frozen CaP and normal tissues (see, e.g., Table 6). As a control, a scFv with no binding activity to cell lines was used to register the level of background staining.

TABLE 6

Immunohistochemistry (IHC) results of the UA20, 585II41, 585II56 and UA8 scFv fragments on a panel of frozen CaP and normal tissues. The numbers of cases studied are indicated. The 585II41 scFv binds to CD166, a known marker for prostate cancer.

| Tissues | UA20 | 585II41 (H3 variant) | 585II56 | UA8 |
|---|---|---|---|---|
| CaP | Strong stain on tumor (16/16); some weak stain on adjacent normal (3/16) | Strong stain on tumor (16/16); some stain on basal cells (10/16); and weak stain on adjacent normal (7/16) | Strong stain on high grade tumor (7/8); variable stain on low grade (4/8) and adjacent normal (7/16) | Strong stain on tumor (16/16); some stain on adjacent normal (9/16) |
| Normal | | | | |
| Brain | No stain (4/4) | No stain (7/7) | No stain (7/7) | No stain (7/7) |
| Heart | No stain (4/4) | No stain (1/1) | No stain (1/1) | No stain (1/1) |
| Liver | No stain (4/4) | No stain (3/4); some bile duct stain (1/4) | No stain (4/4) | No stain (4/4) |
| Kidney | No stain (4/4) | No stain (4/4) | No stain (4/4) | No stain (4/4) |
| Lung | No stain (5/5) | No stain of alveoli (5/5); stain bronchial epithelial (5/5) | No stain (5/5) | No stain (5/5) |
| Colon | No stain (4/4) | No stain except ganglion (4/4) | No stain (4/4) | No stain (4/4) |
| Bladder | No stain (2/3); faint stain (1/3) | No stain (2/3); faint epithelial stain (1/3) | No stain (3/3) | No stain (2/3); faint smooth muscle stain (1/3) |
| Oral | No stain (4/4) | No stain (3/4); some stain of salivary gland (1/4) | No stain (4/4) | No stain (4/4) |

Tissue Specificity

To study the cross-reactivity of scFv fragments with normal tissues, we performed IHC studies on a panel of normal frozen human tissues using purified 585II41 and UA20 scFv fragments (Table 5). Compared with controls, the 585II41 scFv showed no significant staining on most normal tissues studied, including the brain, kidney, and heart. There was, however, significant staining of bronchial epithelial cells and skin eccrines. The UA20 scFv, on the other hand, showed a more restricted staining pattern. At the concentration tested (50 μg/ml), the UA20 scFv showed strong staining on prostate cancer tissues but no significant staining on the panel of normal tissues studied (Table 5). We conclude that both scFv fragments recognize tumor cells in situ, and the UA20 scFv has very low cross-reactivity to normal human tissues.

Internalization and Payload Delivery to Prostate Cancer Cells

Phage antibodies selected by LCM were derived from a phage population that was panned on tumor cell lines using a functional selection process targeting receptor-mediated endocytosis. To confirm that selected phage antibodies possessed this phenotype and were endocytosed by CaP cells, the UA20 scFv' with a free cysteine at the C terminus was produced and conjugated to maleimide-activated liposomes containing a fluorescent probe, DiIC18(3)-DS, and incubated with BPH-1 (control), PC3, and Du-145 cells. These immunoliposomes were efficiently endocytosed by both PC3 and Du-1 45 cells (FIG. 5A-5C) with minimal uptake into BPH-1 cells (5). Without conjugated scFv fragments, untargeted liposomes were not taken up by prostate cancer cells (FIG. 5C) Like the UA20 scFv-ILs, the 585II41-targeted liposomes were also efficiently taken up by prostate cancer cells (PC3 and Du-145) (data not shown). These experiments demonstrate that scFv antibodies selected by LCM retain internalizing functions and are capable of mediating efficient and specific payload delivery. These antibodies are candidates for the development of targeted therapeutics against prostate cancer.

Identification of ALCAM as a Tumor Antigen

Figure 6A:
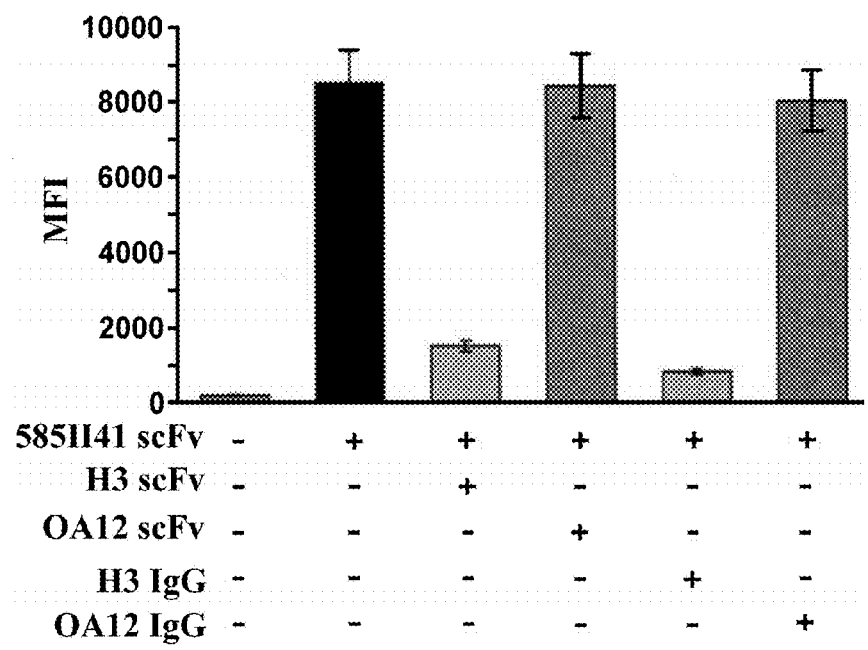
FIGS. 6A and 6B illustrate the identification of ALCAM/MEMD/CD166 as the target of the 585II41 scFv.

The 585II41 scFv was sequenced and found to be highly homologous to a previously identified scFv, H3. These two scFv fragments differ by only two amino acids, none of which are in the CDR3 region that is critical for antigen binding (data not shown). The antigen recognized by the H3 scFv has been identified previously by us as ALCAM, also known as MEMD or CD166 (Kobata and Amano (2005) *Immunol. Cell Biol.* 83: 429-439). We hypothesized that the 585II41 scFv is a variant of the H3 scFv and binds to ALCAM. To test this hypothesis, we performed competition experiments using both H3 scFv and IgG to compete with the 585II41 scFv for binding to prostate cancer cells (Du-145). As controls, an scFv and its corresponding IgG that to ALCAM-expressing cells were included in the experiment. FACS analysis showed that both H3 scFv and IgG competed away binding by 585II41 scFv, whereas the control scFv and IgG did not (FIG. 6A). This indicates that the H3 scFv and the 585II41 scFv target the same antigen, i.e. ALCAM.

Figure 6B:
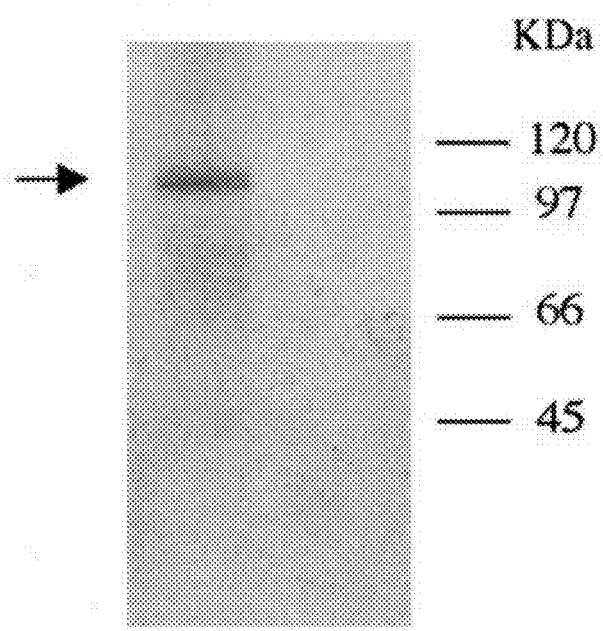

To further confirm that 585II41 scFv binds to ALCAM, we used 585II41 scFv to immunoprecipitate (IP) its target antigen from prostate cancer cell lysates. We probed the IP product with a commercial monoclonal antibody raised against a unique ALCAM peptide (FIG. 6B). This anti-ALCAM mAb recognized the IP product of 585II41 scFv but not that of the control OA12 scFv, thus confirming that ALCAM is the antigen targeted by the 585II41 scFv. In agreement with our own IHC studies, ALCAM has been shown by others to be overexpressed in 86% of prostate cancer cases (Kristiansen et al. (2005) *J. Pathoi.* 205: 359-376). The fact that we identified a binder to a validated prostate cancer marker indicates that our LCM-based selection method is indeed capable of identifying clinically relevant tumor antigens. The antigen recognized by the UA20 scFv is being further characterized.

Discussion

The success of targeted cancer therapy depends in part on the availability of a panel of targeting agents such as mAbs that recognize tumor cell surface antigens present in clinical specimens. Much work has been done to generate mAbs against cell lines derived from primary tumor. It has become evident, however, that when removed from their original tissue environment cultured tumor cells variably up- and down-regulate expression of cell surface molecules relative to primary tumor cells. It is challenging yet desirable to identify the overlapping surface epitope space between tumor cell lines and tumor cells in actual cases.

We developed an LCM-based strategy that allows the selection of phage antibody against tumor cells in situ within their proper stromal microenvironment. By preselecting a naïve phage antibody library on a panel of tumor cell lines under internalizing conditions, we created a sublibrary that is enriched for binders to functional cell surface epitopes. This sublibrary was then used for further selection on tissue slides. By precisely procuring tumor cells along with bound phage by LCM, we identified phage antibodies that bind to clinically represented tumor antigens. These antibodies meet the following criteria: 1) binding to internalizing cell surface epitopes present on tumor cell lines and 2) binding to epitopes present on tumor cells in situ. The ability to deliver payload intracellularly to target cells present in actual cases of human cancer makes these antibodies attractive candidates for therapeutic development.

We identified ALCAM, also known as MEMD or CD 166, as the target for one of the selected antibodies. ALCAM, a member of the immunoglobulin superfamily, was originally shown to be overexpressed on highly metastatic melanoma cells (Oegen et al. (1998) *Am. J. Pathol.* 152: 805-813). Recently it has been shown to be overexpressed in prostate carcinomas and to be predictive of prostate-specific antigen relapse (Kristiansen et al. (2005) *J. Pathol.* 205: 359-376). The fact that we found an scFv targeting a validated prostate cancer maker demonstrates the effectiveness of our approach.

ALCAM has also been identified by selecting a phage antibody library on an ovarian tumor cell line, and an immuno-toxin has been made using the anti-ALCAM scFv (Piazza et al. (2005) *J. Cell Sci.* 118: 1515-1525). As this study dealt with cell line selection only, future IHC study will help determine whether ALCAM is indeed a marker for ovarian cancer. Therapies targeting ALCAM should also take into consideration its distribution on normal tissues as our IHC study showed that ALCAM is expressed on normal bronchial epithelial cells.

The sublibraries that were used for the LCM-based selection were generated from selection on tumor cell lines following counterselection on a panel of non-tumorigenic cell lines. As no cell lines are truly normal, it is possible that these non-tumorigenic cell lines share some surface antigens with tumor cells. To account for this possibility and to preserve antigens that are overexpressed, if not exclusively expressed, by tumor cells, we performed a moderate counterselection. We aimed to reduce binders to the most common cell surface antigens but not to eliminate all binders that cross-react with non-tumorigenic cell lines. The issues of tumor specificity and clinical relevance were addressed by direct selection and analysis on tissue sections instead.

We found some unexpected features associated with the LCM-based selection that may have hindered the application of LCM in phage antibody display. Most curiously, phage bound to LCM-procured tissue pieces seemingly lose their ability to infect bacteria, posing a challenge to library selection. We had initially sought to recover bound phage by standard methods, i.e. elution of phage with high pH buffer followed by neutralization and infection of TG1 bacterial cells (Lu and Kapila (2004) *Oral Surg. Oral Med. Oral Pathol. Oral Radiol. Endod.* 98: 692-697; Yao et al. (2005) *Am. J. Pathol.* 166, 625-636). However, little bacterial growth was observed under various culture conditions (data not shown). This phenomenon was seen even in manually dissected tissue pieces that were not exposed to the UV laser used in the Leica LMD system (data not shown). Exposure to ethanol during slide preparation for LCM seems to be a factor contributing to the observed reduction in phage viability. Regardless of the cause, we circumvented this problem by using the genomes of phages bound to the procured cancer cell pieces as templates for amplification of scFv genes by PCR.

We identified 13 unique phage antibodies after sequencing 85 tumor-reactive clones. Because the sample size was small, it was not possible to predict the total number of unique clones in the selection output. Determining population diversity based on limited sample size is a complex statistical problem that cannot be solved by simple extrapolation (Hughes et al. (2001) *Appl. Environ. Microbiol.* 67: 4399-4406; Hughes and Hellmann (2005) *Meth. Enzymol.* 397: 292-308).

Although LCM has the capacity to procure a single cell, we generally opted to procure a group of 20-50 tumor cells for phage antibody selection. We found that it was rather difficult to recover phage antibodies from single cell procurement even by PCR amplification. In the rare cases that the phage antibodies were recovered, the diversity of scFv fragments was very low (in two of three cases, only a single unique clone was found among the 20 sequenced). Either the UV laser path encircling the single cell came too close to the bound phage, thereby damaging its DNA and reducing its viability for recovery, or there may be less than one recoverable phage bound per cell on tissue slides. In any event, we found that it was practical to procure 20-50 cells at a time for phage selection. When a large cluster of topologically contiguous tumor cells cannot be found, we generally procured several small three to five-cell clusters for analysis.

In the future, we envision the creation of a generic sublibrary that contains binders to a broad spectrum of cell surface antigens. This can be done by selecting the naïve phage display library on a large panel of existing tumor cell lines such as NCI 60 (Covell et al. (2005) *Proteins* 59: 403-433; Garraway and Sellers (2006) *Cancer Res.* 66: 2506-2508). This sublibrary can then be used as a universal input for LCM-based selection on tissues. Given the amount of paraffin-embedded and frozen tissues already archived, we anticipate the discovery of increasing numbers of functional epitopes present in actual cases of cancer.

Example 2

SPECT/CT and Biodistribution Study of UA20 scFv

Figure 9:
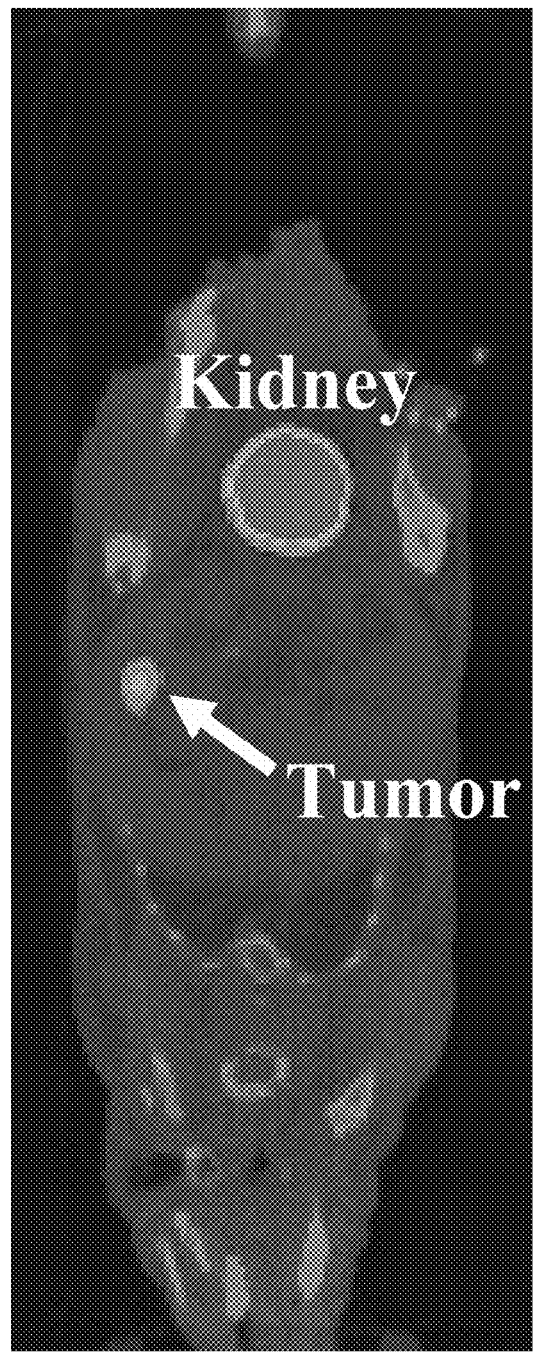
FIG. 9 shows the results of SPECT/CT imaging of UA20 scFv targeting to prostate cancer Du-145 xenograft tumor (arrow) in nude mice.

To determine the efficiency of the UA20 scFv in tumor targeting in vivo, we performed molecular imaging studies with technetium ($^{99m}$Tc)-labeled scFv and a combined modality SPECT/CT, which allows simultaneous tomographic imaging of gamma-emitting radiopharmaceuticals and anatomic imaging with CT. Immunodeficient mice were injected with 1 million Du-145 cells subcutaneously. Six days later when the tumor was palpable, the mice were injected with either $^{99m}$Tc-labeled UA20 scFv or a $^{99m}$Tc-labeled control scFv (N3M2) and imaged with SPECT/CT, and imaged 3 h post injection. As shown in FIG. 9, prostate cancer xenograft was recognized by $^{99m}$Tc-labeled UA20 scFv but not the control scFv, demonstrating the targeting specificity in vivo. The other organs that showed the greatest contrast were the kidneys, consistent with the route of scFv excretion from the body.

Figure 10A:
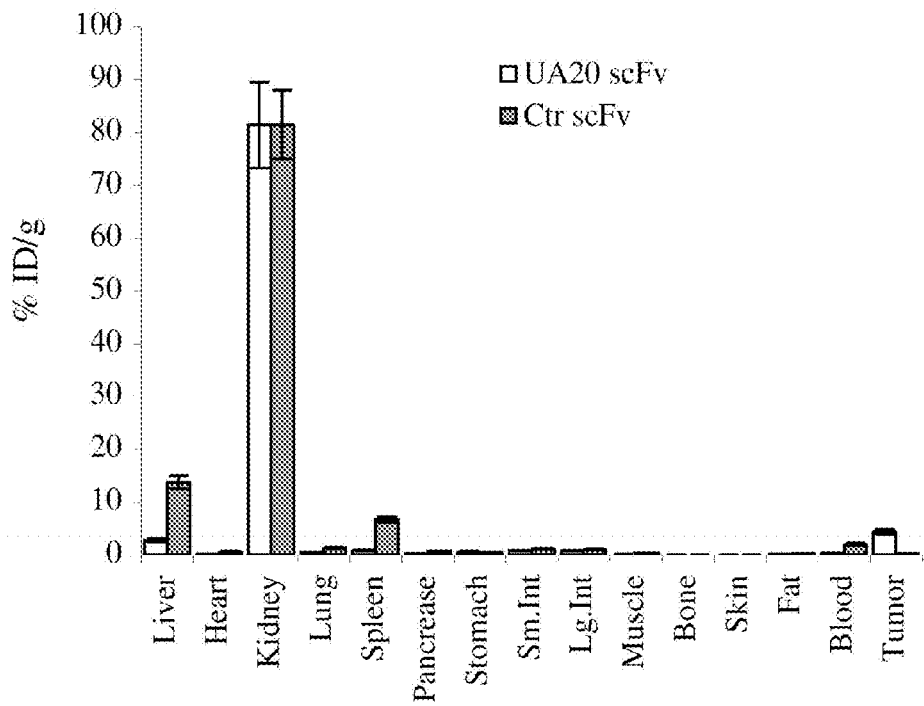
FIGS. 10A, and 10B show the results of biodistribution studies. A, SPECT/CT imaging of UA20 scFv targeting to prostate cancer Du-145 xenograft tumor (arrow) in nude mice.
Figure 10B:
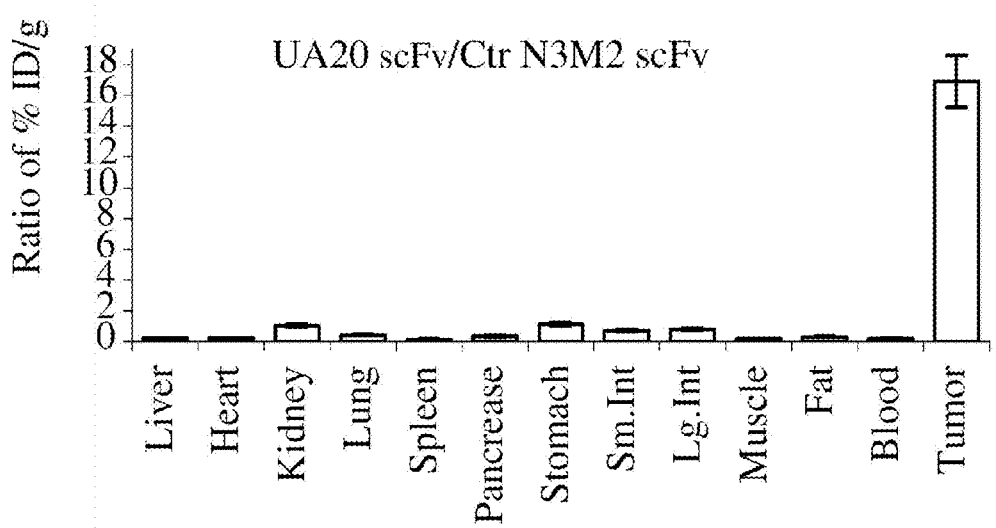

Next, we performed biodistribution studies using the $^{99m}$Tc-labeled UA20 and the control scFvs. Antibody accumulation in tumor, blood, and major organs was determined at 6 h post injection. As shown in FIGS. 10A and 10B, the UA20 scFv showed about 17-fold higher tumor accumulation in mice carrying Du-145 xenografts than control mice.

Results of a subsequent biodistribution study are shown in Table 7.

TABLE 7

Biodistribution study. The values of % ID/g tissue for both the UA20 scFv and the control non-binding N3M2 scFv were shown. The experiment was done using $^{99m}$Tc-labeled scFvs on Du-145 xenografts.

| Organ | UA20 ScFv | Ctr scFv |
|---|---|---|
| Liver | 2.74 | 13.77 |
| Heart | 0.13 | 0.64 |
| Kidney | 81.44 | 81.47 |
| Lung | 0.57 | 1.38 |
| Spleen | 0.84 | 6.68 |
| Pancreas | 0.23 | 0.67 |
| Stomach | 0.64 | 0.56 |
| Sm Int. | 0.80 | 1.15 |
| Lg. Int. | 0.81 | 1.03 |
| Muscle | 0.06 | 0.35 |
| Fat | 0.07 | 0.23 |
| Blood | 0.37 | 1.97 |
| Tumor | 4.40 | 0.26 |

Sm. Int., small intestine.
Lg. Int., large intestine.

It is noted that the UA20 scFv has unusually good biodistribution patterns with tumor % ID/gm over 4. Most scFvs, without further modifications such as diabodies and minibodies, have % ID/gm about 1. Moreover, background in mouse is very low (several fold lower than other scFvs that we have tested for all vital organs). Therefore, UA20 is an excellent candidate for imaging and/or therapy.

Example 3

Additional Comments Regarding Antibodies

Figure 11:
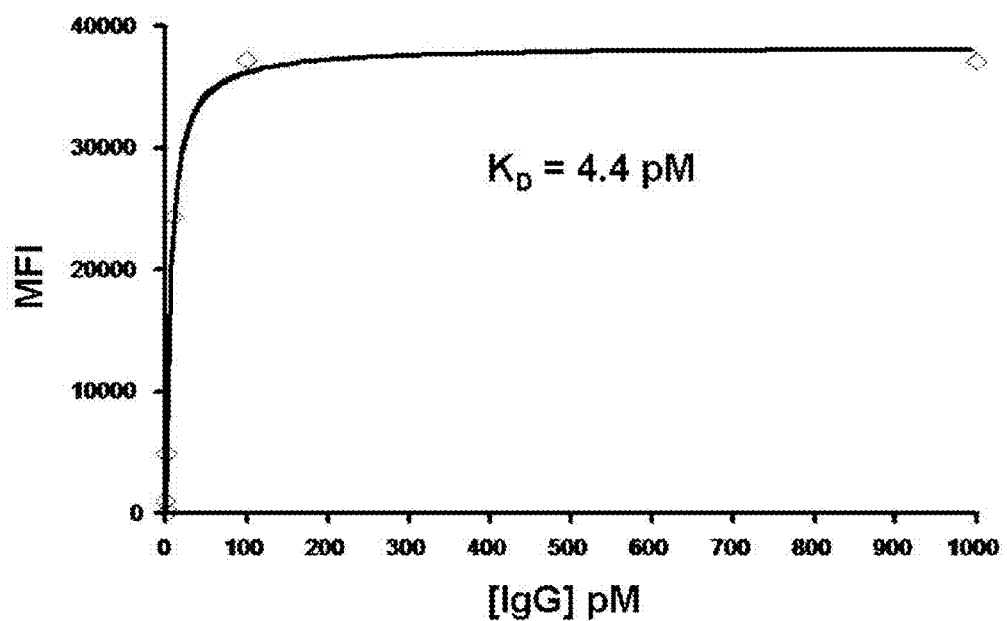
FIG. 11 shows the results of a measurement of apparent dissociation equilibrium constant (KD) of the anti-ALCAM IgG1 (585II41.1, also known as H3) on prostate cancer Du-145 cells by FACS. Monodispersed DU-145 cells were incubated with varying concentrations of IgG1s at 4° C. overnight to allow equilibrium binding. After washing, bound human IgG1s were detected by R-phycoerythrin-conjugated goat anti-human secondary antibody and analyzed by FACS. Mean fluorescence intensity (MFI) values were plotted and the KD was determined by curve fitting using GraphPad (GraphPad Software, San Diego, Calif.).

The H3 sequence is identical to clone #11 (not 10; differing by one a.a.). H3 is 585II41.1. $K_D$ data for H3 is shown in FIG. 11 (KD=4.4 pM). To further clarify, 585II41 antibody binds to ALCAM, and is a variant of 585II41.1 that is H3. 585II41 and 585II41.1 have identical properties despite a one amino acid difference.

The Examples provided above are correct as 585II41 (clone #10) binds to ALCAM. It just that it is not exactly H3, which is 585II41.1 (clone #11).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated antibody or antigen binding fragment thereof that specifically binds and is internalized into a prostate cancer cell, wherein said antibody or antigen binding fragment thereof comprises a heavy chain variable (VH) region comprising the three complementarity determining regions (CDRs) in the VH region of SEQ ID NO:8 and a light chain variable (VL) region comprising the three CDRs of the VL region of SEQ ID NO:8.

2. The antibody or antigen binding fragment thereof of claim 1, wherein said antibody or antigen binding fragment thereof comprises the VH domain and the VL domain of the antibody UA20 (SEQ ID NO:8).

3. The antibody or antigen binding fragment thereof of claim 1, wherein said antigen binding fragment is selected from the group consisting of a Fab, a (Fab')$_2$, an scFv, and an (ScFv')$_2$.

4. The antibody or antigen binding fragment thereof of claim 1, wherein said antigen binding fragment is a single chain antibody UA20 (SEQ ID NO: 8).

5. A chimeric moiety, said moiety comprising an effector attached to an antibody or antigen binding fragment thereof of any one of claims 1, 2, and 3.

6. The chimeric moiety of claim 5, wherein said effector is selected from the group consisting of an epitope tag, a second antibody, a label, a cytotoxin, a liposome, a radionuclide, a drug, a prodrug, a viral particle, a cytokine, and a chelate.

7. A pharmaceutical formulation said formulation comprising: a pharmaceutically acceptable excipient and an antibody or antigen binding fragment thereof according to any one of claims 1, 2, and 3.

8. A pharmaceutical formulation said formulation comprising: a pharmaceutically acceptable excipient and a chimeric moiety comprising an effector attached to an antibody or antigen binding fragment thereof of any one of claims 1, 2, and 3.

9. The pharmaceutical formulation of claim 8, wherein said effector is selected from the group consisting of an epitope tag, a second antibody, a label, a cytotoxin, a liposome, a radionuclide, a drug, a prodrug, a viral particle, a cytokine, and a chelate.

* * * * *

UNITED STATES PATENT AND TRADEMARK OFFICE
CERTIFICATE OF CORRECTION

PATENT NO. : 8,865,873 B2
APPLICATION NO. : 12/724282
DATED : October 21, 2014
INVENTOR(S) : Liu et al.

Page 1 of 1

It is certified that error appears in the above-identified patent and that said Letters Patent is hereby corrected as shown below:

In the Specification

Column 1, Lines 18-22:
Please change "This invention was made in part with Government Support by Grant Nos: R01 CA118919, R21 DK066428-01, and P50 CA8952 from the National Institutes of Health. The Government of the United States of America has certain rights in this invention." to -- This invention was made with government support under grant nos. R01 CA118919, DK066428 and P50 CA089520 awarded by The National Institutes of Health. The government has certain rights in the invention. --

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*